(12) United States Patent
Voegele et al.

(10) Patent No.: US 8,608,652 B2
(45) Date of Patent: Dec. 17, 2013

(54) VAGINAL ENTRY SURGICAL DEVICES, KIT, SYSTEM, AND METHOD

(75) Inventors: James W. Voegele, Cincinnati, OH (US); David B. Griffith, Cincinnati, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 631 days.

(21) Appl. No.: 12/612,911

(22) Filed: Nov. 5, 2009

(65) Prior Publication Data
US 2011/0105850 A1 May 5, 2011

(51) Int. Cl.
*A61B 1/32* (2006.01)

(52) U.S. Cl.
USPC .......................... 600/207; 600/208; 600/210

(58) Field of Classification Search
USPC ...................... 600/201–234; 623/17.11–17.16
See application file for complete search history.

(56) References Cited

U.S. PATENT DOCUMENTS

| | | |
|---|---|---|
| 645,576 A | 3/1900 | Telsa |
| 649,621 A | 5/1900 | Tesla |
| 787,412 A | 4/1905 | Tesla |
| 1,039,354 A | 9/1912 | Bonadio |
| 1,127,948 A | 2/1915 | Wappler |
| 1,482,653 A | 2/1924 | Lilly |
| 1,625,602 A | 4/1927 | Gould et al. |
| 1,916,722 A | 7/1933 | Ende |
| 2,028,635 A | 1/1936 | Wappler |
| 2,031,682 A | 2/1936 | Wappler et al. |
| 2,113,246 A | 4/1938 | Wappler |
| 2,155,365 A | 4/1939 | Rankin |
| 2,191,858 A | 2/1940 | Moore |
| 2,196,620 A | 4/1940 | Attarian |
| 2,388,137 A | 10/1945 | Graumlich |
| 2,493,108 A | 1/1950 | Casey, Jr. |
| 2,504,152 A | 4/1950 | Riker et al. |
| 2,938,382 A | 5/1960 | De Graaf |
| 2,952,206 A | 9/1960 | Becksted |
| 3,069,195 A | 12/1962 | Buck |
| 3,070,088 A * | 12/1962 | Brahos .......................... 600/234 |
| 3,170,471 A | 2/1965 | Schnitzer |
| 3,435,824 A | 4/1969 | Gamponia |
| 3,470,876 A | 10/1969 | Barchilon |
| 3,595,239 A | 7/1971 | Petersen |

(Continued)

FOREIGN PATENT DOCUMENTS

| | | |
|---|---|---|
| AU | 666310 B2 | 2/1996 |
| DE | 3008120 A1 | 9/1980 |

(Continued)

OTHER PUBLICATIONS

International Search Report and Written Opinion for PCT/US2010/055257, May 25, 2011 (18 pages).

(Continued)

*Primary Examiner* — Eduardo C Robert
*Assistant Examiner* — James Palmer

(57) ABSTRACT

A surgical method, system, kit, and various devices are provided for use in, among other things, vaginal entry during a natural orifice translumenal endoscopic surgical procedure. A system and/or method provide for the rapid creation of a conduit and/or multiple ports in a natural orifice, such as a patient's vagina, while accommodating anatomical variation to reduce the need to excise additional tissue from the patient.

15 Claims, 37 Drawing Sheets

(56) References Cited

U.S. PATENT DOCUMENTS

| | | | |
|---|---|---|---|
| 3,669,487 A | 6/1972 | Roberts et al. | |
| 3,746,881 A | 7/1973 | Fitch et al. | |
| 3,799,672 A | 3/1974 | Vurek | |
| 3,854,473 A | 12/1974 | Matsuo | |
| 3,946,740 A | 3/1976 | Bassett | |
| 3,948,251 A | 4/1976 | Hosono | |
| 3,961,632 A | 6/1976 | Moossun | |
| 3,965,890 A * | 6/1976 | Gauthier | 600/215 |
| 3,994,301 A | 11/1976 | Agris | |
| 4,011,872 A | 3/1977 | Komiya | |
| 4,012,812 A | 3/1977 | Black | |
| 4,085,743 A | 4/1978 | Yoon | |
| 4,164,225 A | 8/1979 | Johnson et al. | |
| 4,174,715 A | 11/1979 | Hasson | |
| 4,178,920 A | 12/1979 | Cawood, Jr. et al. | |
| 4,207,873 A | 6/1980 | Kruy | |
| 4,235,238 A | 11/1980 | Ogiu et al. | |
| 4,258,716 A | 3/1981 | Sutherland | |
| 4,269,174 A | 5/1981 | Adair | |
| 4,278,077 A | 7/1981 | Mizumoto | |
| 4,285,344 A | 8/1981 | Marshall | |
| 4,311,143 A | 1/1982 | Komiya | |
| 4,329,980 A | 5/1982 | Terada | |
| 4,396,021 A | 8/1983 | Baumgartner | |
| 4,406,656 A | 9/1983 | Hattler et al. | |
| 4,452,246 A | 6/1984 | Bader et al. | |
| 4,461,281 A | 7/1984 | Carson | |
| 4,491,132 A | 1/1985 | Aikins | |
| 4,527,331 A | 7/1985 | Lasner et al. | |
| 4,527,564 A | 7/1985 | Eguchi et al. | |
| 4,538,594 A | 9/1985 | Boebel et al. | |
| D281,104 S | 10/1985 | Davison | |
| 4,569,347 A | 2/1986 | Frisbie | |
| 4,580,551 A | 4/1986 | Siegmund et al. | |
| 4,646,722 A | 3/1987 | Silverstein et al. | |
| 4,653,476 A | 3/1987 | Bonnet | |
| 4,655,219 A | 4/1987 | Petruzzi | |
| 4,669,470 A | 6/1987 | Brandfield | |
| 4,671,477 A | 6/1987 | Cullen | |
| 4,677,982 A | 7/1987 | Llinas et al. | |
| 4,685,447 A | 8/1987 | Iversen et al. | |
| 4,711,240 A | 12/1987 | Goldwasser et al. | |
| 4,712,545 A | 12/1987 | Honkanen | |
| 4,721,116 A | 1/1988 | Schintgen et al. | |
| 4,727,600 A | 2/1988 | Avakian | |
| 4,733,662 A | 3/1988 | DeSatnick et al. | |
| D295,894 S | 5/1988 | Sharkany et al. | |
| 4,763,669 A | 8/1988 | Jaeger | |
| 4,770,188 A | 9/1988 | Chikama | |
| 4,815,450 A | 3/1989 | Patel | |
| 4,823,794 A | 4/1989 | Pierce | |
| 4,829,999 A | 5/1989 | Auth | |
| 4,867,140 A | 9/1989 | Hovis et al. | |
| 4,869,238 A | 9/1989 | Opie et al. | |
| 4,869,459 A | 9/1989 | Bourne | |
| 4,873,979 A | 10/1989 | Hanna | |
| 4,880,015 A | 11/1989 | Nierman | |
| 4,911,148 A | 3/1990 | Sosnowski et al. | |
| 4,926,860 A | 5/1990 | Stice et al. | |
| 4,938,214 A | 7/1990 | Specht et al. | |
| 4,950,273 A | 8/1990 | Briggs | |
| 4,950,285 A | 8/1990 | Wilk | |
| 4,953,539 A | 9/1990 | Nakamura et al. | |
| 4,960,133 A | 10/1990 | Hewson | |
| 4,977,887 A | 12/1990 | Gouda | |
| 4,979,950 A | 12/1990 | Transue et al. | |
| 4,984,581 A | 1/1991 | Stice | |
| 4,994,079 A | 2/1991 | Genese et al. | |
| 5,007,917 A | 4/1991 | Evans | |
| 5,010,876 A | 4/1991 | Henley et al. | |
| 5,020,514 A | 6/1991 | Heckele | |
| 5,020,535 A | 6/1991 | Parker et al. | |
| 5,025,778 A | 6/1991 | Silverstein et al. | |
| 5,033,169 A | 7/1991 | Bindon | |
| 5,037,433 A | 8/1991 | Wilk et al. | |
| 5,041,129 A | 8/1991 | Hayhurst et al. | |
| 5,046,513 A | 9/1991 | Gatturna et al. | |
| 5,050,585 A | 9/1991 | Takahashi | |
| 5,052,372 A | 10/1991 | Shapiro | |
| 5,065,516 A | 11/1991 | Dulebohn | |
| 5,066,295 A | 11/1991 | Kozak et al. | |
| 5,108,421 A | 4/1992 | Fowler | |
| 5,123,913 A | 6/1992 | Wilk et al. | |
| 5,123,914 A | 6/1992 | Cope | |
| 5,133,727 A | 7/1992 | Bales et al. | |
| 5,147,374 A | 9/1992 | Fernandez | |
| 5,174,300 A | 12/1992 | Bales et al. | |
| 5,176,126 A | 1/1993 | Chikama | |
| 5,190,050 A | 3/1993 | Nitzsche | |
| 5,190,555 A | 3/1993 | Wetter et al. | |
| 5,192,284 A | 3/1993 | Pleatman | |
| 5,192,300 A | 3/1993 | Fowler | |
| 5,197,963 A | 3/1993 | Parins | |
| 5,201,752 A | 4/1993 | Brown et al. | |
| 5,201,908 A | 4/1993 | Jones | |
| 5,203,785 A | 4/1993 | Slater | |
| 5,203,787 A | 4/1993 | Noblitt et al. | |
| 5,209,747 A | 5/1993 | Knoepfler | |
| 5,217,003 A | 6/1993 | Wilk | |
| 5,217,453 A | 6/1993 | Wilk | |
| 5,219,357 A | 6/1993 | Honkanen et al. | |
| 5,219,358 A | 6/1993 | Bendel et al. | |
| 5,222,362 A | 6/1993 | Maus et al. | |
| 5,222,965 A | 6/1993 | Haughton | |
| 5,234,437 A | 8/1993 | Sepetka | |
| 5,234,453 A | 8/1993 | Smith et al. | |
| 5,235,964 A | 8/1993 | Abenaim | |
| 5,242,456 A | 9/1993 | Nash et al. | |
| 5,245,460 A | 9/1993 | Allen et al. | |
| 5,246,424 A | 9/1993 | Wilk | |
| 5,257,999 A | 11/1993 | Slanetz, Jr. | |
| 5,259,366 A | 11/1993 | Reydel et al. | |
| 5,263,958 A | 11/1993 | deGuillebon et al. | |
| 5,273,524 A | 12/1993 | Fox et al. | |
| 5,275,607 A | 1/1994 | Lo et al. | |
| 5,275,614 A | 1/1994 | Haber et al. | |
| 5,275,616 A | 1/1994 | Fowler | |
| 5,284,128 A | 2/1994 | Hart | |
| 5,284,162 A | 2/1994 | Wilk | |
| 5,287,845 A | 2/1994 | Faul et al. | |
| 5,287,852 A | 2/1994 | Arkinstall | |
| 5,290,299 A | 3/1994 | Fain et al. | |
| 5,290,302 A | 3/1994 | Pericic | |
| 5,295,977 A | 3/1994 | Cohen et al. | |
| 5,297,536 A | 3/1994 | Wilk | |
| 5,297,687 A | 3/1994 | Freed | |
| 5,301,061 A | 4/1994 | Nakada et al. | |
| 5,312,023 A | 5/1994 | Green et al. | |
| 5,312,333 A | 5/1994 | Churinetz et al. | |
| 5,312,351 A | 5/1994 | Gerrone | |
| 5,312,416 A | 5/1994 | Spaeth et al. | |
| 5,312,423 A | 5/1994 | Rosenbluth et al. | |
| 5,318,589 A | 6/1994 | Lichtman | |
| 5,320,636 A | 6/1994 | Slater | |
| 5,324,261 A | 6/1994 | Amundson et al. | |
| 5,325,845 A | 7/1994 | Adair | |
| 5,330,471 A | 7/1994 | Eggers | |
| 5,330,486 A | 7/1994 | Wilk | |
| 5,330,488 A | 7/1994 | Goldrath | |
| 5,330,496 A | 7/1994 | Alferness | |
| 5,330,502 A | 7/1994 | Hassler et al. | |
| 5,331,971 A | 7/1994 | Bales et al. | |
| 5,334,168 A | 8/1994 | Hemmer | |
| 5,334,198 A | 8/1994 | Hart et al. | |
| 5,341,815 A | 8/1994 | Cofone et al. | |
| 5,342,396 A | 8/1994 | Cook | |
| 5,344,428 A | 9/1994 | Griffiths | |
| 5,345,927 A * | 9/1994 | Bonutti | 600/207 |
| 5,350,391 A | 9/1994 | Iacovelli | |
| 5,352,184 A | 10/1994 | Goldberg et al. | |
| 5,352,222 A | 10/1994 | Rydell | |
| 5,354,302 A | 10/1994 | Ko | |
| 5,354,311 A | 10/1994 | Kambin et al. | |
| 5,356,381 A | 10/1994 | Ensminger et al. | |

(56) References Cited

U.S. PATENT DOCUMENTS

| | | | |
|---|---|---|---|
| 5,356,408 A | 10/1994 | Rydell | |
| 5,360,428 A | 11/1994 | Hutchinson, Jr. | |
| 5,364,408 A | 11/1994 | Gordon | |
| 5,364,410 A | 11/1994 | Failla et al. | |
| 5,366,466 A | 11/1994 | Christian et al. | |
| 5,366,467 A | 11/1994 | Lynch et al. | |
| 5,368,605 A | 11/1994 | Miller, Jr. | |
| 5,370,647 A | 12/1994 | Graber et al. | |
| 5,370,679 A | 12/1994 | Atlee, III | |
| 5,374,273 A | 12/1994 | Nakao et al. | |
| 5,374,275 A | 12/1994 | Bradley et al. | |
| 5,374,277 A | 12/1994 | Hassler | |
| 5,377,695 A | 1/1995 | An Haack | |
| 5,383,877 A | 1/1995 | Clarke | |
| 5,383,888 A | 1/1995 | Zvenyatsky et al. | |
| 5,386,817 A | 2/1995 | Jones | |
| 5,387,259 A | 2/1995 | Davidson | |
| 5,391,174 A | 2/1995 | Weston | |
| 5,392,789 A | 2/1995 | Slater et al. | |
| 5,395,386 A | 3/1995 | Slater | |
| 5,401,248 A | 3/1995 | Bencini | |
| 5,403,311 A | 4/1995 | Abele et al. | |
| 5,403,328 A | 4/1995 | Shallman | |
| 5,403,342 A | 4/1995 | Tovey et al. | |
| 5,403,348 A | 4/1995 | Bonutti | |
| 5,405,073 A | 4/1995 | Porter | |
| 5,405,359 A | 4/1995 | Pierce | |
| 5,409,478 A | 4/1995 | Gerry et al. | |
| 5,417,699 A | 5/1995 | Klein et al. | |
| 5,423,821 A | 6/1995 | Pasque | |
| 5,433,721 A | 7/1995 | Hooven et al. | |
| 5,439,471 A | 8/1995 | Kerr | |
| 5,439,478 A | 8/1995 | Palmer | |
| 5,441,059 A | 8/1995 | Dannan | |
| 5,441,494 A | 8/1995 | Ortiz | |
| 5,441,499 A | 8/1995 | Fritzsch | |
| 5,443,463 A | 8/1995 | Stern et al. | |
| 5,445,638 A | 8/1995 | Rydell et al. | |
| 5,445,648 A | 8/1995 | Cook | |
| 5,449,021 A | 9/1995 | Chikama | |
| 5,454,827 A | 10/1995 | Aust et al. | |
| 5,456,667 A | 10/1995 | Ham et al. | |
| 5,456,684 A | 10/1995 | Schmidt et al. | |
| 5,458,131 A | 10/1995 | Wilk | |
| 5,458,583 A | 10/1995 | McNeely et al. | |
| 5,460,168 A | 10/1995 | Masubuchi et al. | |
| 5,460,629 A | 10/1995 | Shlain et al. | |
| 5,462,561 A | 10/1995 | Voda | |
| 5,465,731 A | 11/1995 | Bell et al. | |
| 5,467,763 A | 11/1995 | McMahon et al. | |
| 5,468,250 A | 11/1995 | Paraschac et al. | |
| 5,470,308 A | 11/1995 | Edwards et al. | |
| 5,470,320 A | 11/1995 | Tiefenbrun et al. | |
| 5,478,347 A | 12/1995 | Aranyi | |
| 5,478,352 A | 12/1995 | Fowler | |
| 5,480,404 A | 1/1996 | Kammerer et al. | |
| 5,482,054 A | 1/1996 | Slater et al. | |
| 5,484,451 A | 1/1996 | Akopov et al. | |
| 5,489,256 A | 2/1996 | Adair | |
| 5,496,347 A | 3/1996 | Hashiguchi et al. | |
| 5,499,990 A | 3/1996 | Schülken et al. | |
| 5,499,992 A | 3/1996 | Meade et al. | |
| 5,501,692 A | 3/1996 | Riza | |
| 5,503,616 A | 4/1996 | Jones | |
| 5,505,686 A | 4/1996 | Willis et al. | |
| 5,507,755 A | 4/1996 | Gresl et al. | |
| 5,511,564 A | 4/1996 | Wilk | |
| 5,514,157 A | 5/1996 | Nicholas et al. | |
| 5,518,501 A | 5/1996 | Oneda et al. | |
| 5,522,829 A | 6/1996 | Michalos | |
| 5,522,830 A | 6/1996 | Aranyi | |
| 5,527,321 A | 6/1996 | Hinchliffe | |
| 5,533,418 A | 7/1996 | Wu et al. | |
| 5,536,248 A | 7/1996 | Weaver et al. | |
| 5,538,509 A | 7/1996 | Dunlap et al. | |
| 5,540,648 A | 7/1996 | Yoon | |
| 5,549,637 A | 8/1996 | Crainich | |
| 5,554,151 A | 9/1996 | Hinchliffe | |
| 5,555,883 A | 9/1996 | Avitall | |
| 5,558,133 A | 9/1996 | Bortoli et al. | |
| 5,562,693 A | 10/1996 | Devlin et al. | |
| 5,569,243 A | 10/1996 | Kortenbach et al. | |
| 5,569,298 A | 10/1996 | Schnell | |
| 5,571,090 A | 11/1996 | Sherts | |
| 5,573,540 A | 11/1996 | Yoon | |
| 5,578,030 A | 11/1996 | Levin | |
| 5,582,611 A | 12/1996 | Tsuruta et al. | |
| 5,582,617 A | 12/1996 | Klieman et al. | |
| 5,584,845 A | 12/1996 | Hart | |
| 5,591,179 A | 1/1997 | Edelstein | |
| 5,591,205 A | 1/1997 | Fowler | |
| 5,593,420 A | 1/1997 | Eubanks, Jr. et al. | |
| 5,595,562 A | 1/1997 | Grier | |
| 5,597,378 A | 1/1997 | Jervis | |
| 5,601,573 A | 2/1997 | Fogelberg et al. | |
| 5,601,588 A | 2/1997 | Tonomura et al. | |
| 5,601,602 A | 2/1997 | Fowler | |
| 5,604,531 A | 2/1997 | Iddan et al. | |
| 5,607,389 A | 3/1997 | Edwards et al. | |
| 5,607,406 A | 3/1997 | Hernandez et al. | |
| 5,607,450 A | 3/1997 | Zvenyatsky et al. | |
| 5,609,601 A | 3/1997 | Kolesa et al. | |
| 5,613,975 A | 3/1997 | Christy | |
| 5,616,117 A * | 4/1997 | Dinkler et al. | 600/232 |
| 5,618,303 A | 4/1997 | Marlow et al. | |
| 5,620,415 A | 4/1997 | Lucey et al. | |
| 5,624,399 A | 4/1997 | Ackerman | |
| 5,624,431 A | 4/1997 | Gerry et al. | |
| 5,626,578 A | 5/1997 | Tihon | |
| 5,628,732 A | 5/1997 | Antoon, Jr. et al. | |
| 5,630,782 A | 5/1997 | Adair | |
| 5,643,283 A | 7/1997 | Younker | |
| 5,643,292 A | 7/1997 | Hart | |
| 5,643,294 A | 7/1997 | Tovey et al. | |
| 5,644,798 A | 7/1997 | Shah | |
| 5,645,083 A | 7/1997 | Essig et al. | |
| 5,645,565 A | 7/1997 | Rudd et al. | |
| 5,649,372 A | 7/1997 | Souza | |
| 5,653,677 A | 8/1997 | Okada et al. | |
| 5,653,690 A | 8/1997 | Booth et al. | |
| 5,653,722 A | 8/1997 | Kieturakis | |
| 5,657,755 A | 8/1997 | Desai | |
| 5,662,621 A | 9/1997 | Lafontaine | |
| 5,662,663 A | 9/1997 | Shallman | |
| 5,667,527 A | 9/1997 | Cook | |
| 5,669,875 A | 9/1997 | van Eerdenburg | |
| 5,681,324 A | 10/1997 | Kammerer et al. | |
| 5,681,330 A | 10/1997 | Hughett et al. | |
| 5,685,820 A | 11/1997 | Riek et al. | |
| 5,690,606 A | 11/1997 | Slotman | |
| 5,690,656 A | 11/1997 | Cope et al. | |
| 5,690,660 A | 11/1997 | Kauker et al. | |
| 5,695,448 A | 12/1997 | Kimura et al. | |
| 5,695,505 A | 12/1997 | Yoon | |
| 5,695,511 A | 12/1997 | Cano et al. | |
| 5,700,275 A | 12/1997 | Bell et al. | |
| 5,702,438 A | 12/1997 | Avitall | |
| 5,704,892 A | 1/1998 | Adair | |
| 5,709,708 A | 1/1998 | Thal | |
| 5,711,921 A | 1/1998 | Langford | |
| 5,716,326 A | 2/1998 | Dannan | |
| 5,716,375 A | 2/1998 | Fowler | |
| 5,728,094 A | 3/1998 | Edwards | |
| 5,730,740 A | 3/1998 | Wales et al. | |
| 5,735,849 A | 4/1998 | Baden et al. | |
| 5,741,234 A | 4/1998 | Aboul-Hosn | |
| 5,741,278 A | 4/1998 | Stevens | |
| 5,741,285 A | 4/1998 | McBrayer et al. | |
| 5,741,429 A | 4/1998 | Donadio, III et al. | |
| 5,743,456 A | 4/1998 | Jones et al. | |
| 5,746,759 A | 5/1998 | Meade et al. | |
| 5,749,826 A | 5/1998 | Faulkner | |
| 5,749,881 A | 5/1998 | Sackier et al. | |
| 5,749,889 A | 5/1998 | Bacich et al. | |

(56) References Cited

U.S. PATENT DOCUMENTS

| | | |
|---|---|---|
| 5,752,951 A | 5/1998 | Yanik |
| 5,755,731 A | 5/1998 | Grinberg |
| 5,762,604 A | 6/1998 | Kieturakis |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,797,959 A | 8/1998 | Castro et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A * | 10/1998 | Yoon et al. .............. 600/207 |
| 5,824,071 A | 10/1998 | Nelson et al. |
| 5,827,276 A | 10/1998 | LeVeen et al. |
| 5,827,281 A | 10/1998 | Levin |
| 5,827,299 A | 10/1998 | Thomason et al. |
| 5,827,323 A | 10/1998 | Klieman et al. |
| 5,830,231 A | 11/1998 | Geiges, Jr. |
| 5,833,603 A | 11/1998 | Kovacs et al. |
| 5,833,700 A | 11/1998 | Fogelberg et al. |
| 5,833,703 A | 11/1998 | Manushakian |
| 5,836,960 A | 11/1998 | Kolesa et al. |
| 5,843,017 A | 12/1998 | Yoon |
| 5,843,121 A | 12/1998 | Yoon |
| 5,849,022 A | 12/1998 | Sakashita et al. |
| 5,853,374 A | 12/1998 | Hart et al. |
| 5,855,585 A | 1/1999 | Kontos |
| 5,860,913 A | 1/1999 | Yamaya et al. |
| 5,860,995 A | 1/1999 | Berkelaar |
| 5,868,762 A | 2/1999 | Cragg et al. |
| 5,876,411 A | 3/1999 | Kontos |
| 5,882,331 A | 3/1999 | Sasaki |
| 5,882,344 A | 3/1999 | Stouder, Jr. |
| 5,893,846 A | 4/1999 | Bales et al. |
| 5,893,874 A | 4/1999 | Bourque et al. |
| 5,893,875 A | 4/1999 | O'Connor et al. |
| 5,897,487 A | 4/1999 | Ouchi |
| 5,899,919 A | 5/1999 | Eubanks, Jr. et al. |
| 5,902,238 A | 5/1999 | Golden et al. |
| 5,902,254 A | 5/1999 | Magram |
| 5,904,702 A | 5/1999 | Ek et al. |
| 5,908,420 A | 6/1999 | Parins et al. |
| 5,908,429 A | 6/1999 | Yoon |
| 5,911,737 A | 6/1999 | Lee et al. |
| 5,916,146 A | 6/1999 | Allotta et al. |
| 5,916,147 A | 6/1999 | Boury |
| 5,921,993 A | 7/1999 | Yoon |
| 5,921,997 A | 7/1999 | Fogelberg et al. |
| 5,922,008 A | 7/1999 | Gimpelson |
| 5,925,052 A | 7/1999 | Simmons |
| 5,928,255 A | 7/1999 | Meade et al. |
| 5,928,266 A | 7/1999 | Kontos |
| 5,936,536 A | 8/1999 | Morris |
| 5,944,718 A | 8/1999 | Austin et al. |
| 5,951,547 A | 9/1999 | Gough et al. |
| 5,951,549 A | 9/1999 | Richardson et al. |
| 5,954,720 A | 9/1999 | Wilson et al. |
| 5,954,731 A | 9/1999 | Yoon |
| 5,957,936 A | 9/1999 | Yoon et al. |
| 5,957,943 A | 9/1999 | Vaitekunas |
| 5,957,953 A | 9/1999 | DiPoto et al. |
| 5,964,782 A | 10/1999 | Lafontaine et al. |
| 5,971,995 A | 10/1999 | Rousseau |
| 5,972,002 A | 10/1999 | Bark et al. |
| 5,976,074 A | 11/1999 | Moriyama |
| 5,976,075 A | 11/1999 | Beane et al. |
| 5,976,130 A | 11/1999 | McBrayer et al. |
| 5,976,131 A | 11/1999 | Guglielmi et al. |
| 5,980,539 A | 11/1999 | Kontos |
| 5,980,556 A | 11/1999 | Giordano et al. |
| 5,984,938 A | 11/1999 | Yoon |
| 5,984,939 A | 11/1999 | Yoon |
| 5,984,950 A | 11/1999 | Cragg et al. |
| 5,989,182 A | 11/1999 | Hori et al. |
| 5,993,447 A | 11/1999 | Blewett et al. |
| 5,993,474 A | 11/1999 | Ouchi |
| 5,995,875 A | 11/1999 | Blewett et al. |
| 5,997,555 A | 12/1999 | Kontos |
| 6,001,120 A | 12/1999 | Levin |
| 6,004,269 A | 12/1999 | Crowley et al. |
| 6,004,330 A | 12/1999 | Middleman et al. |
| 6,007,566 A | 12/1999 | Wenstrom, Jr. |
| 6,010,515 A | 1/2000 | Swain et al. |
| 6,012,494 A | 1/2000 | Balazs |
| 6,016,452 A | 1/2000 | Kasevich |
| 6,017,356 A | 1/2000 | Frederick et al. |
| 6,019,770 A | 2/2000 | Christoudias |
| 6,024,708 A | 2/2000 | Bales et al. |
| 6,024,747 A | 2/2000 | Kontos |
| 6,027,522 A | 2/2000 | Palmer |
| 6,030,365 A | 2/2000 | Laufer |
| 6,030,384 A | 2/2000 | Nezhat |
| 6,030,634 A | 2/2000 | Wu et al. |
| 6,033,399 A | 3/2000 | Gines |
| 6,036,640 A | 3/2000 | Corace et al. |
| 6,036,685 A | 3/2000 | Mueller |
| 6,053,927 A | 4/2000 | Hamas |
| 6,053,937 A | 4/2000 | Edwards et al. |
| 6,066,160 A | 5/2000 | Colvin et al. |
| 6,068,603 A | 5/2000 | Suzuki |
| 6,068,629 A | 5/2000 | Haissaguerre et al. |
| 6,071,233 A | 6/2000 | Ishikawa et al. |
| 6,074,408 A | 6/2000 | Freeman |
| 6,086,530 A | 7/2000 | Mack |
| 6,090,105 A | 7/2000 | Zepeda et al. |
| 6,090,108 A | 7/2000 | McBrayer et al. |
| 6,090,129 A | 7/2000 | Ouchi |
| 6,096,046 A | 8/2000 | Weiss |
| 6,102,909 A | 8/2000 | Chen et al. |
| 6,102,926 A | 8/2000 | Tartaglia et al. |
| 6,106,473 A | 8/2000 | Violante et al. |
| 6,106,521 A | 8/2000 | Blewett et al. |
| 6,109,852 A | 8/2000 | Shahinpoor et al. |
| 6,110,154 A | 8/2000 | Shimomura et al. |
| 6,110,183 A | 8/2000 | Cope |
| 6,113,593 A | 9/2000 | Tu et al. |
| 6,117,144 A | 9/2000 | Nobles et al. |
| 6,117,158 A | 9/2000 | Measamer et al. |
| 6,139,555 A | 10/2000 | Hart et al. |
| 6,141,037 A | 10/2000 | Upton et al. |
| 6,146,391 A | 11/2000 | Cigaina |
| 6,148,222 A | 11/2000 | Ramsey, III |
| 6,149,653 A | 11/2000 | Deslauriers |
| 6,149,662 A | 11/2000 | Pugliesi et al. |
| 6,152,920 A | 11/2000 | Thompson et al. |
| 6,156,006 A | 12/2000 | Brosens et al. |
| 6,159,200 A | 12/2000 | Verdura et al. |
| 6,165,175 A | 12/2000 | Wampler et al. |
| 6,165,184 A | 12/2000 | Verdura et al. |
| 6,168,570 B1 | 1/2001 | Ferrera |

(56) References Cited

U.S. PATENT DOCUMENTS

| | | | |
|---|---|---|---|
| 6,168,605 B1 | 1/2001 | Measamer et al. |
| 6,169,269 B1 | 1/2001 | Maynard |
| 6,170,130 B1 | 1/2001 | Hamilton et al. |
| 6,179,776 B1 | 1/2001 | Adams et al. |
| 6,179,832 B1 | 1/2001 | Jones et al. |
| 6,179,837 B1 | 1/2001 | Hooven |
| 6,183,420 B1 | 2/2001 | Douk et al. |
| 6,190,353 B1 | 2/2001 | Makower et al. |
| 6,190,383 B1 | 2/2001 | Schmaltz et al. |
| 6,190,384 B1 | 2/2001 | Ouchi |
| 6,190,399 B1 | 2/2001 | Palmer et al. |
| 6,203,533 B1 | 3/2001 | Ouchi |
| 6,206,872 B1 | 3/2001 | Lafond et al. |
| 6,206,877 B1 | 3/2001 | Kese et al. |
| 6,206,904 B1 | 3/2001 | Ouchi |
| 6,210,409 B1 | 4/2001 | Ellman et al. |
| 6,214,007 B1 | 4/2001 | Anderson |
| 6,214,028 B1 | 4/2001 | Yoon et al. |
| 6,216,043 B1 | 4/2001 | Swanson et al. |
| 6,228,096 B1 | 5/2001 | Marchand |
| 6,231,506 B1 * | 5/2001 | Hu et al. ..................... 600/210 |
| 6,234,958 B1 | 5/2001 | Snoke et al. |
| 6,245,079 B1 | 6/2001 | Nobles et al. |
| 6,246,914 B1 | 6/2001 | de la Rama et al. |
| 6,258,064 B1 | 7/2001 | Smith et al. |
| 6,261,242 B1 | 7/2001 | Roberts et al. |
| 6,264,664 B1 | 7/2001 | Avellanet |
| 6,270,497 B1 | 8/2001 | Sekino et al. |
| 6,270,505 B1 | 8/2001 | Yoshida et al. |
| 6,277,136 B1 | 8/2001 | Bonutti |
| 6,283,963 B1 | 9/2001 | Regula |
| 6,293,909 B1 | 9/2001 | Chu et al. |
| 6,293,952 B1 | 9/2001 | Brosens et al. |
| 6,296,630 B1 | 10/2001 | Altman et al. |
| 6,314,963 B1 | 11/2001 | Vaska et al. |
| 6,322,578 B1 | 11/2001 | Houle et al. |
| 6,325,534 B1 | 12/2001 | Hawley et al. |
| 6,326,177 B1 | 12/2001 | Schoenbach et al. |
| 6,328,730 B1 | 12/2001 | Harkrider, Jr. |
| 6,350,267 B1 | 2/2002 | Stefanchik |
| 6,350,278 B1 | 2/2002 | Lenker et al. |
| 6,352,503 B1 | 3/2002 | Matsui et al. |
| 6,352,543 B1 | 3/2002 | Cole |
| 6,355,013 B1 | 3/2002 | van Muiden |
| 6,355,035 B1 | 3/2002 | Manushakian |
| 6,361,534 B1 | 3/2002 | Chen et al. |
| 6,364,879 B1 | 4/2002 | Chen et al. |
| 6,368,340 B2 | 4/2002 | Malecki et al. |
| 6,371,956 B1 | 4/2002 | Wilson et al. |
| 6,379,366 B1 | 4/2002 | Fleischman et al. |
| 6,383,195 B1 | 5/2002 | Richard |
| 6,383,197 B1 | 5/2002 | Conlon et al. |
| 6,387,671 B1 | 5/2002 | Rubinsky et al. |
| 6,391,029 B1 | 5/2002 | Hooven et al. |
| 6,398,708 B1 | 6/2002 | Hastings et al. |
| 6,402,735 B1 | 6/2002 | Langevin |
| 6,402,746 B1 | 6/2002 | Whayne et al. |
| 6,406,440 B1 | 6/2002 | Stefanchik |
| 6,409,727 B1 | 6/2002 | Bales et al. |
| 6,409,733 B1 | 6/2002 | Conlon et al. |
| 6,419,639 B2 | 7/2002 | Walther et al. |
| 6,419,641 B1 | 7/2002 | Mark et al. |
| 6,427,089 B1 | 7/2002 | Knowlton |
| 6,431,500 B1 | 8/2002 | Jacobs et al. |
| 6,436,107 B1 | 8/2002 | Wang et al. |
| 6,443,970 B1 | 9/2002 | Schulze et al. |
| 6,443,988 B2 | 9/2002 | Felt et al. |
| 6,447,511 B1 | 9/2002 | Slater |
| 6,447,523 B1 | 9/2002 | Middleman et al. |
| 6,454,783 B1 | 9/2002 | Piskun |
| 6,454,785 B2 | 9/2002 | De Hoyos Garza |
| 6,458,076 B1 | 10/2002 | Pruitt |
| 6,464,701 B1 | 10/2002 | Hooven et al. |
| 6,464,702 B2 | 10/2002 | Schulze et al. |
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,526,320 B2 | 2/2003 | Mitchell |
| 6,527,782 B2 | 3/2003 | Hogg et al. |
| 6,530,922 B2 | 3/2003 | Cosman et al. |
| 6,535,764 B2 | 3/2003 | Imran et al. |
| 6,537,200 B2 | 3/2003 | Leysieffer et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,823 B2 * | 4/2003 | Palmer et al. ..................... 606/1 |
| 6,554,829 B2 | 4/2003 | Schulze et al. |
| 6,558,384 B2 | 5/2003 | Mayenberger |
| 6,562,034 B2 | 5/2003 | Edwards et al. |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,613,038 B2 | 9/2003 | Bonutti et al. |
| 6,613,068 B2 | 9/2003 | Ouchi |
| 6,616,632 B2 | 9/2003 | Sharp et al. |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,275 B1 | 10/2003 | McGaffigan et al. |
| 6,638,286 B1 | 10/2003 | Burbank et al. |
| 6,645,225 B1 | 11/2003 | Atkinson |
| 6,652,518 B2 | 11/2003 | Wellman et al. |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,673,092 B1 | 1/2004 | Bacher |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,692,493 B2 | 2/2004 | McGovern et al. |
| 6,699,180 B2 | 3/2004 | Kobayashi |
| 6,699,256 B2 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,188 B2 | 3/2004 | Ushimaru |
| 6,709,445 B2 | 3/2004 | Boebel et al. |
| 6,716,226 B2 | 4/2004 | Sixto, Jr. et al. |
| 6,731,875 B1 | 5/2004 | Kartalopoulos |

(56) References Cited

U.S. PATENT DOCUMENTS

| | | |
|---|---|---|
| 6,736,822 B2 | 5/2004 | McClellan et al. |
| 6,740,030 B2 | 5/2004 | Martone et al. |
| 6,743,166 B2 | 6/2004 | Berci et al. |
| 6,743,226 B2 | 6/2004 | Cosman et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,761,722 B2 | 7/2004 | Cole et al. |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,382 B1 | 9/2004 | Hoffman |
| 6,786,864 B2 | 9/2004 | Matsuura et al. |
| 6,786,905 B2 | 9/2004 | Swanson et al. |
| 6,788,977 B2 | 9/2004 | Fenn et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,818,007 B1 | 11/2004 | Dampney et al. |
| 6,824,548 B2 | 11/2004 | Smith et al. |
| 6,830,545 B2 | 12/2004 | Bendall |
| 6,836,688 B2 | 12/2004 | Ingle et al. |
| 6,837,847 B2 | 1/2005 | Ewers et al. |
| 6,840,246 B2 | 1/2005 | Downing |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,213 B2 | 4/2005 | Ryan et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,899,710 B2 | 5/2005 | Hooven |
| 6,908,427 B2 | 6/2005 | Fleener et al. |
| 6,908,476 B2 | 6/2005 | Jud et al. |
| 6,913,613 B2 | 7/2005 | Schwarz et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,932,834 B2 | 8/2005 | Lizardi et al. |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,955,683 B2 | 10/2005 | Bonutti |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,008,419 B2 | 3/2006 | Shadduck |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |
| 7,060,024 B2 | 6/2006 | Long et al. |
| 7,060,025 B2 | 6/2006 | Long et al. |
| 7,063,697 B2 | 6/2006 | Slater |
| 7,063,715 B2 | 6/2006 | Onuki et al. |
| 7,066,879 B2 | 6/2006 | Fowler et al. |
| 7,066,936 B2 | 6/2006 | Ryan |
| 7,070,602 B2 | 7/2006 | Smith et al. |
| 7,076,305 B2 | 7/2006 | Imran et al. |
| 7,083,618 B2 | 8/2006 | Couture et al. |
| 7,083,620 B2 | 8/2006 | Jahns et al. |
| 7,083,629 B2 | 8/2006 | Weller et al. |
| 7,083,635 B2 | 8/2006 | Ginn |
| 7,087,071 B2 | 8/2006 | Nicholas et al. |
| 7,088,923 B2 | 8/2006 | Haruyama |
| 7,090,673 B2 | 8/2006 | Dycus et al. |
| 7,090,683 B2 | 8/2006 | Brock et al. |
| 7,090,685 B2 | 8/2006 | Kortenbach et al. |
| 7,093,518 B2 | 8/2006 | Gmeilbauer |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,105,000 B2 | 9/2006 | McBrayer |
| 7,105,005 B2 | 9/2006 | Blake |
| 7,108,696 B2 | 9/2006 | Daniel et al. |
| 7,108,703 B2 | 9/2006 | Danitz et al. |
| 7,112,208 B2 | 9/2006 | Morris et al. |
| 7,115,092 B2 | 10/2006 | Park et al. |
| 7,115,124 B1 | 10/2006 | Xiao |
| 7,117,703 B2 | 10/2006 | Kato et al. |
| 7,118,531 B2 | 10/2006 | Krill |
| 7,118,578 B2 | 10/2006 | West, Jr. et al. |
| 7,118,587 B2 | 10/2006 | Dycus et al. |
| 7,128,708 B2 | 10/2006 | Saadat et al. |
| 7,130,697 B2 | 10/2006 | Chornenky et al. |
| RE39,415 E | 11/2006 | Bales et al. |
| 7,131,978 B2 | 11/2006 | Sancoff et al. |
| 7,131,979 B2 | 11/2006 | DiCarlo et al. |
| 7,131,980 B1 | 11/2006 | Field et al. |
| 7,137,980 B2 | 11/2006 | Buysse et al. |
| 7,137,981 B2 | 11/2006 | Long |
| 7,146,984 B2 | 12/2006 | Stack et al. |
| 7,147,650 B2 | 12/2006 | Lee |
| 7,150,097 B2 | 12/2006 | Sremcich et al. |
| 7,150,655 B2 | 12/2006 | Mastrototaro et al. |
| 7,150,750 B2 | 12/2006 | Damarati |
| 7,152,488 B2 | 12/2006 | Hedrich et al. |
| 7,153,321 B2 | 12/2006 | Andrews |

(56) References Cited

U.S. PATENT DOCUMENTS

| | | |
|---|---|---|
| 7,160,296 B2 | 1/2007 | Pearson et al. |
| 7,163,525 B2 | 1/2007 | Franer |
| 7,172,714 B2 | 2/2007 | Jacobson |
| 7,179,254 B2 | 2/2007 | Pendekanti et al. |
| 7,188,627 B2 | 3/2007 | Nelson et al. |
| 7,195,612 B2 | 3/2007 | Van Sloten et al. |
| 7,195,631 B2 | 3/2007 | Dumbauld |
| 7,204,820 B2 | 4/2007 | Akahoshi |
| 7,208,005 B2 | 4/2007 | Frecker et al. |
| 7,211,092 B2 | 5/2007 | Hughett |
| 7,220,227 B2 | 5/2007 | Sasaki et al. |
| 7,223,272 B2 | 5/2007 | Francere et al. |
| 7,229,438 B2 | 6/2007 | Young |
| 7,232,414 B2 | 6/2007 | Gonzalez |
| 7,232,445 B2 | 6/2007 | Kortenbach et al. |
| 7,235,089 B1 | 6/2007 | McGuckin, Jr. |
| 7,241,290 B2 | 7/2007 | Doyle et al. |
| 7,244,228 B2 | 7/2007 | Lubowski |
| 7,250,027 B2 | 7/2007 | Barry |
| 7,252,660 B2 | 8/2007 | Kunz |
| 7,255,675 B2 | 8/2007 | Gertner et al. |
| 7,261,725 B2 | 8/2007 | Binmoeller |
| 7,270,663 B2 | 9/2007 | Nakao |
| 7,291,127 B2 | 11/2007 | Eidenschink |
| 7,294,139 B1 | 11/2007 | Gengler |
| 7,301,250 B2 | 11/2007 | Cassel |
| 7,306,597 B2 | 12/2007 | Manzo |
| 7,308,828 B2 | 12/2007 | Hashimoto |
| 7,318,802 B2 | 1/2008 | Suzuki et al. |
| 7,320,695 B2 | 1/2008 | Carroll |
| 7,322,934 B2 | 1/2008 | Miyake et al. |
| 7,323,006 B2 | 1/2008 | Andreas et al. |
| 7,329,256 B2 | 2/2008 | Johnson et al. |
| 7,329,257 B2 | 2/2008 | Kanehira et al. |
| 7,329,383 B2 | 2/2008 | Stinson |
| 7,335,220 B2 | 2/2008 | Khosravi et al. |
| 7,344,536 B1 | 3/2008 | Lunsford et al. |
| 7,352,387 B2 | 4/2008 | Yamamoto |
| 7,364,582 B2 | 4/2008 | Lee |
| 7,371,215 B2 | 5/2008 | Colliou et al. |
| 7,381,216 B2 | 6/2008 | Buzzard et al. |
| 7,390,324 B2 | 6/2008 | Whalen et al. |
| 7,393,322 B2 | 7/2008 | Wenchell |
| 7,402,162 B2 | 7/2008 | Ouchi |
| 7,404,791 B2 | 7/2008 | Linares et al. |
| 7,410,483 B2 | 8/2008 | Danitz et al. |
| 7,413,563 B2 | 8/2008 | Corcoran et al. |
| 7,416,554 B2 | 8/2008 | Lam et al. |
| 7,422,590 B2 | 9/2008 | Kupferschmid et al. |
| 7,435,229 B2 | 10/2008 | Wolf |
| 7,435,257 B2 | 10/2008 | Lashinski et al. |
| 7,452,327 B2 | 11/2008 | Durgin et al. |
| 7,455,208 B2 | 11/2008 | Wales et al. |
| 7,468,066 B2 | 12/2008 | Vargas et al. |
| 7,476,237 B2 | 1/2009 | Taniguchi et al. |
| 7,485,093 B2 | 2/2009 | Glukhovsky |
| 7,488,295 B2 | 2/2009 | Burbank et al. |
| 7,494,499 B2 | 2/2009 | Nagase et al. |
| 7,497,867 B2 | 3/2009 | Lasner et al. |
| 7,498,950 B1 | 3/2009 | Ertas et al. |
| 7,507,200 B2 | 3/2009 | Okada |
| 7,510,107 B2 | 3/2009 | Timm et al. |
| 7,511,733 B2 | 3/2009 | Takizawa et al. |
| 7,515,953 B2 | 4/2009 | Madar et al. |
| 7,520,876 B2 | 4/2009 | Ressemann et al. |
| 7,524,281 B2 | 4/2009 | Chu et al. |
| 7,524,302 B2 | 4/2009 | Tower |
| 7,534,228 B2 | 5/2009 | Williams |
| 7,540,872 B2 | 6/2009 | Schechter et al. |
| 7,542,807 B2 | 6/2009 | Bertolero et al. |
| 7,544,203 B2 | 6/2009 | Chin et al. |
| 7,548,040 B2 | 6/2009 | Lee et al. |
| 7,549,564 B2 | 6/2009 | Boudreaux |
| 7,549,998 B2 | 6/2009 | Braun |
| 7,553,278 B2 | 6/2009 | Kucklick |
| 7,553,298 B2 | 6/2009 | Hunt et al. |
| 7,559,452 B2 | 7/2009 | Wales et al. |
| 7,559,887 B2 | 7/2009 | Dannan |
| 7,559,916 B2 | 7/2009 | Smith et al. |
| 7,560,006 B2 | 7/2009 | Rakos et al. |
| 7,561,907 B2 | 7/2009 | Fuimaono et al. |
| 7,561,916 B2 | 7/2009 | Hunt et al. |
| 7,566,334 B2 | 7/2009 | Christian et al. |
| 7,575,144 B2 | 8/2009 | Ortiz et al. |
| 7,575,548 B2 | 8/2009 | Takemoto et al. |
| 7,579,550 B2 | 8/2009 | Dayton et al. |
| 7,582,096 B2 | 9/2009 | Gellman et al. |
| 7,588,177 B2 | 9/2009 | Racenet |
| 7,588,557 B2 | 9/2009 | Nakao |
| 7,597,229 B2 | 10/2009 | Boudreaux et al. |
| 7,604,150 B2 | 10/2009 | Boudreaux |
| 7,608,083 B2 | 10/2009 | Lee et al. |
| 7,611,479 B2 | 11/2009 | Cragg et al. |
| 7,618,398 B2 | 11/2009 | Holman et al. |
| 7,621,936 B2 | 11/2009 | Cragg et al. |
| 7,632,250 B2 | 12/2009 | Smith et al. |
| 7,635,373 B2 | 12/2009 | Ortiz |
| 7,637,903 B2 | 12/2009 | Lentz et al. |
| 7,648,519 B2 | 1/2010 | Lee et al. |
| 7,650,742 B2 | 1/2010 | Ushijima |
| 7,651,483 B2 | 1/2010 | Byrum et al. |
| 7,651,509 B2 | 1/2010 | Bojarski et al. |
| 7,654,431 B2 | 2/2010 | Hueil et al. |
| 7,655,004 B2 | 2/2010 | Long |
| 7,662,089 B2 | 2/2010 | Okada et al. |
| 7,666,180 B2 | 2/2010 | Holsten et al. |
| 7,666,203 B2 | 2/2010 | Chanduszko et al. |
| 7,670,336 B2 | 3/2010 | Young et al. |
| 7,674,259 B2 | 3/2010 | Shadduck |
| 7,678,043 B2 | 3/2010 | Gilad |
| 7,680,543 B2 | 3/2010 | Azure |
| 7,684,599 B2 | 3/2010 | Horn et al. |
| 7,686,826 B2 | 3/2010 | Lee et al. |
| 7,697,970 B2 | 4/2010 | Uchiyama et al. |
| 7,699,835 B2 | 4/2010 | Lee et al. |
| 7,713,189 B2 | 5/2010 | Hanke |
| 7,713,270 B2 | 5/2010 | Suzuki |
| 7,736,374 B2 | 6/2010 | Vaughan et al. |
| 7,744,615 B2 | 6/2010 | Couture |
| 7,749,161 B2 | 7/2010 | Beckman et al. |
| 7,753,933 B2 | 7/2010 | Ginn et al. |
| 7,758,577 B2 | 7/2010 | Nobis et al. |
| 7,762,949 B2 | 7/2010 | Nakao |
| 7,762,998 B2 | 7/2010 | Birk et al. |
| 7,763,012 B2 | 7/2010 | Petrick et al. |
| 7,765,010 B2 | 7/2010 | Chornenky et al. |
| 7,771,416 B2 | 8/2010 | Spivey et al. |
| 7,771,437 B2 | 8/2010 | Hogg et al. |
| 7,780,683 B2 | 8/2010 | Roue et al. |
| 7,780,691 B2 | 8/2010 | Stefanchik |
| 7,784,663 B2 | 8/2010 | Shelton, IV |
| 7,794,409 B2 | 9/2010 | Damarati |
| 7,794,475 B2 | 9/2010 | Hess et al. |
| 7,798,386 B2 | 9/2010 | Schall et al. |
| 7,828,186 B2 | 11/2010 | Wales |
| 7,833,156 B2 | 11/2010 | Williams et al. |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,879,004 B2 | 2/2011 | Seibel et al. |
| 7,892,220 B2 | 2/2011 | Faller et al. |
| 7,896,804 B2 | 3/2011 | Uchimura et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,927,271 B2 | 4/2011 | Dimitriou et al. |
| 7,931,624 B2 | 4/2011 | Smith et al. |

(56) References Cited

U.S. PATENT DOCUMENTS

| | | | |
|---|---|---|---|
| 7,945,332 B2 | 5/2011 | Schechter | |
| 7,947,000 B2 | 5/2011 | Vargas et al. | |
| 7,953,326 B2 | 5/2011 | Farr et al. | |
| 7,955,298 B2 | 6/2011 | Carroll et al. | |
| 7,963,975 B2 | 6/2011 | Criscuolo | |
| 7,965,180 B2 | 6/2011 | Koyama | |
| 7,967,808 B2 | 6/2011 | Fitzgerald et al. | |
| 7,969,473 B2 | 6/2011 | Kotoda | |
| 7,972,330 B2 | 7/2011 | Alejandro et al. | |
| 7,976,552 B2 | 7/2011 | Suzuki | |
| 7,985,239 B2 | 7/2011 | Suzuki | |
| 7,988,685 B2 | 8/2011 | Ziaie et al. | |
| 8,034,046 B2 | 10/2011 | Eidenschink | |
| 8,048,067 B2 | 11/2011 | Davalos et al. | |
| 8,057,510 B2 | 11/2011 | Ginn et al. | |
| 8,062,311 B2 | 11/2011 | Litscher et al. | |
| 8,066,632 B2 | 11/2011 | Dario et al. | |
| 8,075,587 B2 | 12/2011 | Ginn | |
| 8,088,062 B2 | 1/2012 | Zwolinski | |
| 8,096,459 B2 | 1/2012 | Ortiz et al. | |
| 8,118,821 B2 | 2/2012 | Mouw | |
| 8,147,424 B2 | 4/2012 | Kassab et al. | |
| 8,157,813 B2 | 4/2012 | Ko et al. | |
| 8,182,414 B2 | 5/2012 | Handa et al. | |
| 8,206,295 B2 | 6/2012 | Kaul | |
| 8,221,310 B2 | 7/2012 | Saadat et al. | |
| 8,303,581 B2 | 11/2012 | Arts et al. | |
| 8,430,811 B2 | 4/2013 | Hess et al. | |
| 2001/0023333 A1 | 9/2001 | Wise et al. | |
| 2001/0029388 A1* | 10/2001 | Kieturakis et al. | 606/190 |
| 2001/0049497 A1 | 12/2001 | Kalloo et al. | |
| 2002/0022771 A1 | 2/2002 | Diokno et al. | |
| 2002/0022857 A1 | 2/2002 | Goldsteen et al. | |
| 2002/0023353 A1 | 2/2002 | Ting-Kung | |
| 2002/0029055 A1 | 3/2002 | Bonutti | |
| 2002/0042562 A1 | 4/2002 | Meron et al. | |
| 2002/0049439 A1 | 4/2002 | Mulier et al. | |
| 2002/0068945 A1 | 6/2002 | Sixto, Jr. et al. | |
| 2002/0078967 A1 | 6/2002 | Sixto, Jr. et al. | |
| 2002/0082516 A1 | 6/2002 | Stefanchik | |
| 2002/0095164 A1 | 7/2002 | Andreas et al. | |
| 2002/0107530 A1 | 8/2002 | Sauer et al. | |
| 2002/0133115 A1 | 9/2002 | Gordon et al. | |
| 2002/0138086 A1 | 9/2002 | Sixto, Jr. et al. | |
| 2002/0147456 A1 | 10/2002 | Diduch et al. | |
| 2002/0165592 A1 | 11/2002 | Glukhovsky et al. | |
| 2002/0173805 A1 | 11/2002 | Matsuno et al. | |
| 2002/0183591 A1 | 12/2002 | Matsuura et al. | |
| 2003/0014090 A1 | 1/2003 | Abrahamson | |
| 2003/0023255 A1 | 1/2003 | Miles et al. | |
| 2003/0036679 A1 | 2/2003 | Kortenbach et al. | |
| 2003/0069602 A1 | 4/2003 | Jacobs et al. | |
| 2003/0078471 A1 | 4/2003 | Foley et al. | |
| 2003/0083681 A1 | 5/2003 | Moutafis et al. | |
| 2003/0114731 A1 | 6/2003 | Cadeddu et al. | |
| 2003/0114732 A1 | 6/2003 | Webler et al. | |
| 2003/0120257 A1 | 6/2003 | Houston et al. | |
| 2003/0124009 A1 | 7/2003 | Ravi et al. | |
| 2003/0130564 A1 | 7/2003 | Martone et al. | |
| 2003/0130656 A1 | 7/2003 | Levin | |
| 2003/0139646 A1 | 7/2003 | Sharrow et al. | |
| 2003/0158521 A1 | 8/2003 | Ameri | |
| 2003/0167062 A1 | 9/2003 | Gambale et al. | |
| 2003/0171651 A1 | 9/2003 | Page et al. | |
| 2003/0176880 A1 | 9/2003 | Long et al. | |
| 2003/0216611 A1 | 11/2003 | Vu | |
| 2003/0216615 A1 | 11/2003 | Ouchi | |
| 2003/0220545 A1 | 11/2003 | Ouchi | |
| 2003/0225312 A1 | 12/2003 | Suzuki et al. | |
| 2003/0225332 A1 | 12/2003 | Okada et al. | |
| 2003/0229269 A1 | 12/2003 | Humphrey | |
| 2003/0229371 A1 | 12/2003 | Whitworth | |
| 2003/0236549 A1 | 12/2003 | Bonadio et al. | |
| 2004/0002683 A1 | 1/2004 | Nicholson et al. | |
| 2004/0024414 A1 | 2/2004 | Downing | |
| 2004/0034369 A1 | 2/2004 | Sauer et al. | |
| 2004/0054322 A1 | 3/2004 | Vargas | |
| 2004/0098007 A1 | 5/2004 | Heiss | |
| 2004/0101456 A1 | 5/2004 | Kuroshima et al. | |
| 2004/0104999 A1 | 6/2004 | Okada | |
| 2004/0116948 A1 | 6/2004 | Sixto, Jr. et al. | |
| 2004/0127940 A1 | 7/2004 | Ginn et al. | |
| 2004/0133077 A1 | 7/2004 | Obenchain et al. | |
| 2004/0133089 A1 | 7/2004 | Kilcoyne et al. | |
| 2004/0136779 A1 | 7/2004 | Bhaskar | |
| 2004/0138525 A1 | 7/2004 | Saadat et al. | |
| 2004/0138529 A1 | 7/2004 | Wiltshire et al. | |
| 2004/0138587 A1 | 7/2004 | Lyons, IV | |
| 2004/0161451 A1 | 8/2004 | Pierce et al. | |
| 2004/0167545 A1 | 8/2004 | Sadler et al. | |
| 2004/0176699 A1 | 9/2004 | Walker et al. | |
| 2004/0186350 A1 | 9/2004 | Brenneman et al. | |
| 2004/0193009 A1 | 9/2004 | Jaffe et al. | |
| 2004/0193146 A1 | 9/2004 | Lee et al. | |
| 2004/0193186 A1 | 9/2004 | Kortenbach et al. | |
| 2004/0193188 A1 | 9/2004 | Francese | |
| 2004/0193189 A1 | 9/2004 | Kortenbach et al. | |
| 2004/0193200 A1 | 9/2004 | Dworschak et al. | |
| 2004/0199052 A1 | 10/2004 | Banik et al. | |
| 2004/0199159 A1 | 10/2004 | Lee et al. | |
| 2004/0206859 A1 | 10/2004 | Chong et al. | |
| 2004/0210245 A1 | 10/2004 | Erickson et al. | |
| 2004/0215058 A1 | 10/2004 | Zirps et al. | |
| 2004/0225183 A1 | 11/2004 | Michlitsch et al. | |
| 2004/0225186 A1 | 11/2004 | Horne, Jr. et al. | |
| 2004/0225323 A1 | 11/2004 | Nagase et al. | |
| 2004/0230095 A1 | 11/2004 | Stefanchik et al. | |
| 2004/0230096 A1 | 11/2004 | Stefanchik et al. | |
| 2004/0230097 A1 | 11/2004 | Stefanchik et al. | |
| 2004/0230161 A1 | 11/2004 | Zeiner | |
| 2004/0243108 A1 | 12/2004 | Suzuki | |
| 2004/0249246 A1 | 12/2004 | Campos | |
| 2004/0249367 A1 | 12/2004 | Saadat et al. | |
| 2004/0249394 A1 | 12/2004 | Morris et al. | |
| 2004/0249443 A1 | 12/2004 | Shanley et al. | |
| 2004/0254572 A1 | 12/2004 | McIntyre et al. | |
| 2004/0260198 A1 | 12/2004 | Rothberg et al. | |
| 2004/0260337 A1 | 12/2004 | Freed | |
| 2005/0004515 A1 | 1/2005 | Hart et al. | |
| 2005/0033265 A1 | 2/2005 | Engel et al. | |
| 2005/0033277 A1 | 2/2005 | Clague et al. | |
| 2005/0033319 A1 | 2/2005 | Gambale et al. | |
| 2005/0033333 A1 | 2/2005 | Smith et al. | |
| 2005/0043690 A1 | 2/2005 | Todd | |
| 2005/0049616 A1 | 3/2005 | Rivera et al. | |
| 2005/0059963 A1 | 3/2005 | Phan et al. | |
| 2005/0059964 A1 | 3/2005 | Fitz | |
| 2005/0065475 A1 | 3/2005 | Saadat et al. | |
| 2005/0065509 A1* | 3/2005 | Coldwell et al. | 606/41 |
| 2005/0065517 A1 | 3/2005 | Chin | |
| 2005/0070754 A1 | 3/2005 | Nobis et al. | |
| 2005/0070763 A1 | 3/2005 | Nobis et al. | |
| 2005/0070764 A1 | 3/2005 | Nobis et al. | |
| 2005/0080413 A1 | 4/2005 | Canady | |
| 2005/0085693 A1 | 4/2005 | Belson et al. | |
| 2005/0085832 A1 | 4/2005 | Sancoff et al. | |
| 2005/0090837 A1 | 4/2005 | Sixto, Jr. et al. | |
| 2005/0090838 A1 | 4/2005 | Sixto, Jr. et al. | |
| 2005/0096502 A1 | 5/2005 | Khalili | |
| 2005/0101837 A1 | 5/2005 | Kalloo et al. | |
| 2005/0101838 A1 | 5/2005 | Camillocci et al. | |
| 2005/0101984 A1 | 5/2005 | Chanduszko et al. | |
| 2005/0107663 A1 | 5/2005 | Saadat et al. | |
| 2005/0107664 A1 | 5/2005 | Kalloo et al. | |
| 2005/0110881 A1 | 5/2005 | Glukhovsky et al. | |
| 2005/0113847 A1 | 5/2005 | Gadberry et al. | |
| 2005/0119613 A1 | 6/2005 | Moenning et al. | |
| 2005/0124855 A1 | 6/2005 | Jaffe et al. | |
| 2005/0125010 A1 | 6/2005 | Smith et al. | |
| 2005/0131279 A1 | 6/2005 | Boulais et al. | |
| 2005/0131457 A1 | 6/2005 | Douglas et al. | |
| 2005/0137454 A1 | 6/2005 | Saadat et al. | |
| 2005/0143647 A1 | 6/2005 | Minai et al. | |
| 2005/0143690 A1 | 6/2005 | High | |

(56) References Cited

U.S. PATENT DOCUMENTS

| | | |
|---|---|---|
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |
| 2005/0192478 A1 | 9/2005 | Williams et al. |
| 2005/0192598 A1 | 9/2005 | Johnson et al. |
| 2005/0192602 A1 | 9/2005 | Manzo |
| 2005/0192654 A1 | 9/2005 | Chanduszko et al. |
| 2005/0209624 A1 | 9/2005 | Vijay |
| 2005/0215858 A1 | 9/2005 | Vail, III |
| 2005/0216050 A1 | 9/2005 | Sepetka et al. |
| 2005/0222576 A1* | 10/2005 | Kick et al. ............ 606/104 |
| 2005/0228224 A1 | 10/2005 | Okada et al. |
| 2005/0228406 A1 | 10/2005 | Bose |
| 2005/0234297 A1 | 10/2005 | Devierre et al. |
| 2005/0250983 A1 | 11/2005 | Tremaglio et al. |
| 2005/0250990 A1 | 11/2005 | Le et al. |
| 2005/0250993 A1 | 11/2005 | Jaeger |
| 2005/0251166 A1 | 11/2005 | Vaughan et al. |
| 2005/0251176 A1 | 11/2005 | Swanstrom et al. |
| 2005/0261674 A1 | 11/2005 | Nobis et al. |
| 2005/0267492 A1 | 12/2005 | Poncet et al. |
| 2005/0272975 A1 | 12/2005 | McWeeney et al. |
| 2005/0272977 A1 | 12/2005 | Saadat et al. |
| 2005/0273084 A1 | 12/2005 | Hinman et al. |
| 2005/0274935 A1 | 12/2005 | Nelson |
| 2005/0277945 A1 | 12/2005 | Saadat et al. |
| 2005/0277951 A1 | 12/2005 | Smith et al. |
| 2005/0277952 A1 | 12/2005 | Arp et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277957 A1 | 12/2005 | Kuhns et al. |
| 2005/0283118 A1 | 12/2005 | Uth et al. |
| 2005/0283119 A1 | 12/2005 | Uth et al. |
| 2005/0288555 A1 | 12/2005 | Binmoeller |
| 2006/0004406 A1 | 1/2006 | Wehrstein et al. |
| 2006/0004409 A1 | 1/2006 | Nobis et al. |
| 2006/0004410 A1 | 1/2006 | Nobis et al. |
| 2006/0015009 A1 | 1/2006 | Jaffe et al. |
| 2006/0015131 A1 | 1/2006 | Kierce et al. |
| 2006/0020167 A1 | 1/2006 | Sitzmann |
| 2006/0020247 A1 | 1/2006 | Kagan et al. |
| 2006/0025654 A1 | 2/2006 | Suzuki et al. |
| 2006/0025781 A1 | 2/2006 | Young et al. |
| 2006/0025812 A1 | 2/2006 | Shelton, IV |
| 2006/0025819 A1 | 2/2006 | Nobis et al. |
| 2006/0036267 A1 | 2/2006 | Saadat et al. |
| 2006/0041188 A1 | 2/2006 | Dirusso et al. |
| 2006/0058582 A1 | 3/2006 | Maahs et al. |
| 2006/0058776 A1 | 3/2006 | Bilsbury |
| 2006/0064083 A1 | 3/2006 | Khalaj et al. |
| 2006/0069396 A1 | 3/2006 | Meade et al. |
| 2006/0069424 A1 | 3/2006 | Acosta et al. |
| 2006/0069425 A1 | 3/2006 | Hillis et al. |
| 2006/0069429 A1 | 3/2006 | Spence et al. |
| 2006/0074413 A1 | 4/2006 | Behzadian |
| 2006/0079890 A1 | 4/2006 | Guerra |
| 2006/0089528 A1 | 4/2006 | Tartaglia et al. |
| 2006/0095031 A1 | 5/2006 | Ormsby |
| 2006/0095060 A1 | 5/2006 | Mayenberger et al. |
| 2006/0100687 A1 | 5/2006 | Fahey et al. |
| 2006/0106423 A1 | 5/2006 | Weisel et al. |
| 2006/0111209 A1 | 5/2006 | Hinman et al. |
| 2006/0111210 A1 | 5/2006 | Hinman et al. |
| 2006/0111704 A1 | 5/2006 | Brenneman et al. |
| 2006/0129166 A1 | 6/2006 | Lavelle |
| 2006/0135962 A1 | 6/2006 | Kick et al. |
| 2006/0135971 A1 | 6/2006 | Swanstrom et al. |
| 2006/0135984 A1 | 6/2006 | Kramer et al. |
| 2006/0142644 A1 | 6/2006 | Mulac et al. |
| 2006/0142652 A1 | 6/2006 | Keenan |
| 2006/0142790 A1 | 6/2006 | Gertner |
| 2006/0142798 A1 | 6/2006 | Holman et al. |
| 2006/0149131 A1 | 7/2006 | Or |
| 2006/0149132 A1 | 7/2006 | Iddan |
| 2006/0149135 A1 | 7/2006 | Paz |
| 2006/0161190 A1 | 7/2006 | Gadberry et al. |
| 2006/0167416 A1 | 7/2006 | Mathis et al. |
| 2006/0167482 A1 | 7/2006 | Swain et al. |
| 2006/0178560 A1 | 8/2006 | Saadat et al. |
| 2006/0183975 A1 | 8/2006 | Saadat et al. |
| 2006/0184161 A1 | 8/2006 | Maahs et al. |
| 2006/0189844 A1 | 8/2006 | Tien |
| 2006/0189845 A1 | 8/2006 | Maahs et al. |
| 2006/0190027 A1 | 8/2006 | Downey |
| 2006/0195084 A1 | 8/2006 | Slater |
| 2006/0200005 A1 | 9/2006 | Bjork et al. |
| 2006/0200121 A1 | 9/2006 | Mowery |
| 2006/0200169 A1 | 9/2006 | Sniffin |
| 2006/0200170 A1 | 9/2006 | Aranyi |
| 2006/0200199 A1 | 9/2006 | Bonutti et al. |
| 2006/0217665 A1 | 9/2006 | Prosek |
| 2006/0217697 A1 | 9/2006 | Lau et al. |
| 2006/0217742 A1 | 9/2006 | Messerly et al. |
| 2006/0217743 A1 | 9/2006 | Messerly et al. |
| 2006/0229639 A1 | 10/2006 | Whitfield |
| 2006/0229640 A1 | 10/2006 | Whitfield |
| 2006/0237022 A1 | 10/2006 | Chen et al. |
| 2006/0237023 A1 | 10/2006 | Cox et al. |
| 2006/0241570 A1 | 10/2006 | Wilk |
| 2006/0247500 A1 | 11/2006 | Voegele et al. |
| 2006/0247576 A1 | 11/2006 | Poncet |
| 2006/0247663 A1 | 11/2006 | Schwartz et al. |
| 2006/0247673 A1 | 11/2006 | Voegele et al. |
| 2006/0253004 A1 | 11/2006 | Frisch et al. |
| 2006/0253039 A1 | 11/2006 | McKenna et al. |
| 2006/0258907 A1 | 11/2006 | Stefanchik et al. |
| 2006/0258908 A1 | 11/2006 | Stefanchik et al. |
| 2006/0258910 A1 | 11/2006 | Stefanchik et al. |
| 2006/0258954 A1 | 11/2006 | Timberlake et al. |
| 2006/0258955 A1 | 11/2006 | Hoffman et al. |
| 2006/0259010 A1 | 11/2006 | Stefanchik et al. |
| 2006/0259073 A1 | 11/2006 | Miyamoto et al. |
| 2006/0264752 A1 | 11/2006 | Rubinsky et al. |
| 2006/0264904 A1 | 11/2006 | Kerby et al. |
| 2006/0264930 A1 | 11/2006 | Nishimura |
| 2006/0270902 A1 | 11/2006 | Igarashi et al. |
| 2006/0271042 A1 | 11/2006 | Latterell et al. |
| 2006/0271102 A1 | 11/2006 | Bosshard et al. |
| 2006/0276835 A1 | 12/2006 | Uchida |
| 2006/0281970 A1 | 12/2006 | Stokes et al. |
| 2006/0282106 A1 | 12/2006 | Cole et al. |
| 2006/0285732 A1 | 12/2006 | Horn et al. |
| 2006/0287644 A1 | 12/2006 | Inganas et al. |
| 2006/0287666 A1 | 12/2006 | Saadat et al. |
| 2006/0293626 A1 | 12/2006 | Byrum et al. |
| 2007/0002135 A1 | 1/2007 | Glukhovsky |
| 2007/0005019 A1 | 1/2007 | Okishige |
| 2007/0010801 A1 | 1/2007 | Chen et al. |
| 2007/0015965 A1 | 1/2007 | Cox et al. |
| 2007/0016225 A1 | 1/2007 | Nakao |
| 2007/0032700 A1 | 2/2007 | Fowler et al. |
| 2007/0032701 A1 | 2/2007 | Fowler et al. |
| 2007/0043261 A1 | 2/2007 | Watanabe et al. |
| 2007/0043345 A1 | 2/2007 | Davalos et al. |
| 2007/0049800 A1 | 3/2007 | Boulais |
| 2007/0049902 A1 | 3/2007 | Griffin et al. |
| 2007/0051375 A1 | 3/2007 | Milliman |
| 2007/0060880 A1 | 3/2007 | Gregorich et al. |
| 2007/0066869 A1 | 3/2007 | Hoffman |
| 2007/0067017 A1 | 3/2007 | Trapp |
| 2007/0073102 A1 | 3/2007 | Matsuno et al. |
| 2007/0073269 A1 | 3/2007 | Becker |
| 2007/0079924 A1 | 4/2007 | Saadat et al. |
| 2007/0083195 A1 | 4/2007 | Werneth et al. |
| 2007/0088370 A1 | 4/2007 | Kahle et al. |
| 2007/0100375 A1 | 5/2007 | Mikkaichi et al. |

(56) References Cited

U.S. PATENT DOCUMENTS

| | | |
|---|---|---|
| 2007/0100376 A1 | 5/2007 | Mikkaichi et al. |
| 2007/0106118 A1 | 5/2007 | Moriyama |
| 2007/0106317 A1 | 5/2007 | Shelton, IV et al. |
| 2007/0112251 A1 | 5/2007 | Nakhuda |
| 2007/0112331 A1 | 5/2007 | Weber et al. |
| 2007/0112342 A1 | 5/2007 | Pearson et al. |
| 2007/0112383 A1 | 5/2007 | Conlon et al. |
| 2007/0112384 A1 | 5/2007 | Conlon et al. |
| 2007/0112385 A1 | 5/2007 | Conlon |
| 2007/0112417 A1 | 5/2007 | Shanley et al. |
| 2007/0112425 A1 | 5/2007 | Schaller et al. |
| 2007/0118115 A1 | 5/2007 | Artale et al. |
| 2007/0123840 A1 | 5/2007 | Cox |
| 2007/0129605 A1 | 6/2007 | Schaaf |
| 2007/0129719 A1 | 6/2007 | Kendale et al. |
| 2007/0129760 A1 | 6/2007 | Demarais et al. |
| 2007/0135709 A1 | 6/2007 | Rioux et al. |
| 2007/0135803 A1 | 6/2007 | Belson |
| 2007/0142706 A1 | 6/2007 | Matsui et al. |
| 2007/0142710 A1 | 6/2007 | Yokoi et al. |
| 2007/0142780 A1 | 6/2007 | Van Lue |
| 2007/0154460 A1 | 7/2007 | Kraft et al. |
| 2007/0156028 A1 | 7/2007 | Van Lue et al. |
| 2007/0156127 A1 | 7/2007 | Rioux et al. |
| 2007/0161855 A1 | 7/2007 | Mikkaichi et al. |
| 2007/0162101 A1 | 7/2007 | Burgermeister et al. |
| 2007/0167901 A1 | 7/2007 | Herrig et al. |
| 2007/0173691 A1 | 7/2007 | Yokoi et al. |
| 2007/0173869 A1 | 7/2007 | Gannoe et al. |
| 2007/0173870 A2 | 7/2007 | Zacharias |
| 2007/0173872 A1 | 7/2007 | Neuenfeldt |
| 2007/0179525 A1 | 8/2007 | Frecker et al. |
| 2007/0179530 A1 | 8/2007 | Tieu et al. |
| 2007/0197865 A1 | 8/2007 | Miyake et al. |
| 2007/0198057 A1 | 8/2007 | Gelbart et al. |
| 2007/0203398 A1 * | 8/2007 | Bonadio et al. ............... 600/208 |
| 2007/0203487 A1 | 8/2007 | Sugita |
| 2007/0208336 A1 | 9/2007 | Kim et al. |
| 2007/0208364 A1 | 9/2007 | Smith et al. |
| 2007/0213754 A1 | 9/2007 | Mikkaichi et al. |
| 2007/0225554 A1 | 9/2007 | Maseda et al. |
| 2007/0233040 A1 | 10/2007 | Macnamara et al. |
| 2007/0244358 A1 | 10/2007 | Lee |
| 2007/0250038 A1 | 10/2007 | Boulais |
| 2007/0250057 A1 | 10/2007 | Nobis et al. |
| 2007/0255096 A1 | 11/2007 | Stefanchik et al. |
| 2007/0255100 A1 | 11/2007 | Barlow et al. |
| 2007/0255273 A1 | 11/2007 | Fernandez et al. |
| 2007/0255303 A1 | 11/2007 | Bakos et al. |
| 2007/0255306 A1 | 11/2007 | Conlon et al. |
| 2007/0260112 A1 | 11/2007 | Rahmani |
| 2007/0260117 A1 | 11/2007 | Zwolinski et al. |
| 2007/0260121 A1 | 11/2007 | Bakos et al. |
| 2007/0260242 A1 | 11/2007 | Dycus et al. |
| 2007/0260273 A1 | 11/2007 | Cropper et al. |
| 2007/0260302 A1 | 11/2007 | Igaki |
| 2007/0270629 A1 | 11/2007 | Charles |
| 2007/0270889 A1 | 11/2007 | Conlon et al. |
| 2007/0270895 A1 | 11/2007 | Nobis et al. |
| 2007/0270907 A1 | 11/2007 | Stokes et al. |
| 2007/0282165 A1 | 12/2007 | Hopkins et al. |
| 2007/0282371 A1 | 12/2007 | Lee et al. |
| 2007/0293727 A1 | 12/2007 | Goldfarb et al. |
| 2007/0299387 A1 | 12/2007 | Williams et al. |
| 2008/0004650 A1 | 1/2008 | George |
| 2008/0015409 A1 | 1/2008 | Barlow et al. |
| 2008/0015413 A1 | 1/2008 | Barlow et al. |
| 2008/0015552 A1 | 1/2008 | Doyle et al. |
| 2008/0021416 A1 | 1/2008 | Arai et al. |
| 2008/0022927 A1 | 1/2008 | Zhang et al. |
| 2008/0027387 A1 | 1/2008 | Grabinsky |
| 2008/0033451 A1 | 2/2008 | Rieber et al. |
| 2008/0051629 A1 | 2/2008 | Sugiyama et al. |
| 2008/0051735 A1 | 2/2008 | Measamer et al. |
| 2008/0058586 A1 | 3/2008 | Karpiel |
| 2008/0058854 A1 | 3/2008 | Kieturakis et al. |
| 2008/0065169 A1 | 3/2008 | Colliou et al. |
| 2008/0071264 A1 | 3/2008 | Azure |
| 2008/0086172 A1 | 4/2008 | Martin et al. |
| 2008/0097159 A1 | 4/2008 | Ishiguro |
| 2008/0097472 A1 | 4/2008 | Agmon et al. |
| 2008/0097483 A1 | 4/2008 | Ortiz et al. |
| 2008/0103527 A1 | 5/2008 | Martin et al. |
| 2008/0114384 A1 | 5/2008 | Chang et al. |
| 2008/0119870 A1 | 5/2008 | Williams |
| 2008/0119891 A1 | 5/2008 | Miles et al. |
| 2008/0125796 A1 | 5/2008 | Graham |
| 2008/0132892 A1 | 6/2008 | Lunsford et al. |
| 2008/0139882 A1 | 6/2008 | Fujimori |
| 2008/0140069 A1 | 6/2008 | Filloux et al. |
| 2008/0140071 A1 | 6/2008 | Vegesna |
| 2008/0147113 A1 | 6/2008 | Nobis et al. |
| 2008/0171907 A1 | 7/2008 | Long et al. |
| 2008/0177135 A1 | 7/2008 | Muyari et al. |
| 2008/0188710 A1 | 8/2008 | Segawa et al. |
| 2008/0188868 A1 | 8/2008 | Weitzner et al. |
| 2008/0200755 A1 | 8/2008 | Bakos |
| 2008/0200762 A1 | 8/2008 | Stokes et al. |
| 2008/0200911 A1 | 8/2008 | Long |
| 2008/0200933 A1 | 8/2008 | Bakos et al. |
| 2008/0200934 A1 | 8/2008 | Fox |
| 2008/0208213 A1 | 8/2008 | Benjamin et al. |
| 2008/0221587 A1 | 9/2008 | Schwartz |
| 2008/0221619 A1 | 9/2008 | Spivey et al. |
| 2008/0228213 A1 | 9/2008 | Blakeney et al. |
| 2008/0230972 A1 | 9/2008 | Ganley |
| 2008/0234696 A1 | 9/2008 | Taylor et al. |
| 2008/0243106 A1 | 10/2008 | Coe et al. |
| 2008/0243148 A1 | 10/2008 | Mikkaichi et al. |
| 2008/0243176 A1 | 10/2008 | Weitzner et al. |
| 2008/0249567 A1 | 10/2008 | Kaplan |
| 2008/0262513 A1 | 10/2008 | Stahler et al. |
| 2008/0262524 A1 | 10/2008 | Bangera et al. |
| 2008/0262540 A1 | 10/2008 | Bangera et al. |
| 2008/0269782 A1 | 10/2008 | Stefanchik et al. |
| 2008/0269783 A1 | 10/2008 | Griffith |
| 2008/0275474 A1 | 11/2008 | Martin et al. |
| 2008/0275475 A1 | 11/2008 | Schwemberger et al. |
| 2008/0287737 A1 | 11/2008 | Dejima |
| 2008/0287983 A1 | 11/2008 | Smith et al. |
| 2008/0300461 A1 | 12/2008 | Shaw et al. |
| 2008/0300547 A1 | 12/2008 | Bakos |
| 2008/0309758 A1 | 12/2008 | Karasawa et al. |
| 2008/0312496 A1 | 12/2008 | Zwolinski |
| 2008/0312499 A1 | 12/2008 | Handa et al. |
| 2008/0312500 A1 | 12/2008 | Asada et al. |
| 2008/0312506 A1 | 12/2008 | Spivey et al. |
| 2008/0319436 A1 | 12/2008 | Daniel et al. |
| 2008/0319439 A1 | 12/2008 | Ootsubu |
| 2009/0005636 A1 | 1/2009 | Pang et al. |
| 2009/0054728 A1 | 2/2009 | Trusty |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0069634 A1 | 3/2009 | Larkin |
| 2009/0076499 A1 | 3/2009 | Azure |
| 2009/0078736 A1 | 3/2009 | Van Lue |
| 2009/0082776 A1 | 3/2009 | Cresina |
| 2009/0082779 A1 | 3/2009 | Nakao |
| 2009/0112059 A1 | 4/2009 | Nobis |
| 2009/0112062 A1 | 4/2009 | Bakos |
| 2009/0112063 A1 | 4/2009 | Bakos et al. |
| 2009/0125042 A1 | 5/2009 | Mouw |
| 2009/0131751 A1 | 5/2009 | Spivey et al. |
| 2009/0131932 A1 | 5/2009 | Vakharia et al. |
| 2009/0131933 A1 | 5/2009 | Ghabrial et al. |
| 2009/0143639 A1 | 6/2009 | Stark |
| 2009/0143649 A1 | 6/2009 | Rossi |
| 2009/0143794 A1 * | 6/2009 | Conlon et al. ............... 606/167 |
| 2009/0143818 A1 | 6/2009 | Faller et al. |
| 2009/0149710 A1 | 6/2009 | Stefanchik et al. |
| 2009/0177031 A1 | 7/2009 | Surti et al. |
| 2009/0177219 A1 | 7/2009 | Conlon |
| 2009/0182332 A1 | 7/2009 | Long et al. |

(56) References Cited

U.S. PATENT DOCUMENTS

| | | |
|---|---|---|
| 2009/0192344 A1 | 7/2009 | Bakos et al. |
| 2009/0192534 A1 | 7/2009 | Ortiz et al. |
| 2009/0198231 A1 | 8/2009 | Esser et al. |
| 2009/0198253 A1 | 8/2009 | Omori |
| 2009/0210000 A1 | 8/2009 | Sullivan et al. |
| 2009/0216248 A1 | 8/2009 | Uenohara et al. |
| 2009/0221873 A1 | 9/2009 | McGrath |
| 2009/0227828 A1 | 9/2009 | Swain et al. |
| 2009/0228001 A1 | 9/2009 | Pacey |
| 2009/0248055 A1 | 10/2009 | Spivey et al. |
| 2009/0259105 A1 | 10/2009 | Miyano et al. |
| 2009/0269317 A1 | 10/2009 | Davalos |
| 2009/0281559 A1 | 11/2009 | Swain et al. |
| 2009/0287206 A1 | 11/2009 | Jun |
| 2009/0287236 A1 | 11/2009 | Bakos et al. |
| 2009/0292164 A1 | 11/2009 | Yamatani |
| 2009/0299135 A1 | 12/2009 | Spivey |
| 2009/0299143 A1 | 12/2009 | Conlon et al. |
| 2009/0299362 A1 | 12/2009 | Long et al. |
| 2009/0299385 A1 | 12/2009 | Stefanchik et al. |
| 2009/0299406 A1 | 12/2009 | Swain et al. |
| 2009/0299409 A1 | 12/2009 | Coe et al. |
| 2009/0306658 A1 | 12/2009 | Nobis et al. |
| 2009/0306683 A1 | 12/2009 | Zwolinski et al. |
| 2009/0322864 A1 | 12/2009 | Karasawa et al. |
| 2009/0326332 A1 | 12/2009 | Carter |
| 2009/0326561 A1 | 12/2009 | Carroll, II et al. |
| 2010/0010294 A1 | 1/2010 | Conlon et al. |
| 2010/0010298 A1 | 1/2010 | Bakos et al. |
| 2010/0010299 A1 | 1/2010 | Bakos et al. |
| 2010/0010303 A1 | 1/2010 | Bakos |
| 2010/0010510 A1 | 1/2010 | Stefanchik |
| 2010/0010511 A1 | 1/2010 | Harris et al. |
| 2010/0023032 A1 | 1/2010 | Granja Filho |
| 2010/0030211 A1 | 2/2010 | Davalos et al. |
| 2010/0036198 A1 | 2/2010 | Tacchino et al. |
| 2010/0042045 A1 | 2/2010 | Spivey |
| 2010/0048990 A1 | 2/2010 | Bakos |
| 2010/0049190 A1 | 2/2010 | Long et al. |
| 2010/0049223 A1 | 2/2010 | Granja Filho |
| 2010/0056861 A1 | 3/2010 | Spivey |
| 2010/0056862 A1 | 3/2010 | Bakos |
| 2010/0056864 A1 | 3/2010 | Lee |
| 2010/0057085 A1 | 3/2010 | Holcomb et al. |
| 2010/0057108 A1 | 3/2010 | Spivey et al. |
| 2010/0063538 A1 | 3/2010 | Spivey et al. |
| 2010/0076451 A1 | 3/2010 | Zwolinski et al. |
| 2010/0076460 A1 | 3/2010 | Taylor et al. |
| 2010/0081877 A1 | 4/2010 | Vakharia |
| 2010/0087813 A1 | 4/2010 | Long |
| 2010/0091128 A1 | 4/2010 | Ogasawara et al. |
| 2010/0113872 A1 | 5/2010 | Asada et al. |
| 2010/0121362 A1 | 5/2010 | Clague et al. |
| 2010/0130817 A1 | 5/2010 | Conlon |
| 2010/0130975 A1 | 5/2010 | Long |
| 2010/0131005 A1 | 5/2010 | Conlon |
| 2010/0152539 A1 | 6/2010 | Ghabrial et al. |
| 2010/0152609 A1 | 6/2010 | Zwolinski et al. |
| 2010/0152746 A1 | 6/2010 | Ceniccola et al. |
| 2010/0179510 A1 | 7/2010 | Fox et al. |
| 2010/0179530 A1 | 7/2010 | Long et al. |
| 2010/0191050 A1 | 7/2010 | Zwolinski |
| 2010/0191267 A1 | 7/2010 | Fox |
| 2010/0198005 A1 | 8/2010 | Fox |
| 2010/0198149 A1 | 8/2010 | Fox |
| 2010/0198244 A1 | 8/2010 | Spivey et al. |
| 2010/0198248 A1 | 8/2010 | Vakharia |
| 2010/0217367 A1 | 8/2010 | Belson |
| 2010/0249700 A1 | 9/2010 | Spivey |
| 2010/0261994 A1 | 10/2010 | Davalos et al. |
| 2010/0286791 A1 | 11/2010 | Goldsmith |
| 2010/0298642 A1 | 11/2010 | Trusty et al. |
| 2010/0312056 A1 | 12/2010 | Galperin et al. |
| 2010/0331622 A2 | 12/2010 | Conlon |
| 2010/0331758 A1 | 12/2010 | Davalos et al. |
| 2010/0331774 A2 | 12/2010 | Spivey |
| 2011/0077476 A1 | 3/2011 | Rofougaran |
| 2011/0093009 A1 | 4/2011 | Fox |
| 2011/0098694 A1 | 4/2011 | Long |
| 2011/0098704 A1 | 4/2011 | Long et al. |
| 2011/0106221 A1 | 5/2011 | Neal, II et al. |
| 2011/0112434 A1 | 5/2011 | Ghabrial et al. |
| 2011/0115891 A1 | 5/2011 | Trusty |
| 2011/0124964 A1 | 5/2011 | Nobis |
| 2011/0152609 A1 | 6/2011 | Trusty et al. |
| 2011/0152610 A1 | 6/2011 | Trusty et al. |
| 2011/0152612 A1 | 6/2011 | Trusty et al. |
| 2011/0152858 A1 | 6/2011 | Long et al. |
| 2011/0152859 A1 | 6/2011 | Long et al. |
| 2011/0152878 A1 | 6/2011 | Trusty et al. |
| 2011/0152923 A1 | 6/2011 | Fox |
| 2011/0160514 A1 | 6/2011 | Long et al. |
| 2011/0190659 A1 | 8/2011 | Long et al. |
| 2011/0190764 A1 | 8/2011 | Long et al. |
| 2011/0193948 A1 | 8/2011 | Amling et al. |
| 2011/0245619 A1 | 10/2011 | Holcomb |
| 2011/0285488 A1 | 11/2011 | Scott et al. |
| 2011/0306971 A1 | 12/2011 | Long |
| 2012/0004502 A1 | 1/2012 | Weitzner et al. |
| 2012/0029335 A1 | 2/2012 | Sudam et al. |
| 2012/0088965 A1 | 4/2012 | Stokes et al. |
| 2012/0089089 A1 | 4/2012 | Swain et al. |
| 2012/0089093 A1 | 4/2012 | Trusty |
| 2012/0116155 A1 | 5/2012 | Trusty |
| 2012/0179148 A1 | 7/2012 | Conlon |
| 2012/0191075 A1 | 7/2012 | Trusty |
| 2012/0191076 A1 | 7/2012 | Voegele et al. |
| 2012/0220998 A1 | 8/2012 | Long et al. |
| 2012/0220999 A1 | 8/2012 | Long |
| 2012/0221002 A1 | 8/2012 | Long et al. |
| 2012/0238796 A1 | 9/2012 | Conlon |
| 2012/0330306 A1 | 12/2012 | Long et al. |
| 2013/0090666 A1 | 4/2013 | Hess et al. |

FOREIGN PATENT DOCUMENTS

| | | |
|---|---|---|
| DE | 4323585 A1 | 1/1995 |
| DE | 19713797 A1 | 10/1997 |
| DE | 19757056 B4 | 8/2008 |
| DE | 102006027873 B4 | 10/2009 |
| EP | 0086338 A1 | 8/1983 |
| EP | 0286415 A2 | 10/1988 |
| EP | 0589454 A2 | 3/1994 |
| EP | 0464479 B1 | 3/1995 |
| EP | 0529675 B1 | 2/1996 |
| EP | 0621009 B1 | 7/1997 |
| EP | 0724863 B1 | 7/1999 |
| EP | 0760629 B1 | 11/1999 |
| EP | 0818974 B1 | 7/2001 |
| EP | 1281356 A2 | 2/2003 |
| EP | 0947166 B1 | 5/2003 |
| EP | 0836832 81 | 12/2003 |
| EP | 1402837 A1 | 3/2004 |
| EP | 0744918 B1 | 4/2004 |
| EP | 0931515 B1 | 8/2004 |
| EP | 0941128 B1 | 10/2004 |
| EP | 1411843 81 | 10/2004 |
| EP | 1150614 B1 | 11/2004 |
| EP | 1477104 A1 | 11/2004 |
| EP | 1481642 A1 | 12/2004 |
| EP | 1493391 A1 | 1/2005 |
| EP | 0848598 B1 | 2/2005 |
| EP | 1281360 B1 | 3/2005 |
| EP | 1568330 A1 | 8/2005 |
| EP | 1452143 B1 | 9/2005 |
| EP | 1616527 A2 | 1/2006 |
| EP | 1006888 B1 | 3/2006 |
| EP | 1629764 A1 | 3/2006 |
| EP | 1013229 B1 | 6/2006 |
| EP | 1721561 A1 | 11/2006 |
| EP | 1153578 B1 | 3/2007 |
| EP | 1334696 B1 | 3/2007 |
| EP | 1769766 A1 | 4/2007 |
| EP | 1836971 A2 | 9/2007 |

(56) References Cited

FOREIGN PATENT DOCUMENTS

| | | |
|---|---|---|
| EP | 1836980 A1 | 9/2007 |
| EP | 1854421 A2 | 11/2007 |
| EP | 1857061 A1 | 11/2007 |
| EP | 1875876 A1 | 1/2008 |
| EP | 1891881 A1 | 2/2008 |
| EP | 1902663 A1 | 3/2008 |
| EP | 1477106 B1 | 6/2008 |
| EP | 1949844 A1 | 7/2008 |
| EP | 1518499 B1 | 8/2008 |
| EP | 1582138 B1 | 9/2008 |
| EP | 1709918 B1 | 10/2008 |
| EP | 1985226 A2 | 10/2008 |
| EP | 1994904 A1 | 11/2008 |
| EP | 1707130 B1 | 12/2008 |
| EP | 0723462 B1 | 3/2009 |
| EP | 1769749 B1 | 11/2009 |
| EP | 2135545 A2 | 12/2009 |
| EP | 1493397 B1 | 9/2011 |
| FR | 2731610 A1 | 9/1996 |
| GB | 330629 A | 6/1930 |
| GB | 2335860 A | 10/1999 |
| GB | 2403909 A | 1/2005 |
| GB | 2421190 A | 6/2006 |
| GB | 2443261 A | 4/2008 |
| JP | 56-46674 | 4/1981 |
| JP | 63309252 A | 12/1988 |
| JP | 4038960 A | 2/1992 |
| JP | 8-29699 A | 2/1996 |
| JP | 2000245683 A | 9/2000 |
| JP | 2002-369791 A | 12/2002 |
| JP | 2003-088494 A | 3/2003 |
| JP | 2003-235852 A | 8/2003 |
| JP | 2004-33525 A | 2/2004 |
| JP | 2004-065745 A | 3/2004 |
| JP | 2005-121947 A | 5/2005 |
| JP | 2005-261514 A | 9/2005 |
| JP | 2006297005 A | 11/2006 |
| JP | 2006-343510 A | 12/2006 |
| NL | 1021295 C2 | 2/2004 |
| SU | 194230 | 5/1967 |
| SU | 980703 | 12/1982 |
| WO | WO 84/01707 A1 | 5/1984 |
| WO | WO 92/13494 A1 | 8/1992 |
| WO | WO 93/10850 A1 | 6/1993 |
| WO | WO 93/20760 A1 | 10/1993 |
| WO | WO 93/20765 A1 | 10/1993 |
| WO | WO 95/09666 A1 | 4/1995 |
| WO | WO 96/22056 A1 | 7/1996 |
| WO | WO 96/27331 A1 | 9/1996 |
| WO | WO 96/39946 A1 | 12/1996 |
| WO | WO 97/12557 A1 | 4/1997 |
| WO | WO 98/01080 A1 | 1/1998 |
| WO | WO 99/00060 A1 | 1/1999 |
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 00/68665 A1 | 11/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2007/143200 A2 | 12/2007 |
| WO | WO 2007/144004 A1 | 12/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/036457 A1 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Zadno et al., "Linear Superelasticity in Cold-Worked NI-TI," Engineering Aspects of Shape Memory Alloys, pp. 414-419 (1990).
U.S. Appl. No. 12/752,701, filed Apr. 1, 2010.
U.S. Appl. No. 13/013,131, filed Jan. 25, 2011.
U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
OCTO Port Modular Laparoscopy System for Single Incision Access, Jan. 4, 2010; URL http://www.medgadget.com/archives/2010/01/octo_port_modular_laparo...; accessed Jan. 5, 2010 (4 pages).
Hakko Retractors, obtained Aug. 25, 2009 (5 pages).
U.S. Appl. No. 12/468,462, filed May 19, 2009.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (1994).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With The Flow," Design News, 2 pages, Jul. 17, 2006.

(56) References Cited

OTHER PUBLICATIONS

Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Enclose., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Dec. 1825, et le Premier Tremestre De 1826, Séance Du 24 Fevrier 1826. Recuell De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.
J.W. Hazey et al., "Natural Orifice Transgastric Endoscopic Peritoneoscopy in Humans: Initial Clinical Trial," Surg Endosc, (Jan. 2008), vol. 22(1), pp. 16-20.
N. Chopita et al., "Endoscopic Gastroenteric Anastamosis Using Magnets," Endoscopy, (2005), vol. 37(4), pp. 313-317.
C. Cope et al., "Long Term Patency of Experimental Magnetic Compression Gastroenteric Anastomoses Achieved with Covered Stents," Gastrointest Endosc, (2001), vol. 53, pp. 780-784.
H. Okajima et al., "Magnet Compression Anastamosis for Bile Duct Stenosis After Duct to Duct Biliary Reconstruction in Living Donor Liver Transplantation," Liver Transplantation (2005), pp. 473-475.
A. Fritscher-Ravens et al., "Transluminal Endosurgery: Single Lumen Access Anastamotic Device for Flexible Endoscopy," Gastrointestinal Endosc, (2003), vol. 58(4), pp. 585-591.
G.A. Hallenbeck, M.D. et al., "An Instrument for Colorectal Anastomosis Without Sutrues," Dis Col Rectum, (1963), vol. 5, pp. 98-101.
T. Hardy, Jr., M.D. et al., "A Biofragmentable Ring for Sutureless Bowel Anastomosis. An Experimental Study," Dis Col Rectum, (1985), vol. 28, pp. 484-490.
P. O'Neill, M.D. et al., "Nonsuture Intestinal Anastomosis," Am J. Surg, (1962), vol. 104, pp. 761-767.
C.P. Swain, M.D. et al., "Anastomosis at Flexible Endoscopy: An Experimental Study of Compression Button Gastrojejunostomy," Gastrointest Endosc, (1991), vol. 37, pp. 628-632.
J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).
Printout of web page—http://www.vacumed.com/zoom/product/Product.do?compId=27&prodid=852, #51XX Low-Cost Permanent Tubes 2MM ID, Smooth Interior Walls, VacuMed, Ventura, California, Accessed Jul. 24, 2007.
Endoscopic Retrograde Cholangiopancreatogram (ERCP); [online] URL: http://www.webmd.com/digestive-disorders/endoscopic-retrograde-cholanglopancreatogram-ercp.htm; last updated: Apr. 30, 2007; accessed: Feb. 21, 2008 (6 pages).
ERCP; Jackson Siegelbaum Gastroenterology; [online] URL: http://www.gicare.com/pated/epdgs20.htm; accessed Feb. 21, 2008 (3 pages).
D.G. Fong et al., "Transcolonic Ventral Wall Hernia Mesh Fixation in a Porcine Model," Endoscopy 2007; 39: 865-869.
B. Rubinsky, Ph.D., "Irreversible Electroporation in Medicine," Technology in Cancer Research and Treatment, vol. 6, No. 4, Aug. 2007, pp. 255-259.
D.B. Nelson, MD et al., "Endoscopic Hemostatic Devices," Gastrointestinal Endoscopy, vol. 54, No. 6, 2001, pp. 833-840.
CRE™ Pulmonary Balloon Dilator; [online] URL: http://www.bostonscientific.com/Device.bsci?page=HCP_Overview&navRe1Id=1000.1003&method=D..., accessed Jul. 18, 2008 (4 pages).
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkmüller, M,D., et al., "Transmural Drainage of Pancreatic Fluid Collections Without Electrocautery Using the Seldinger Technique," Gastrointestinal Endoscopy, vol. 48, No. 2, 1998, pp. 195-200, (Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation In Vivo," The Journal of Immunology, 164, pp. 4635-4640 (2000).
Weaver et al., "Theory of electroporation: A review," Bioelectrochemistry and Bioenergetics, 41, pp. 135-160 (1996).
Mulier et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

(56) References Cited

OTHER PUBLICATIONS

"Ethicon Endo-Surgery Studies Presented At DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using A Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using A Magnetically Anchored Camera and Novel Instrumentation," Poster submitted along with Abstract at SAGES Annual Meeting in Phoenix, AZ, Apr. 22, 2009 (1 page).
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/614,143, filed Nov. 6, 2009.
U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
Rutala et al. "Guideline for Disinfection and Sterilization in Healthcare Facilities, 2008" (available at http://www.cdc.gov/hicpac/Disinfection_Sterilization/13_11sterilizingPractices.html).
U.S. Appl. No. 13/267,251, filed Oct. 6, 2011.
U.S. Appl. No. 13/325,791, filed Dec. 14, 2011.
U.S. Appl. No. 13/399,358, filed Feb. 17, 2012.
U.S. Appl. No. 13/420,818, filed Mar. 15, 2012.
Bewlay et al., "Spinning" in ASM Handbook, vol. 14B, Metalworking: Sheet Forming (2006).

* cited by examiner

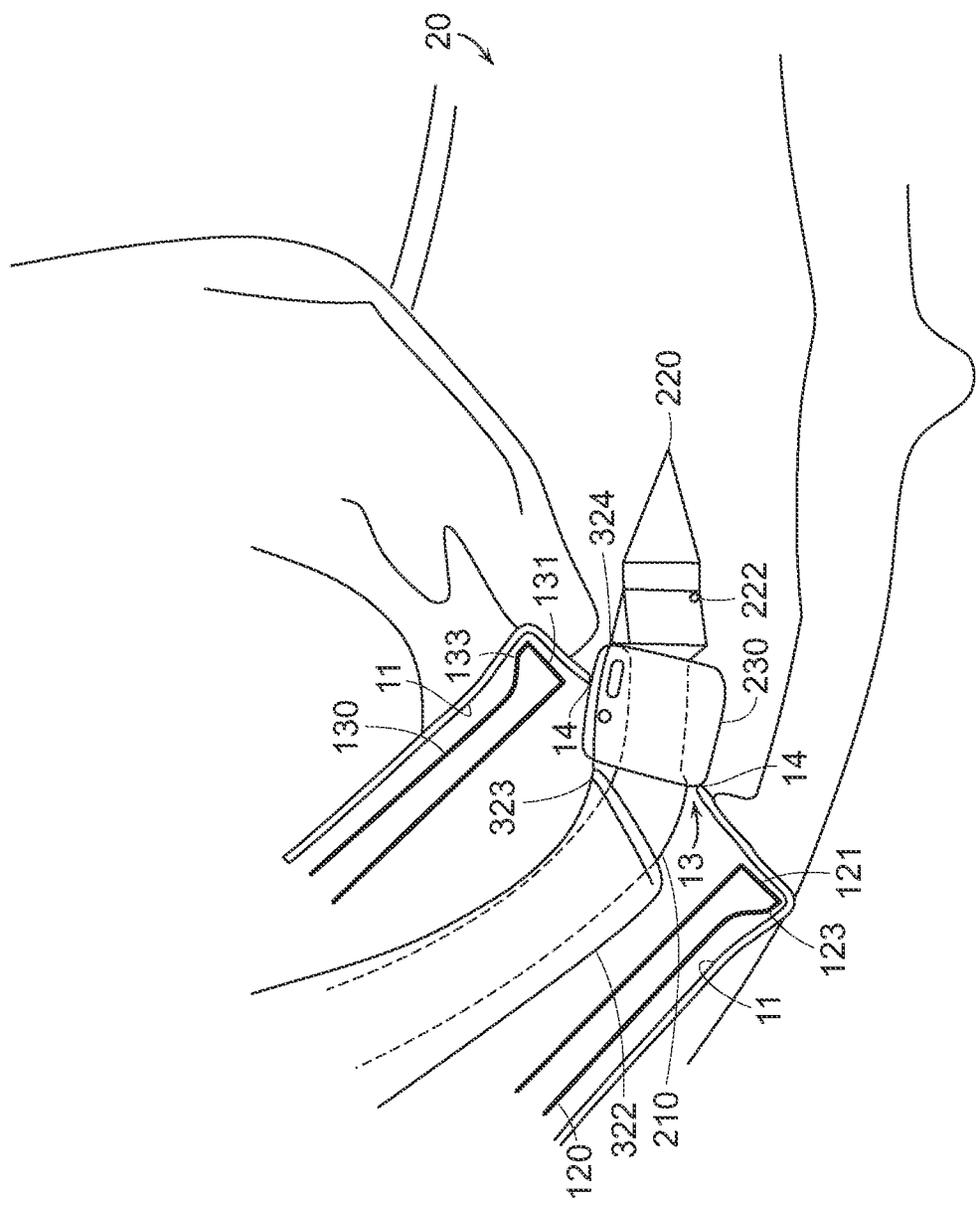

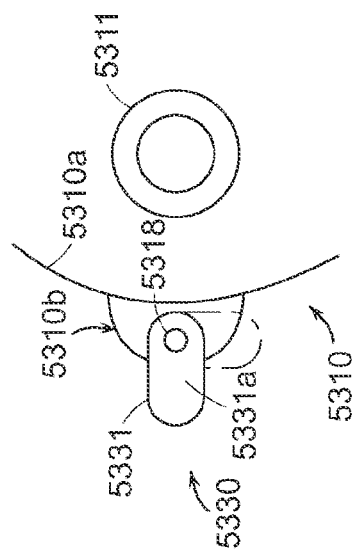
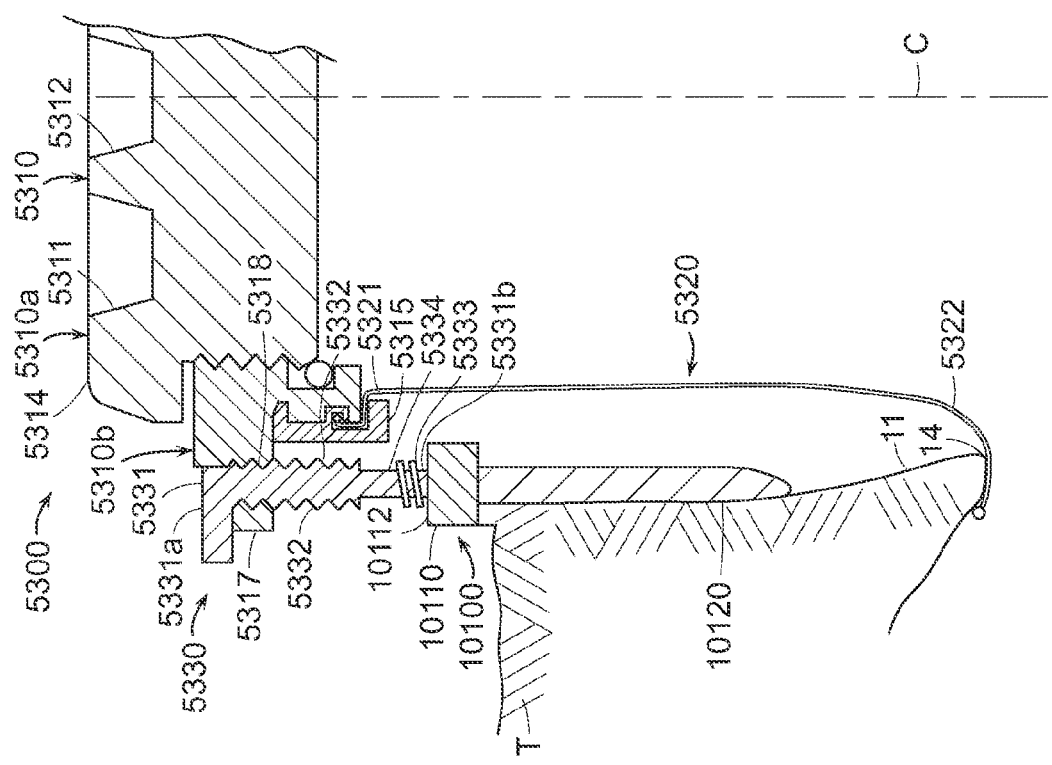

VAGINAL ENTRY SURGICAL DEVICES, KIT, SYSTEM, AND METHOD

BACKGROUND

The embodiments relate, in general, to medical procedures and devices to enter into a patient's body cavity and, more particularly, to devices for establishing at least one conduit into a patient's body cavity through a patient's orifice, such as a patient's vagina, to accomplish various surgical and therapeutic procedures.

Access to the abdominal cavity may, from time to time, be required for diagnostic and therapeutic endeavors for a variety of medical and surgical diseases. Historically, abdominal access has required a formal laparotomy to provide adequate exposure. Such procedures, which require incisions to be made in the abdomen, are not particularly well-suited for patients that may have extensive abdominal scarring from previous procedures, those persons who are morbidly obese, those individuals with abdominal wall infection, and those patients with diminished abdominal wall integrity, such as patients with burns and skin grafting. Other patients simply do not want to have a scar if it can be avoided.

Minimally invasive procedures are desirable because such procedures can reduce pain and provide relatively quick recovery times as compared with conventional open medical procedures. Many minimally invasive procedures are performed with an endoscope (including, without limitation, laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices are often inserted into a patient through trocars placed through the body wall. Trocars must typically pass through several layers of overlapping tissue/muscle before reaching the abdominal cavity.

Still less invasive treatments include those that are performed through insertion of an endoscope through a natural body orifice to a treatment region. Examples of this approach include, but are not limited to, cholecystectomy, appendectomy, cystoscopy, hysteroscopy, esophagogastroduodenoscopy, and colonoscopy. Many of these procedures employ the use of a flexible endoscope during the procedure. Flexible endoscopes often have a flexible, steerable articulating section near the distal end that can be controlled by the user by utilizing controls at the proximal end. Minimally invasive therapeutic procedures to treat diseased tissue by introducing medical instruments to a tissue treatment region through a natural opening of the patient are known as Natural Orifice Translumenal Endoscopic Surgery (NOTES)™. Entry through a natural opening, such as a patient's vagina, for example may further reduce the pain a patient experiences after the procedure because the vaginal walls have less pain receptors than do the abdominal walls.

Some flexible endoscopes are relatively small (about 1 mm to 3 mm in diameter), and may have no integral accessory channel (also called biopsy channels or working channels). Other flexible endoscopes, including gastroscopes and colonoscopes, have integral working channels having a diameter of about 2.0 mm to 3.5 mm for the purpose of introducing and removing medical devices and other accessory devices to perform diagnosis or therapy within the patient. As a result, the accessory devices used by a physician can be limited in size by the diameter of the accessory channel of the scope used. Additionally, the physician may be limited to a single accessory device when using the standard endoscope having one working channel.

Certain specialized endoscopes are available, such as large working channel endoscopes having a working channel of about 5-10 mm in diameter, which can be used to pass relatively large accessories, or to provide capability to suction large blood clots. Other specialized endoscopes include those having two or more working channels. Regardless, using an endoscope alone to perform a surgical procedure may be limiting in that multiple tools may not be easily moved apart from one another to perform a surgical procedure.

The above mentioned minimally invasive surgical procedures have changed some of the major open surgical procedures such as gall bladder removal, or a cholecystectomy, to simple outpatient surgery. Consequently, the patient's return to normal activity has changed from weeks to days. These types of surgeries are often used for repairing defects or for the removal of diseased tissue or organs from areas of the body such as the abdominal cavity.

The foregoing discussion is intended only to illustrate the present field and should not be taken as a disavowal of claim scope.

SUMMARY

In various embodiments, a surgical method is provided for introducing a conduit into a patient's body cavity. In at least one embodiment, the method can comprise inserting a speculum into a patient's vagina, the speculum including two or more blades movable with respect to each other, expanding the speculum by moving the blades apart from each other such that the blades move apart walls of the vagina, obtaining a surgical delivery device coupled to a transorifice device, the transorifice device including a flexible conduit, inserting a portion of the surgical delivery device through the speculum such that a portion of the transorifice device is also inserted through the speculum, creating an incision in the vagina, passing a tip of the surgical delivery device through the incision and into a body cavity of the patient, and releasing the transorifice device from the surgical delivery device such that a distal portion of the flexible conduit is located within the body cavity.

In various embodiments, a speculum is provided. In at least one embodiment, the speculum can comprise a base defining an opening therethrough, a first blade attached to the base, a second blade attached to the base, and at least one locking assembly configured to releasably hold the first blade and the second blade relative to each other in at least one locked position. In these embodiments, the base can comprise a proximal surface, the first blade can comprise a first distal end, and the second blade can comprise a second distal end. Further, in these embodiments, the first blade and the second blade are movable with respect to each other. Moreover, in these embodiments, when the first blade and the second blade are in the at least one locked position, the shortest distance between the first distal end and a plane defined by the proximal surface is substantially equal to the shortest distance between the second distal end and the plane defined by the proximal surface.

In various embodiments, a transorifice device is provided. In at least one embodiment, the transorifice device can comprise a port assembly defining at least one port therein and a flexible conduit extending from the distal side of the port assembly. In these embodiments, the port assembly can include a proximal side and a distal side. Further, in these embodiments, the flexible conduit can include a proximal portion adjacent to the port assembly and a distal portion. Moreover, in these embodiments, the flexible conduit can further comprise a pliable ring located at the distal portion.

In various embodiments, a surgical delivery device is provided. In at least one embodiment, the surgical delivery device can comprise a body including a proximal end and a distal end, a tip movably mounted to the distal end of the body such that the tip can move between an opened position and a closed position, and a balloon surrounding at least part of the body and located adjacent the distal end of the body. In these embodiments, the body can define a tool receiving passageway therein including a proximal opening located at the proximal end and a distal opening located at the distal end.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 9A is an enlarged view of the distal portions of the speculum, the surgical delivery device, and the transorifice device of FIG. 8 after the surgical delivery device has created an incision through the vaginal wall at an otomy site and a balloon of the surgical delivery device has been expanded to dilate the incision and to secure the surgical delivery device within the incision.

FIG. 26A is a side cross-sectional view of a portion of a transorifice device according to a non-limiting embodiment; the transorifice device is shown resting on a speculum after the speculum has been inserted into an orifice to expand tissue walls, an incision has been made in the tissue, and a pliable ring of the transorifice device has been positioned distal to the incision.

FIG. 26B is a top view of a push member of the transorifice device of FIG. 26A inserted through a portion of the transorifice device's port assembly.

DETAILED DESCRIPTION

Figure 1:
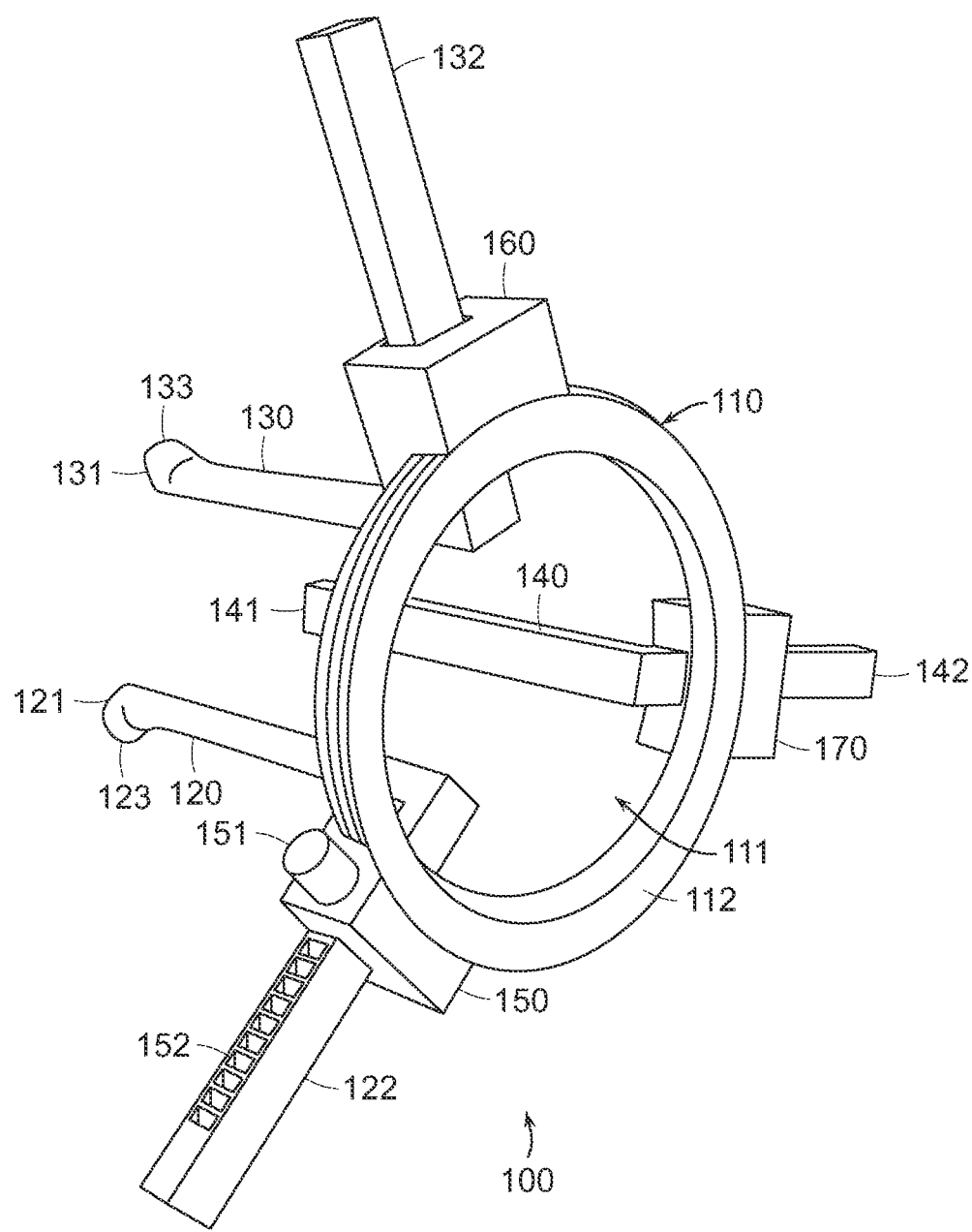
FIG. 1 is a side perspective view of a speculum according to a non-limiting embodiment.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Such modifications and variations are intended to be included within the scope of the appended claims.

In the following description, like reference characters designate like or corresponding parts throughout the several views. Also in the following description, it is to be understood that terms such as "forward," "rearward," "front," "back," "right," "left," "upwardly," "downwardly," "proximally," "distally," and the like are words of convenience and are not to be construed as limiting terms. The description below is for the purpose of describing various embodiments and is not intended to limit the appended claims.

The various embodiments generally relate to various devices, kits, and/or systems for use in connection with endoscopes, including laparoscopes, for performing a surgical procedure or procedures within a patient's body cavity. The terms "endoscopic tools" and "endoscopic surgical instruments" as used herein may comprise, for example, endoscopes, lights, insufflation devices, cleaning devices, suction devices, hole-forming devices, imaging devices, cameras, graspers, clip appliers, loops, Radio Frequency (RF) ablation devices, harmonic ablation devices, scissors, knives, suturing devices, etc. However, such terms are not limited to those specific devices. As the present Description proceeds, those of ordinary skill in the art will appreciate that the unique and novel features of the various instruments and methods for use thereof may be effectively employed to perform surgical procedures by inserting such endoscopic tools through a natural body lumen (e.g., the mouth, anus, and/or vagina) or through a transcutaneous port (e.g., a abdominal trocar, and/or cardiothoracic port) to perform surgical procedures within a body cavity.

The various embodiments described herein are directed to medical devices and, more particularly, to methods and devices which can be useful in minimally invasive endoscopic procedures carried out with an endoscope and/or a similar surgical instrument. Further, the various embodiments can include devices, systems, and/or methods useful in natural orifice translumenal endoscopic surgery ("NOTES") procedures. As noted above, NOTES procedures may be performed transorally, transgastrically, and/or transvaginally. In at least one such embodiment, and referring to FIGS. 1-3, a surgical system or kit may include a speculum 100, a transorifice device 300, and a surgical delivery device 200, each described in more detail below. Alternatively, a kit may comprise one or more of the above instruments. In any event, a kit may also include an enclosure, such as bag or container, to hold the instrument or instruments of the kit.

Briefly, the speculum 100 may be inserted into and serves to enlarge or dilate a patient's orifice, such as a female patient's vagina. The surgical delivery device 200 may perform several functions, such as applying and/or dilating an incision (an otomy) to a tissue wall of the patient and/or assisting in the proper placement and/or sealing of the transorifice device 300 within a body cavity, such as the patient's abdominal cavity. The transorifice device 300, once properly in position, as described below, may provide a flexible conduit from outside the patient, through the patient's orifice, and into the body cavity. Further, the transorifice device 300 may provide multiple tool ports therethrough, enabling multiple surgical instruments to be placed through a single orifice and be positioned independently of one another. Accordingly, a system may be provided that provides for the rapid creation of multiple ports in a natural orifice, such as a patient's vagina, while accommodating anatomical variation to reduce the need to excise additional tissue from the patient.

Figure 4:
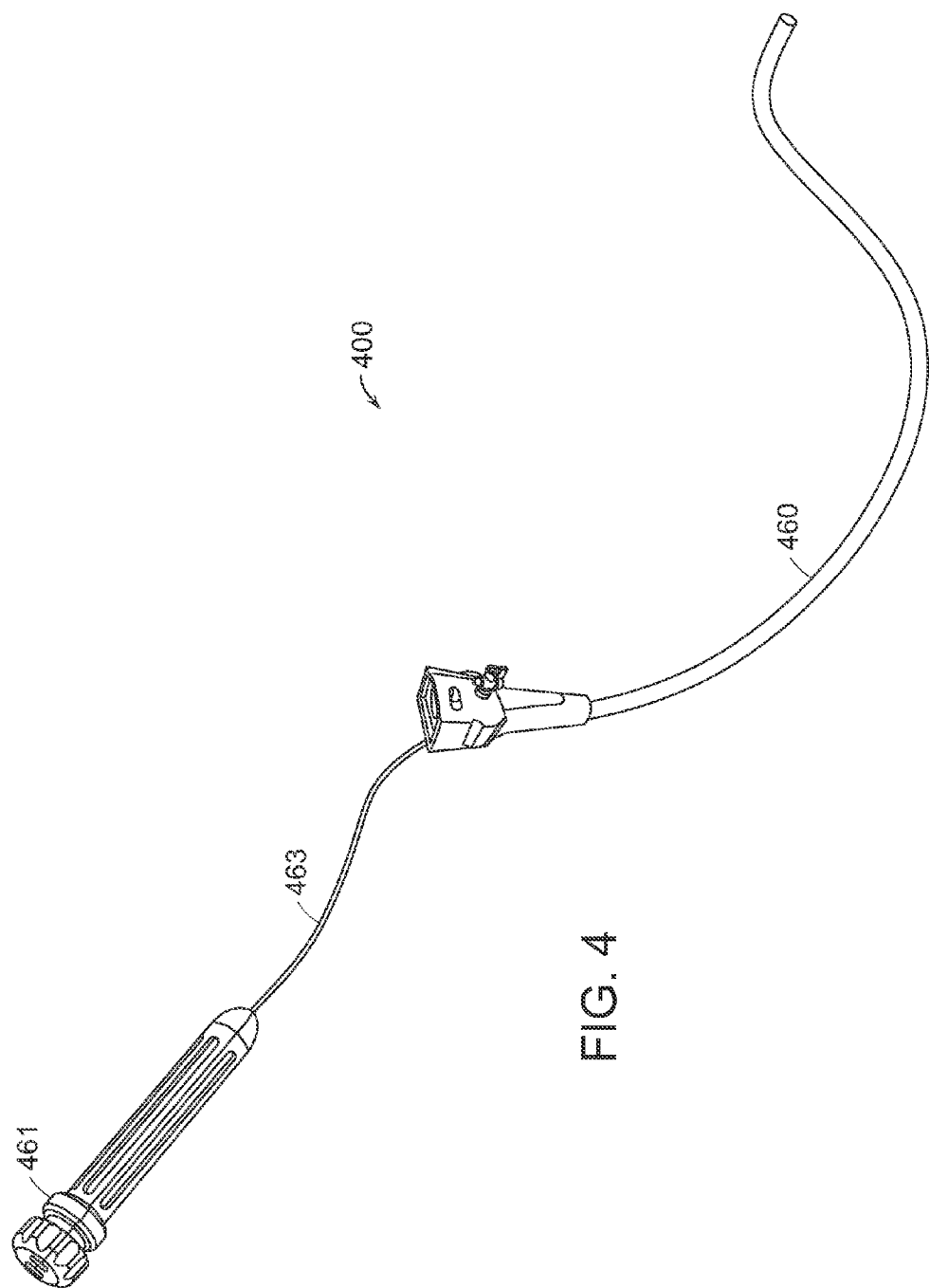
FIG. 4 is a perspective view of a steerable flexible trocar according to a non-limiting embodiment.

Further, in at least one embodiment, referring to FIG. 4, a guide tube or steerable flexible trocar 400 may be provided as part of the system or kit. Such a guide tube or steerable flexible trocar may be as described in U.S. patent application Ser. Nos. 11/894,358 and/or 12/468,462, each entitled "MANIPULATABLE GUIDE SYSTEM AND METHODS FOR NATURAL ORIFICE TRANSLUMENAL ENDOSCOPIC SURGERY," and/or U.S. patent application Ser. Nos. 11/382,173, 11/382,182, 11/382,196, and/or 11/775,477 each entitled ENDOSCOPIC TRANSLUMENAL SURGICAL SYSTEMS, each herein incorporated by reference in their respective entireties. Additionally, in various embodiments, the surgical system or kit may also include or utilize an endoscope for, among other things, visualizing the surgical procedure. At the same or different points of a surgical procedure, such an endoscope may be guided into the patient's body cavity by the transorifice device 300 and/or the steerable flexible trocar 400. These and other embodiments are described in more detail below.

Figure 5A:
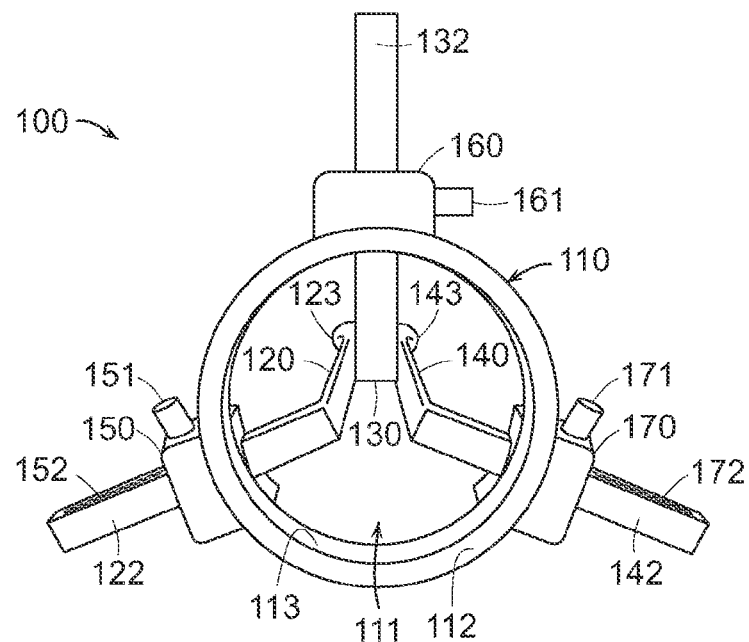
FIG. 5A is a top perspective view of the speculum of FIG. 1 in a closed configuration.
Figure 5B:
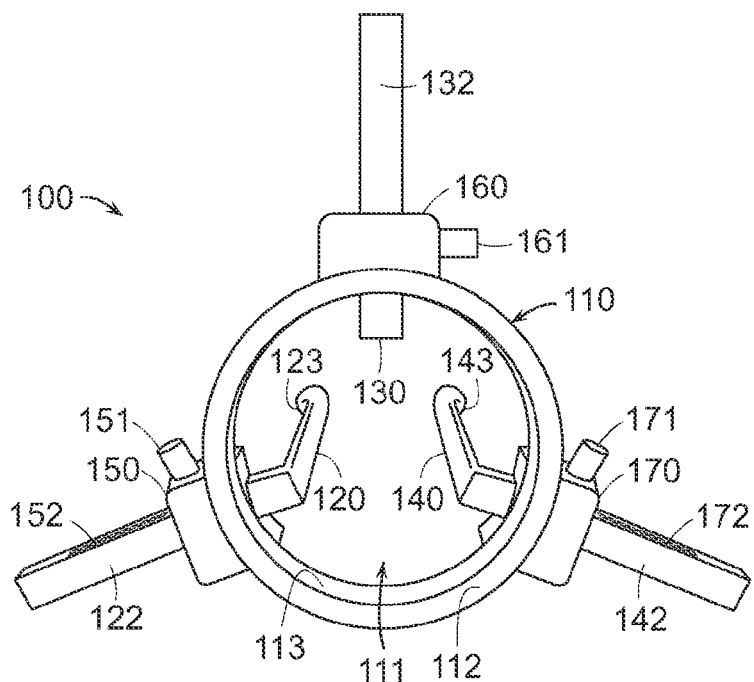
FIG. 5B is a top perspective view of the speculum of FIG. 1 in an opened configuration.
Figure 6A:
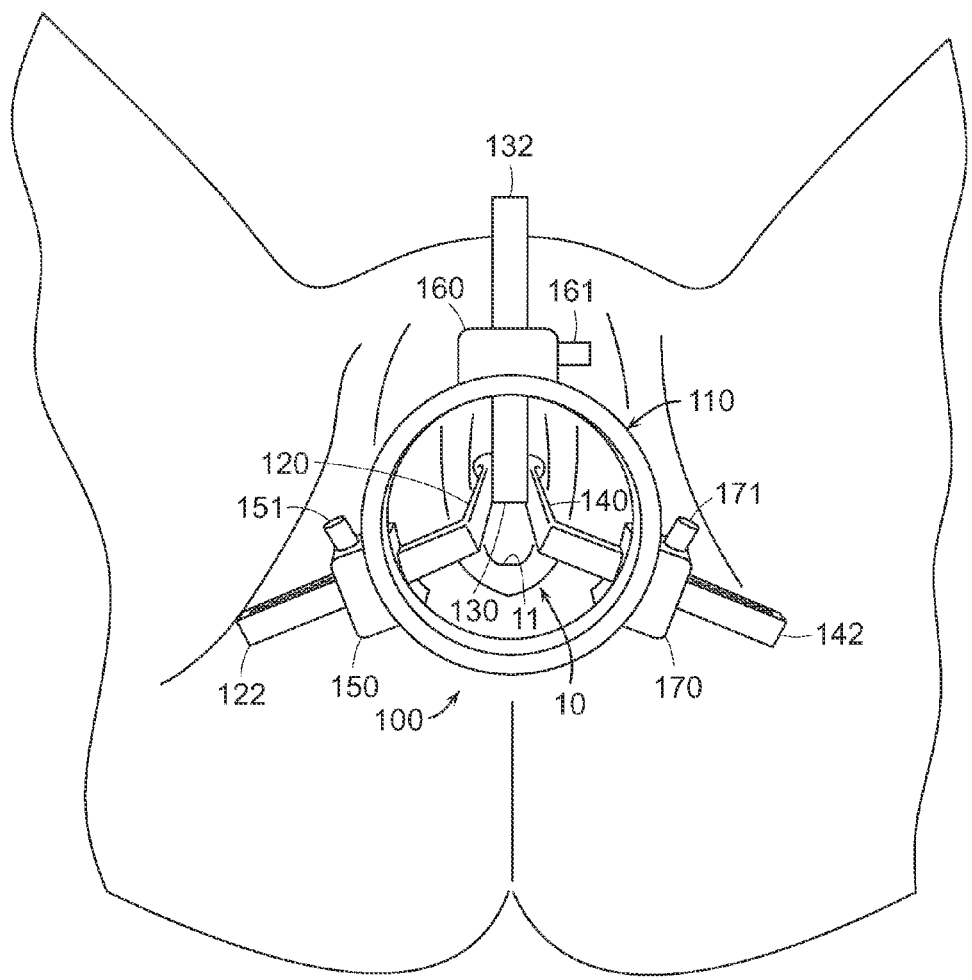
FIG. 6A illustrates the speculum of FIG. 1 in a closed configuration being inserted into a patient's vagina.
Figure 6B:
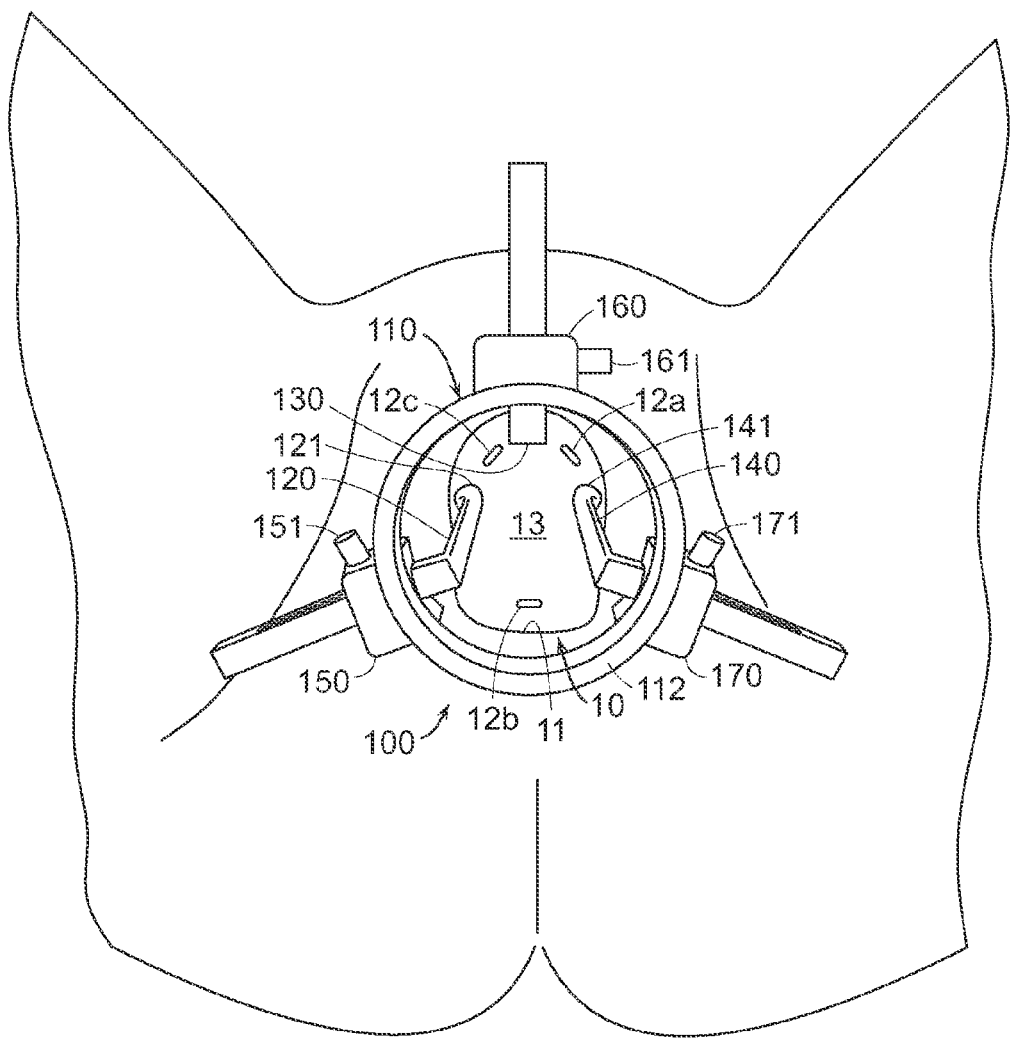
FIG. 6B illustrates the speculum of FIG. 1 in an opened configuration after being inserted into a patient's vagina, as well as sutures applied to the vaginal walls between blades of the speculum to identify an otomy site.

Focusing now on at least one non-limiting embodiment, a NOTES system is provided for vaginal entry. Referring to FIGS. 6A-6B, in such embodiments, a vaginal speculum 100, for example, may be at least partially inserted into a patient's vagina 10 (FIGS. 6A and 6B) to expand the vaginal walls 11 and provide access to an otomy site 13 therein. As seen in FIGS. 1 and 5A-5B, the speculum 100 may comprise a base 110 defining an opening 111 therethrough. For example, in at least one embodiment, the base may be annular in shape and comprise an inner wall 113 which may define the opening 111. Also, the base 110 may comprise a proximal surface 112 which, as described below, may serve as a support surface for at least one other component of the system.

Further, the speculum 100 may comprise at least two blades, a first blade 120 attached to the base 110 and a second blade 130 also attached to the base 110. Referring to FIGS. 5A and 6A, the blades 120, 130 may be movable with respect to each other such that they may be moved together, or closed, for insertion into the patient's vagina 10 (see FIG. 6A). Referring to FIGS. 5B and 6B, once inserted, the blades 120, 130 may be moved away from each other, or expanded, to stretch, expand, move, or otherwise spread apart the vaginal walls 11 (see FIG. 6B). Also, referring again to FIG. 6B, in the illustrated embodiment, the speculum 100 may further comprise a third blade 140 attached to the base, which may assist in creating a more uniform expanded state of the vaginal walls 13 and reduce the localized stress experience by the vaginal walls 13 where they contact the speculum blades 120, 130, 140. While the present embodiment discloses a speculum 100 including three blades 120, 130, 140, alternatively, in various embodiments, more than three blades may be included in a speculum. As will be appreciated, increasing the number of speculum blades may increase the working area available to a user therebetween and provide various other advantages, such as the reduction of stress experienced by tissue at each blade.

Referring to FIG. 1, the first blade 120 may include a first distal end 121, the second blade 130 may include a second distal end 131, and the third blade 140 may include a third distal end 141, each of which may be configured for insertion into a patient's vagina, as described below. In at least one embodiment, and for reasons explained in more detail below, each blade 120, 130, 140 may be the same length, as measured from the base 110, to each one's distal end 121, 131, 141, for example.

Additionally, the speculum may comprise at least one locking assembly configured to releasably hold the first blade and the second blade relative to each other in at least one locked position. Referring to FIGS. 1 and 5A-5B, in one exemplary embodiment, the locking assemblies may comprise a first ratchet assembly 150 operably engaged with the first blade 120, a second ratchet assembly 160 operably engaged with the second blade 130, and a third ratchet assembly 170 operably engaged with the third blade 140.

In more detail, referring to FIGS. 5A-5B, the first ratchet assembly 150 may comprise a pawl (not shown) that is biased, by a spring or otherwise, against detents, such as first angled teeth 152, formed in or attached to a first support bar 122. The support bar 122 may be linear, or straight, in shape and may be integrally formed with or attached to first blade 120. In any event, the first ratchet assembly 150 is configured to permit the first blade 120 to move away from second blade 130 and/or third blade 140 while preventing or resisting the movement of first blade 120 toward second blade 130 and/or third blade 140. Further, owing to friction between the pawl and the teeth 152, the first blade 120 may further resist free motion away from second blade 130 and/or third blade 140 while the pawl is engaged with the teeth 152. In other words, while the blade 120 may be pushed or pulled readily away from the other blades 130, 140, the first blade 120 may not move away from the other blades 130, 140 on its own accord, i.e., without a user applying a force to blade 120. However, the opposite motion, moving the first blade 120 toward the other blades 130, 140, is generally prevented by the pawl engaging angled teeth 152. The pawl may be disengaged from the teeth 152 by pushing, pulling, twisting, and/or otherwise operating a first button 151 which is operably coupled to the pawl. Accordingly, when a user operates the button 151, the first ratchet assembly 150 may allow the first blade 120 to move freely toward the second blade 130 and/or third blade 140. In various embodiments, the button 151 may be locked into an open position such that the pawl is disengaged from the teeth 152 temporarily even if a user removes his or her finger(s) from the button 151. In such embodiments, the blade 120 may then be moved freely to a desired position, after which the button may be unlocked to a closed position such that the respective pawl reengages the teeth 152 and resists movement of the blade 120, as described above.

Still referring to FIGS. 5A-5B, the second ratchet assembly 160 and the third ratchet assembly 170 may be similar to the first ratchet assembly 150 in that each may comprise a pawl (not shown) that is biased against second angled teeth (not shown) and third angled teeth 172 formed in or attached to a second support bar 132 and a third support bar 142, respectively. The support bars 132, 142, like first support bar 122, may be linear in shape and may be integrally formed with or attached to second blade 130 and third blade 140, respectively. Thus, the second ratchet assembly 160 is configured to permit the second blade 130 to move away from first blade 120 and/or third blade 140 while preventing or resisting the movement of second blade 130 toward first blade 120 and/or third blade 140. Likewise, the third ratchet assembly is configured to permit the third blade 140 to move away from first blade 120 and/or second blade 130 while preventing or resisting the movement of third blade 140 toward first blade 120 and/or second blade 130. Further, owing to friction between the respective pawls and teeth, the second blade 130 and/or the third blade 140 may further resist free motion away from the other blades 120, 140 or 120, 130, respectively, while each pawl is engaged with its associated teeth. In other words, while the blades 130, 140 may be pushed or pulled readily away from the other blades 120, 140 or 120, 130, respectively, the second blade 130 and/or third blade 140 may not move away from the other blades 120, 140 or 120, 130, respectively, on its own accord, i.e., without a user applying a force to either or both of blades 130, 140. However, the opposite motion, moving the second blade 130 and/or third blade 140 toward the other blades 120, 140 or 120, 130, respectively, is generally prevented by each pawl engaging its associated angled teeth.

Each pawl of ratchet assemblies 160, 170 may be disengaged from the second angled teeth and/or third angled teeth 172 by pushing, pulling, twisting, and/or otherwise operating a second button 161 and/or third button 171 which are each operably coupled to their respective pawls. Accordingly, when a user operates the second button 161, the second ratchet assembly 160 may allow the second blade 130 to move freely toward the first blade 120 and/or third blade 140. Likewise, when a user operates the third button 171, the third ratchet assembly 170 may allow the third blade 140 to move freely toward the first blade 120 and/or second blade 130. In various embodiments, the buttons 161, 171 may each be locked into an open position such that each one's associated pawl is disengaged from teeth 162, 172 temporarily even if a user removes his or her finger(s) from the button 161 and/or 171. In such embodiments, the blades 130 and/or 140 may then be moved freely to a desired position, after which the button may be unlocked to a closed position such that the respective pawl reengages the teeth 162 or 172 and resists movement of the blade 130 and/or 140, as described above. Also, in various embodiments, although not illustrated, the pawl of each ratchet assembly 150, 160, 170 may be contained within each assembly 150, 160, 170, through which a portion of support bar 122, 132, 142 and thus teeth 152, 162, 172 may pass to engage each pawl, respectively.

Thus, in the illustrated embodiment of FIGS. 5A-5B, the locking assemblies, e.g., first ratchet assembly 150, second ratchet assembly 160, and third ratchet assembly 170 may be configured to releasably hold the first blade 120, the second blade 130, and/or the third blade 140, respectively, relative to each other in at least one locked position. An exemplary, first locked position is shown in FIG. 5A, where the blades 120, 130, 140 are held closely together, but are prevented from completely moving together because of the ratchet assemblies 150, 160, 170. Further, the locking assemblies may be configured to releasably hold the first blade 120, the second blade 130, and/or the third blade 140 relative to each other in at least two locked positions. An exemplary, second locked position is shown in FIG. 5B, where the blades 120, 130, 140 have been moved apart from the first locked position shown in FIG. 5A. Accordingly, in the second locked position of FIG. 5B, the blades 120, 130, 140 are releasably held apart by ratchet assemblies 150, 160, 170, as described above. Additionally, each blade 120, 130, and 140 may be independently moved to any position between that shown in FIG. 5A and that of FIG. 5B. Further, each blade 120, 130, and/or 140 may be moved to any position within or beyond that shown in FIGS. 5A-5B that the respective support bar 122, 132, or 142 permits. Accordingly, varying vaginal wall dimensions, shapes, and contours can be appropriately engaged by the independent three blade speculum 100 shown in FIGS. 5A-5B.

According to at least one embodiment, a vaginal speculum may be inserted into a patient's vagina and expanded to create access to a desired incision, or otomy, site. By way of example and referring to FIGS. 5A and 6A-6B, speculum 100 may be first closed to an entry position by moving the blades 120, 130, 140 close together, see FIG. 5A. This may be accomplished, as explained above, by operating first button 151 of first ratchet assembly 150 while simultaneously pushing or pulling first blade 120 or support bar 122 such that blade 120 moves towards the other blades 130, 140. This may be likewise repeated for the second blade 130 and the third blade 140 until all of the blades 120, 130, 140 are close together or touching each other. It will be appreciated that any order of moving the blades 120, 130, 140 may accomplish the same goal of bringing the blades together into the closed position as shown in FIG. 5A. Further, where the buttons 151, 161, and 171 are lockable into an open position, as described above, the buttons may be locked open and then each blade 120, 130, 140 may be brought together with at least one other blade or all three blades 120, 130, and 140 may be brought together simultaneously; thereafter, in such embodiments, the buttons 151, 161, 171 may then be unlocked to allow the respective ratchet assemblies 150, 160, 170 to function as discussed above.

Referring now to FIG. 6A, after closing the speculum 100 to the position shown in FIG. 5A, the blades 120, 130, 140 may then be inserted into the patient's vagina 10 until the blades reach a desired depth therein. In at least one embodiment, and as shown in FIG. 6A, the blades 120, 130, 140 may be inserted until at least one of the base 110, the ratchet assemblies 150, 160, 170, and the support bars 122, 132, 142 contact the patient's exterior. Thereafter, as discussed in more detail below, a user can know how deep the blades 120, 130, 140, and their distal ends 121, 131, 141 (see FIG. 1) extend into the patient.

Next, referring to FIG. 6B, the blades 120, 130, 140 are moved away from each other to cause the blades to contact and press against the vaginal walls 11 such that the same expand, stretch, or otherwise spread apart to reveal an otomy site 13. While the walls 11 may resist such movement, the blades 120, 130, 140 are held in the illustrated open position owing to the ratchet assemblies 150, 160, 170, as discussed above. After the applicable surgical procedure is completed, the speculum 100 may be closed by releasing each ratchet assembly via buttons 151, 161, 171 such that the blades 120, 130, 140 may be moved close together and the speculum 100 removed from the patient's vagina 10.

Notably, the first, second, and/or third blades, 120, 130, 140 may be moved with respect to each other without a handle. As used herein, a handle includes a part made specifically to be grasped or held by the hand. In traditional speculums, the blades are typically operated by manipulating at least one handle that is grasped by a user. However, various embodiments herein do not require a handle and thus maximize the working area available around the speculum 100 such that additional instruments, such as a surgical delivery device 200 (FIG. 2), a transorifice device 300 (FIG. 3.), a steerable flexible trocar 400 (FIG. 4), various endoscopic devices, and/or other surgical tools may be inserted and operated therethrough with minimal or no hindrance from the speculum 100.

Still referring to FIG. 6B, after opening the speculum 100, sutures 12a, 12b, and 12c may be stitched into the vaginal walls 11, between the blades 120, 130, 140, using known surgical techniques. Doing such allows the walls to be drawn to make the otomy site 13 in the vaginal walls 11 taught between the first distal end 121, the second distal end (not shown in FIG. 6B; see end 131 in FIG. 1, for example), and the third distal end 141, of the first, second, and third blades 120, 130, 140, respectively. Further, the sutures 12a, 12b, 12c may be secured, at one end, to the base 110 of the speculum 100 and at another end, to the vaginal walls 11. Accordingly, in such embodiments, the sutures may be tightened to create a drum-like effect on the tissue between the distal ends of the blades 120, 130, 140.

Further, as noted above, owing to the uniform length of each blade 120, 130, 140, the depth that each blade's distal end 121, 131, 141 (see FIG. 1) may extend into the patent is made known when a non-blade part of the speculum 100 contacts the patient's exterior. Accordingly, between the known depth of the distal ends 121, 131, 141 and/or the drawn taught otomy site 13, anatomical variations between many patients' vaginal dimensions, shapes, and contours can be removed as a significant variable during the surgical procedure.

Additionally, as will become evident from the disclosure which follows below, the proximal surface 112 of the base 110 may serve as a support surface for at least one additional surgical device of a surgical system, for example, for a transorifice device 300 (see FIGS. 3 and 11). Thus, referring briefly to FIG. 1, and as discussed in more detail below, the speculum 100 may provide that, at least when the ratchet assemblies 150, 160, 170 are locked such that the blades 120, 130, 140 are in a locked position as shown, a shortest distance between the first distal end 121 of blade 120 and a plane defined by the proximal surface 112 may be substantially equal to another shortest distance between the second distal end 131 of blade 130 and the plane defined by the proximal surface 112. Likewise, in such situations, the shortest distance between the first or second distal end 121, 131 may be substantially equal to the shortest distance between the third distal end 141 of blade 140 and the proximal surface 112. It follows that, in such situations, the shortest distances between each of the first, second, and third distal ends 121, 131, 141 and the proximal surface 112 may also be substantially equal therebetween. Accordingly, the proximal surface 112 of base 110 may serve as a support surface for another surgical device, where the entrance to the body, through taught otomy site 13, is at a known distance past the proximal surface 112, thereby alleviating at least one potentially unknown variable from the surgical procedure. Alternatively, the distances from the proximal surface 112 to each distal blade end 121, 131, 141 may be different to accommodate varying angles per patient anatomy or as otherwise desired.

Figure 2:
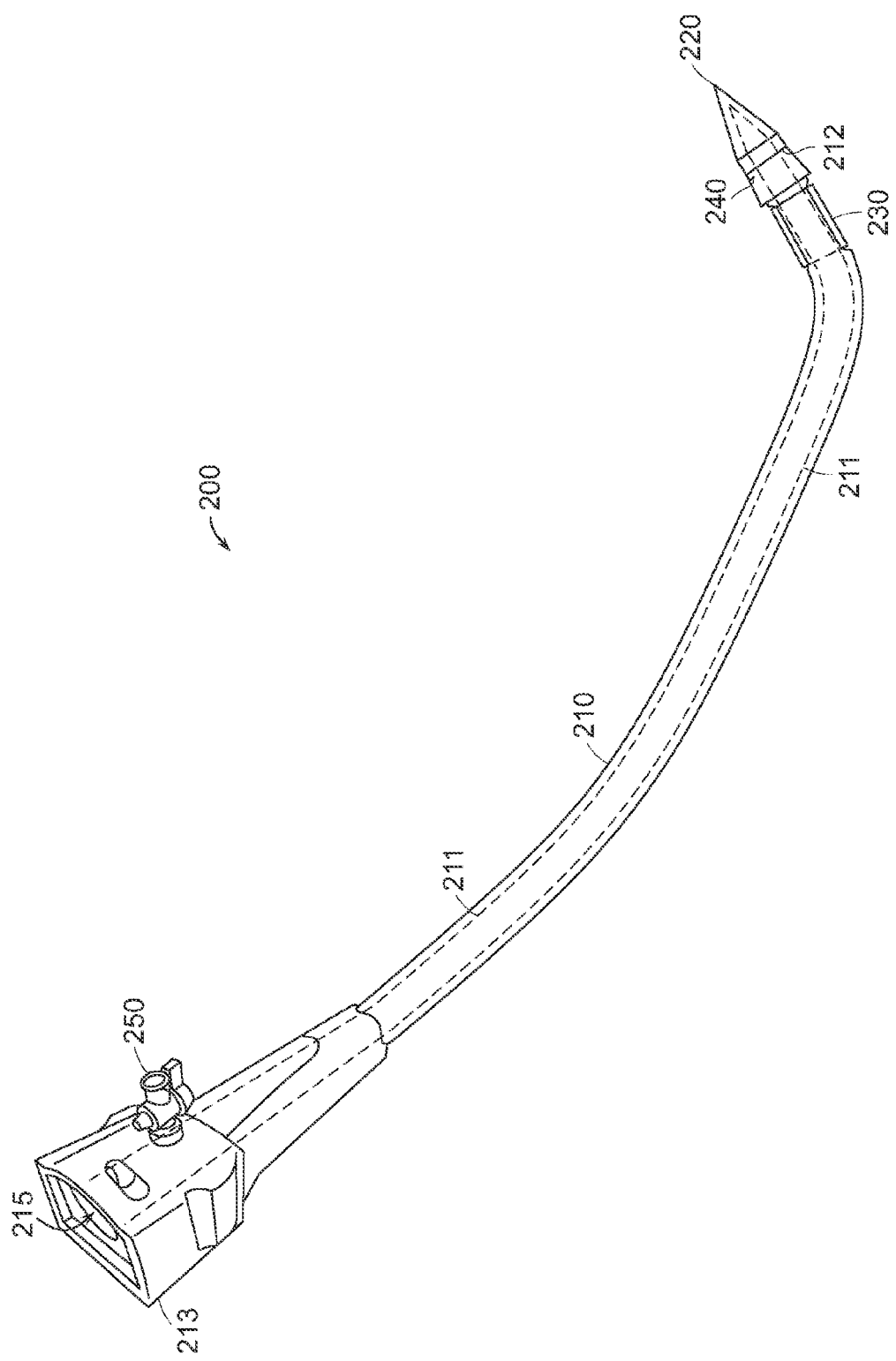
FIG. 2 is a perspective view of a surgical delivery device according to a non-limiting embodiment.
Figure 3:
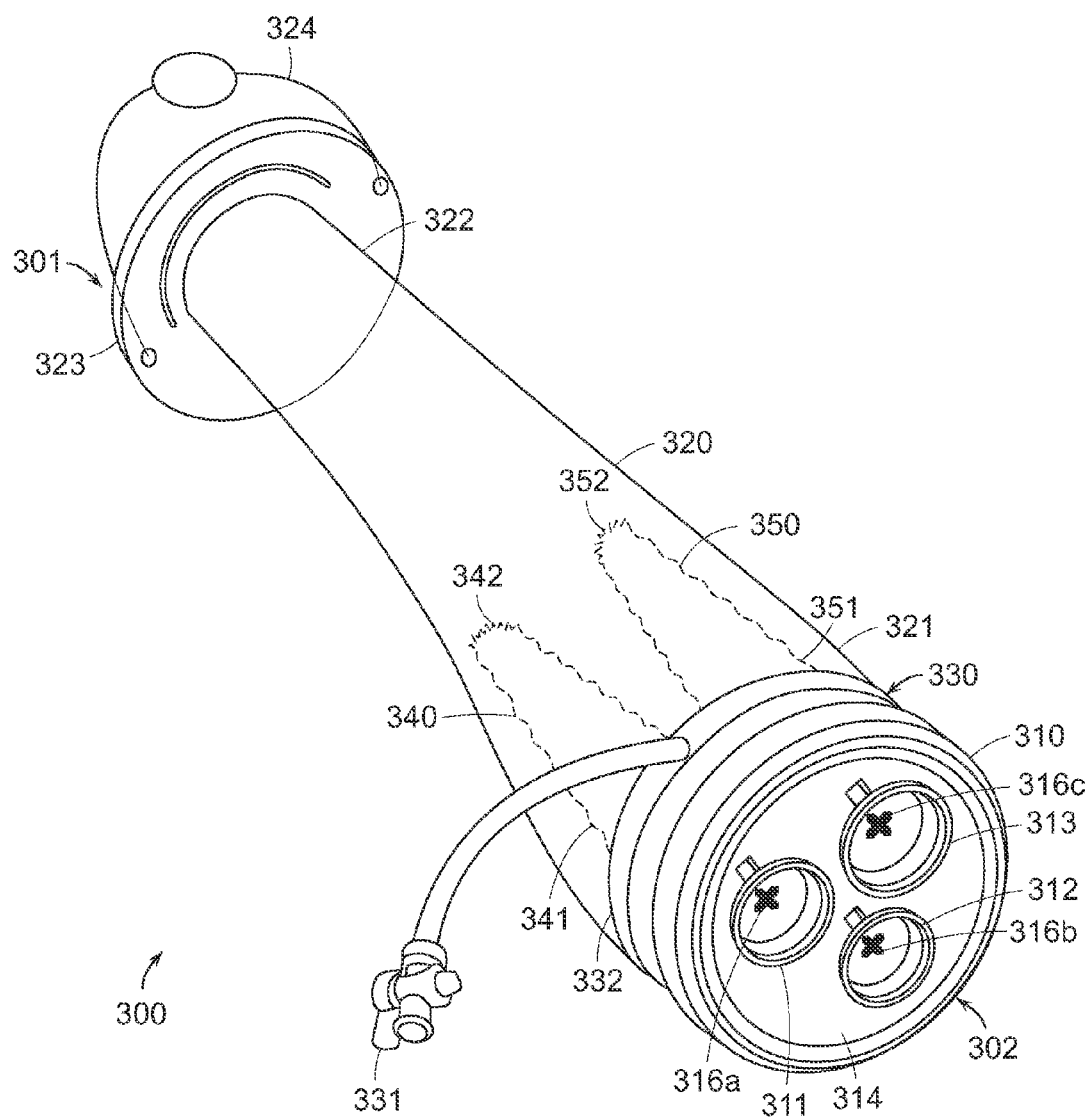
FIG. 3 is a perspective view of a transorifice device according to a non-limiting embodiment.

Referring to FIGS. 1-3, after a speculum, such as speculum 100, is inserted into a patient and expanded, a transorifice device, such as transorifice device 300 may be introduced into the patient to create a conduit and/or multiple ports through a single orifice from outside the patient to a body cavity within the patient. Accordingly, in various embodiments, a surgical delivery device, such as surgical delivery device 200 may be used to deliver and/or position the transorifice device 300 through speculum 100 and into a body cavity of the patient, such as the peritoneal cavity 20, see FIG. 8.

In various embodiments, referring to FIG. 2, the surgical delivery device 200 may comprise a body 210, a tip 220, and an expandable member or balloon 230. The tip 220 and balloon 230 will be explained in more detail below. Focusing now on the body 210, the body 210 may include a proximal end 213 and a distal end 212. The body 210 may also define a tool receiving passageway 211 (shown in dotted lines) therein including a proximal opening 215 located at the proximal end 213 and a distal opening 214 (see FIG. 9B, for example) located at the distal end 212. In other words, referring briefly to FIG. 10, for example, the passageway 211 may extend between the proximal opening 215 and the distal opening 214 of the body 210. Accordingly, the body may provide guidance and/or support to a surgical tool inserted therethrough. By way of example, referring to FIG. 7, the surgical delivery device 200 may receive, via proximal opening 215, a tube-like portion 502 of an endoscope 500. Such endoscopes are well known in the field and may also include a control handle 501 connected to the tube like portion 502.

Further, in various embodiments, the body 210 may be rigid. For example, in at least one such embodiment, the rigid body 210 may be made, at least partially, from aluminum or any other suitable metal or other rigid material. Additionally, such a rigid body 210 may define at least one curve corresponding to the passageway 211. For instance, referring to FIG. 2, the rigid body 210 defines at least one curve that matches that of the passageway 211; in FIG. 2, the rigid body 210 is curved upwards, from the left side of the figure, to the right, such that an instrument inserted into proximal opening 215 will be guided down and then up at a different angle at or near distal end 212 than that at which it was inserted at or near proximal end 214.

Referring back to FIG. 2 and focusing now on the tip 220, the surgical delivery device 200 may further comprise a tip 220 movably mounted to the distal end 213 of the body 210 such that the tip 220 can move between an opened position and a closed position. For example, the tip 220 is shown in a closed position in FIG. 9A and the tip is shown in an opened position in FIG. 9B. As explained in more detail below, the tip may conceal a portion of a surgical tool (e.g., endoscope 500 seen in FIG. 7), that is inserted into passageway 211, such that the tool may be revealed and/or delivered to a body cavity within a patient, such as peritoneal cavity 20, see, e.g., FIG. 10.

The tip 220 may be mounted to the distal end 213 of the body 210 in various ways. For example, referring to FIGS. 9A-9B, the tip 220 may be mounted to the distal end 213 by a hinge 222. Accordingly, the tip may move between a closed position (FIG. 9B) and an opened position (FIG. 9A) by rotating about a pivot point defined by hinge 222. Thus, a distal end 503 of an endoscope 500 may be concealed within surgical delivery device 220, with the tip 220 in a closed position, until the tip 220 is at a desired location within a patient, and then the tip 220 may be moved from the closed position seen in FIG. 9A to the open position seen in FIGS. 9B and 10 by advancing the tube-like portion 502 of the endoscope 500 into the surgical delivery device such that the endoscope's distal end 503 pushes the tip 220 open.

Other configurations are possible to allow an endoscope or other surgical tool to protrude through a surgical delivery device. By way of example, in at least one embodiment, a tip of a surgical delivery device may comprise at least one cantilevered arm (not shown). For instance, the tip may include multiple cantilevered arms that are attached to the distal end of the delivery device's body. The cantilevered arms may be biased towards each other to form a closed configuration. Then arms may come together at the distal most point, or the apex, of the tip in a petal-like arrangement. Pressing a distal end of an endoscope against the arms may allow the cantilevered arms to bend away from each other to an opened position and the endoscope to advance beyond the tip. Pulling the endoscope back into the passageway of the surgical delivery device may permit the cantilevered arms to move back towards each other to a closed position. A person skilled in the art will appreciate that the tip can have a variety of configurations to facilitate its opening and closing.

In various embodiments, referring to FIGS. 7-10, the tip 220 may comprise a material that is at least partially transparent to facilitate viewing therethrough. For example, at least a portion or all of the tip 220 may be transparent or clear to allow an image gathering unit at a distal end 503 (see FIG.

10) of the endoscope 500 to view and gather images through the tip 220. This can allow an endoscope 500 to be used to guide the surgical delivery device 200 through a body lumen, such as vagina 10 (see FIG. 6B), and through tissue. The particular configuration of the transparent portion can vary in order to further facilitate viewing through the tip. For example, the materials and shape can be optimized to provide a smooth, clear viewing surface through which the endoscope 500 can view and gather images. Exemplary tip shapes are provided in U.S. patent application Ser. Nos. 11/382,173, 11/382,182, 11/382,196, and/or 11/775,477 each entitled ENDOSCOPIC TRANSLUMENAL SURGICAL SYSTEMS, noted above. A person skilled in the art will appreciate that the tip 220 can have a variety of configurations to facilitate viewing therethrough.

In various embodiments, a tip of a surgical delivery device, such as tip 220 may be configured to incise tissue. For example, referring to FIG. 2, in at least one embodiment, the tip 220 may taper to a point, such that tissue may be cut or incised when tip 220 is pressed against the tissue, such as the tissue at otomy site 13, seen in FIG. 6B.

Figure 8:
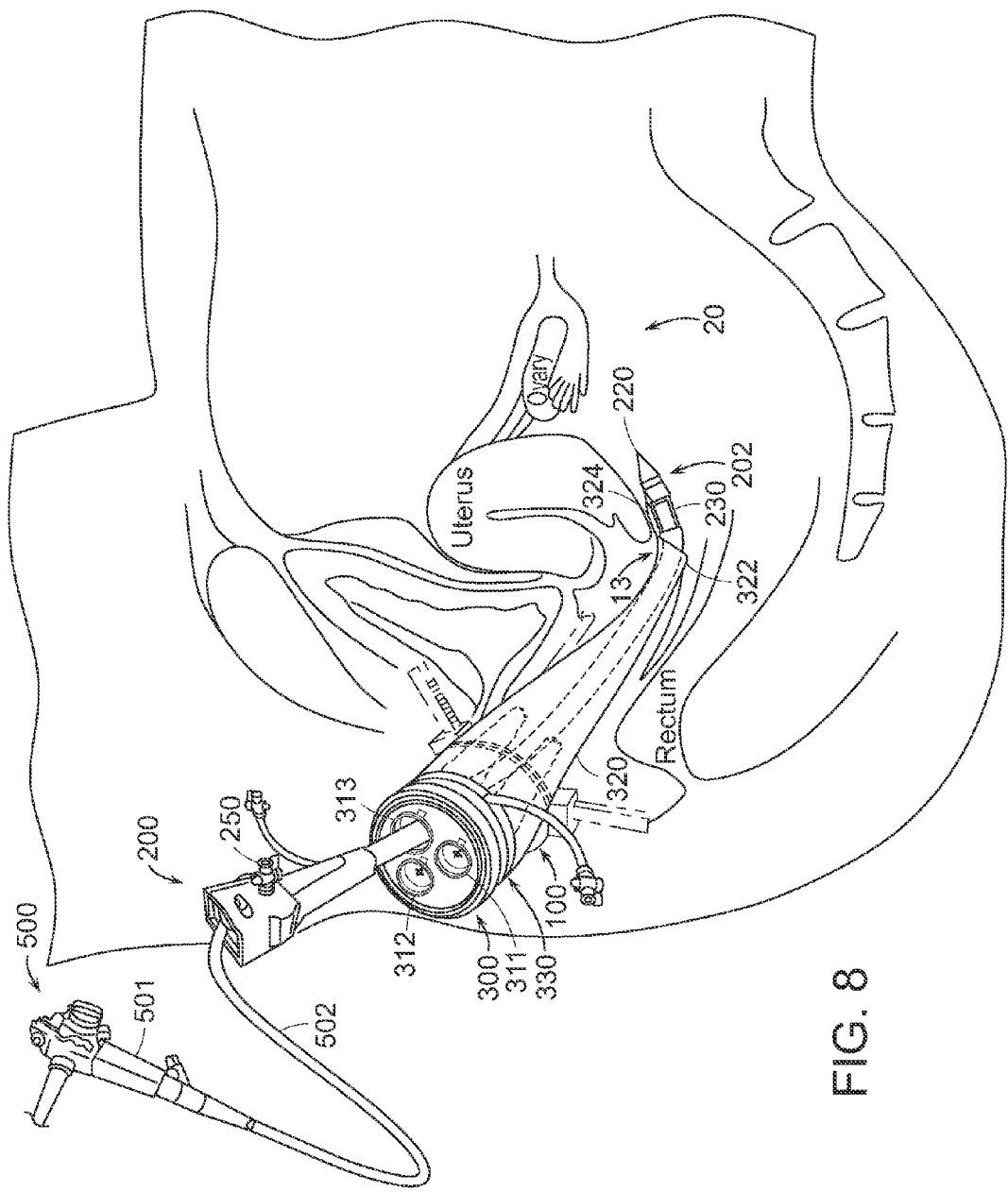
FIG. 8 illustrates the surgical delivery device, the transorifice device, and the endoscope of FIG. 7 inserted through the opened speculum of FIG. 6B, through the patient's vagina, and into a body cavity via an incision created at an otomy site in the vaginal walls; the speculum is shown in dashed lines for visualization purposes.

Accordingly, in various embodiments and referring to FIGS. 6B and 8, after speculum 100 is positioned within vagina 10 and opened to a locked configuration as shown in FIG. 6B, and/or sutures 12a, 12b, and 12c, for example, have been added to draw the otomy site 13 taught, as discussed above, the tip 220 of surgical delivery device 200 may be placed against a patient's tissue, e.g., the vaginal walls 11 at otomy site 13, and pressed to cause the tissue to be cut or incised by the tip 220. Alternatively, the tip 220 may be blunt or otherwise dull and another instrument, such as a needle or knife may be used to make an incision. In any event, because the vaginal walls 11 are relatively thin and/or are drawn taught by the sutures 12a, 12b, 12c and/or speculum blades 120, 130, 140, the vaginal tissue may be slightly raised by tip 220 in a tent-like fashion until the vaginal walls 11 fall away or are otherwise cut such that the tip 220 does not protrude too far into the patient, thereby reducing the probability that the tip 220 may cut or damage any other tissue within the patient.

Figure 9B:
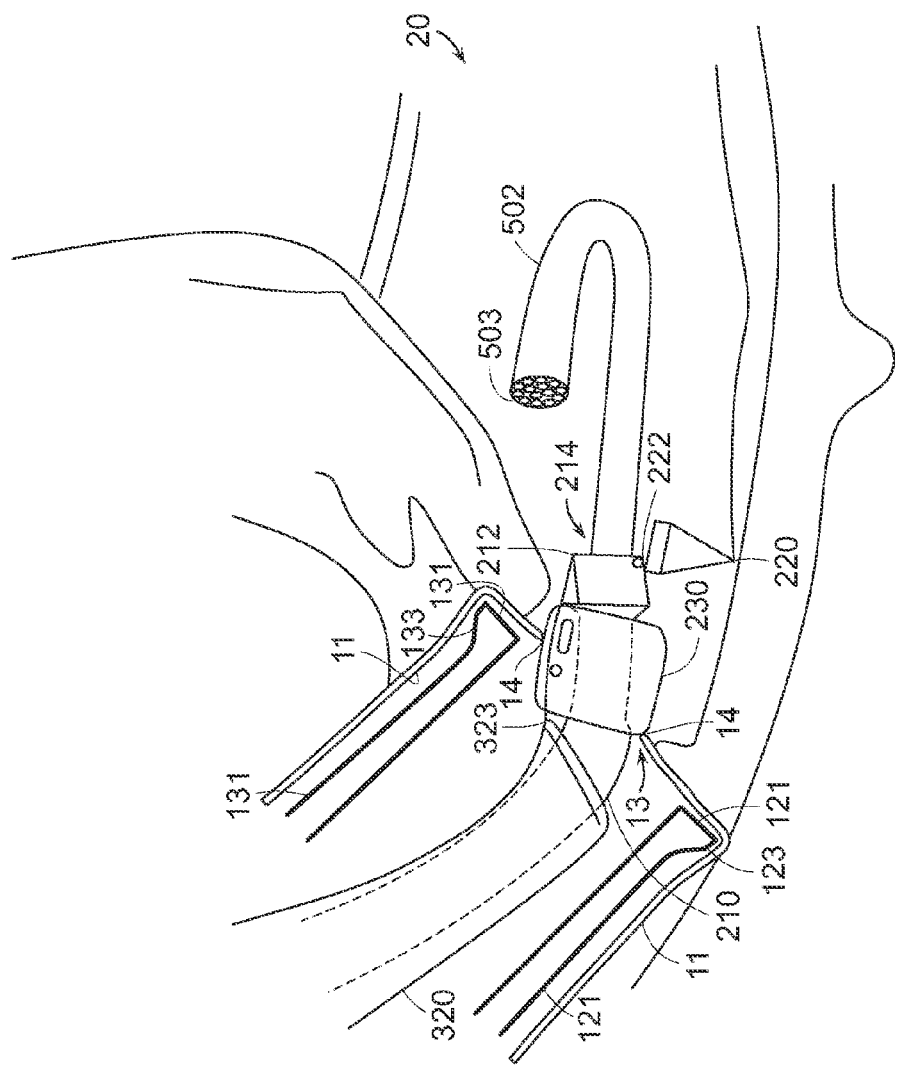
FIG. 9B illustrates the distal portions of the speculum, the surgical delivery device, and the transorifice device of FIG. 9A after a distal portion of the endoscope has been passed through the surgical delivery device to inspect the body cavity and/or otomy site.

Referring now to FIGS. 9A-9B, after inserting the surgical delivery device 200 through an incision 14 at otomy site 13 in vaginal walls 11, the delivery device 200 may further dilate the incision 14 to provide for at least one other surgical instrument to enter body cavity 20. In at least one embodiment, the incision 14 may be dilated by advancing the delivery device 200 through the incision 14 such that the tissue, e.g., vaginal walls 11, dilate or are otherwise stretched apart. Further, in at least one embodiment and as shown in FIGS. 9A-9B, the incision 14 may be dilated by expanding a balloon 230. As mentioned above, the surgical device 200 may also comprise balloon 230. Balloon 230 may surround at least part of the body 210 and may be located adjacent the distal end 212 of the body 210. The balloon 230 is shown in an unexpanded and/or deflated configuration in FIGS. 7-8 and in an expanded and/or inflated configuration in FIGS. 9A-9B, for example. Accordingly, in at least one embodiment, after advancing the tip 220 sufficiently into body cavity 20, the balloon may be expanded. In at least one embodiment, referring to FIG. 8, the balloon 230 may be inflated by providing a gas, such as air (e.g., from a syringe), nitrogen, and/or carbon dioxide, through a port 250 operably coupled to the body 210. Alternatively, a liquid, or a liquid mixed with a gas, may be used to expand the balloon 230 through port 250. The port 250 may include a stopcock valve to maintain gas and/or liquid pressure in balloon 230, after liquid and/or gas is introduced into the balloon 230. In any event, a tube or other conduit (not shown) may connect the port 250 with the balloon 230 through body 210 along or within passageway 211.

As illustrated in FIGS. 9A-9B, the balloon 230, when expanded, may have a shape with outward sides that are linear, as viewed from the side. In other words, the balloon 230 may have a uniform, linear shape in a proximal-to-distal (or vice-versa) direction. However, in at least one embodiment (not illustrated), the shape of the outward sides of the balloon may be curved or non-linear when viewed from the side. In other words, the balloon may have a tapered, sloped, and/or partially parabolic shape in a proximal-to-distal (or vice-versa) direction. Such a curved shape may help the balloon better engage tissue at the incision 14 and/or reduce the probability of the balloon slipping or dislodging while at the same time potentially reducing the probability of rupturing or tearing the incision due to stress risers that could result from a linear shape. In any event, various configurations are possible for the balloon 230 to expand and dilate tissue at an incision or other opening into a patient's body and/or body cavity.

The surgical delivery device 200 may perform a number of functions. For example, as discussed above, the delivery device 200 may deliver an incision to an otomy site, the delivery device 200 may conceal, guide, be guided by, and/or deliver a surgical tool (e.g., an endoscope) to a body cavity, and/or the delivery device 200 may dilate an incision or other opening in the patient's body. Additionally, in various embodiments, the surgical delivery device may also serve to assist in the proper placement and/or sealing of a transorifice device 300 within a body cavity.

Figure 7:
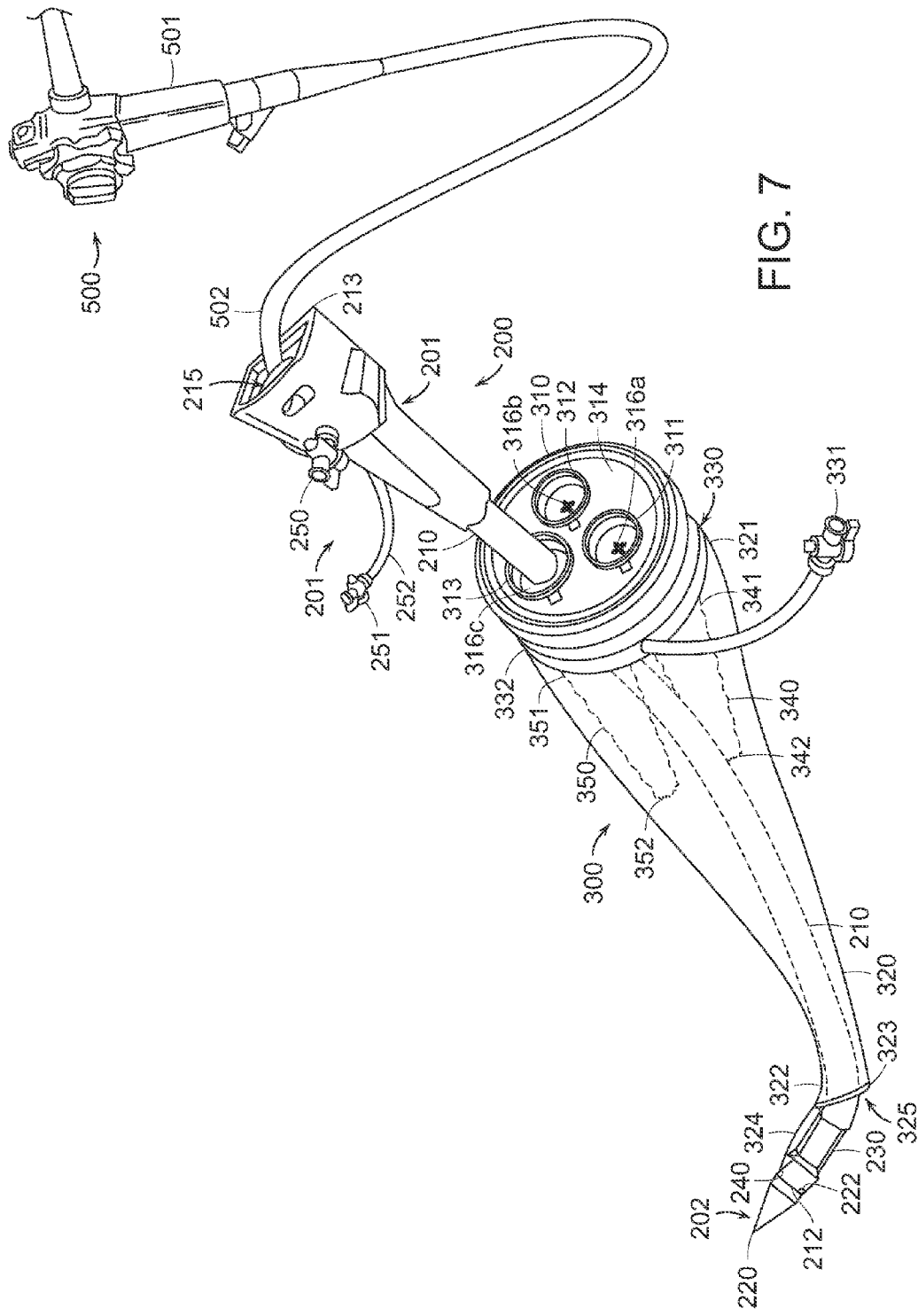
FIG. 7 illustrates the surgical delivery device of FIG. 2 inserted through a port of the transorifice device of FIG. 3; the surgical delivery device is also shown extending through the transorifice device and connected to a suture at a distal end of the transorifice device; an endoscope, according to a non-limiting embodiment, is also shown inserted partially into a tool receiving passageway of the surgical delivery device.

By way of example and referring to FIG. 7, in at least one embodiment, the surgical delivery device 200 may further comprise a suture holder 240 located near the distal end 212 of the body, wherein the suture holder 240 is configured to releasably hold a suture, such as suture 324, from the transorifice device 300 (discussed below). As shown in FIG. 7, the suture holder 240 may be positioned on or along the body 210, between the balloon 230 and the tip 220. Also, the suture holder 240 may be configured in various ways. For example, as seen in FIG. 7, the suture holder 240 may comprise a notch or a groove that is sized and configured to receive a suture 324. In other embodiments, and as discussed below, the suture holder may comprise a protrusion that is configured to releasably snag a suture. To further facilitate grasping of the suture 324 by holder 240, the suture 324 may be tied or otherwise formed into a loop. In any event, the suture holder 240 may be designed and/or oriented such that it can pull a suture 324 in a distal direction and then release suture 324 when the suture holder 240 and/or the body 210 of the surgical delivery device is moved in a proximal direction. Thus, as explained in more detail below, the suture holder 240 may allow for the surgical delivery device 200 to pull transorifice device 300 via suture 324 and then release the transorifice device 300 at a desired position and/or location within a patient's body cavity.

Moving now to the details regarding a transorifice device, such as transorifice device 300, referring to FIG. 3, in various embodiments, the transorifice device 300 may comprise a port assembly 310 and a flexible conduit 320. In at least one embodiment, the transorifice device may further comprise at least one support member 330. The port assembly 310 may define at least one port therein, such as first port 311, second port 312, and third port 313, and the port assembly 310 may also have a proximal side 314 and a distal side (not shown in FIGS. 1-11; see, however, distal side 1315 of port assembly 1310 for transorifice device 1300 seen in FIG. 24B and discussed below, for example). The flexible conduit 320 may extend from the distal side of the port assembly 310 and may also have a proximal portion 321 adjacent to the port assembly 310 and a distal portion 322. The support member 330 may be movably associated with the distal portion 322 of the flexible conduit 320 and extendable to the distal side of the port assembly 310.

Briefly, and as will be explained in more detail below, the transorifice device may be configured to span an orifice of a patient to create a conduit from outside the patient to inside the patient's body. For example, the transorifice device may be used in a vaginal NOTES procedure. Referring now to FIG. 11, the transorifice device 300 may be positioned at least partially through a speculum 100 that has been positioned and expanded within a patient's vagina. The port assembly 310 and the support member 330 may be positioned outside the patient's body and/or rest against the speculum 100. After placement of the transorifice device 300, the proximal portion 321 of the flexible conduit 320 may also pass through the speculum 100, between blades 120, 130, 140 (see FIG. 1). Also, the distal portion 322 of the flexible conduit 320 may pass through incision 14 at otomy site 13 and into the body cavity 20. Accordingly, a surgical procedure within body cavity 20, for example, may be performed by passing one or more tools through flexible conduit 320 such that the patient's tissue, e.g., the patient's vaginal walls, from the introitus to the abdominal cavity, for example, are protected from damage while passing or moving a surgical tool through the transorifice device 300.

Referring back to FIG. 3, in various embodiments, the port assembly 310 and/or ports 311, 312, 313 may be configured to provide a barrier or resistance to air or other gas, such as carbon dioxide used for insufflation, from passing from outside to inside, or inside to outside, the patient's body and thereby prevent or limit potential infection and/or desufflation. Accordingly, in at least one embodiment, one or more of the ports 311, 312, 313 may further comprise at least one seal. For example, seals 316a, 316b, 316c, associated with ports 311, 312, 313, respectively, may be employed to achieve a substantially airtight/fluidtight seal through each port 311, 312, 313, while still allowing a surgical tool or tools to pass therethrough. A variety of existing seal arrangements may be employed. For example, U.S. patent application Ser. No. 08/199,902, entitled SEAL FOR TROCAR ASSEMBLY, and U.S. patent application Ser. No. 11/014,245, entitled DUCK-BILL SEAL PROTECTOR, the disclosures of which are each herein incorporated by reference in their respective entireties, disclose seals that may be employed to establish a substantially airtight/fluidtight seal within each of ports 311, 312, 313. The seals 316a, 316b, 316c may also be configured such that when a port 311, 312, 313 is not being used, the port 311, 312, 313 is sealed off and when a surgical tool is inserted into a port 311, 312, 313, a substantially airtight/fluidtight seal is achieved between the tool and the port 311, 312, 313.

Referring still to FIG. 3, each of the ports 311, 312, 313 may be the same size. Alternatively, each port may be a different size. For example, in at least one embodiment, port 311 may accommodate a 10 mm or smaller diameter tool, port 312 may accommodate a 5 mm or smaller diameter tool, and port 313 may accommodate an 18 mm or smaller diameter tool.

Further, in at least one embodiment, each of the ports 311, 312, 313 may be independently removed from the port assembly 310. Alternatively, and as explained in more detail below, the ports 311, 312, 313 may be collectively removed from the port assembly 310. Further, the port portion or cap supporting the ports 311, 312, 313 may also be removed to additionally increase the diameter of an opening through which an item may passed. The port portion or cap may include the proximal surface 314 seen in FIG. 3, and an example of a port portion's removal is discussed below, see FIG. 24B and port portion 1310a. In any event, removing one or more of the ports 311, 312, and/or 313 and/or the port portion or cap may allow for a larger opening through the port assembly 310 such that a specimen may be removed during a surgical procedure, for example.

Focusing now on the flexible conduit 320, in various embodiments, referring to FIG. 3, the flexible conduit 320 may be made from a thin or membranous polymeric, elastomeric, and/or rubber-based material, for example. In at least one embodiment, the flexible conduit 320 is at least partially transparent. In any event, the flexible conduit 320 is configured to gently contour to a patient's tissue, such as the soft tissue of the vaginal walls 11 (see FIG. 6B, for example) and/or the tissue at incision 14 (see FIGS. 9A-9B and 11, for example). Further, the flexible conduit 320, once positioned, as shown in FIG. 11, for example, may provide a sealed conduit from outside the patient to body cavity 20. The seal, outside the patient, may be provided by port assembly 310 and/or support member 330 as either or both rest against speculum 100, discussed below. However, internally, the transorifice device may seal and/or be retained within the patient, through the patient's vagina and incision 14, for example.

Accordingly, in various embodiments, referring to FIG. 3, the flexible conduit 320 may further comprise a flexible, resilient, or pliable ring 323 located at the distal portion 322 of the conduit 320. The ring 323 may be made from a resilient material such as plastic, rubber, metal, and/or a shape memory alloy, like nitinol, for example. Also, the ring 323 may be integral and/or embedded in a membrane material of the flexible conduit 320 or may be layered between sheets of the conduit 320. Further, as noted above, the flexible conduit 320 may also comprise a suture 324 connected to the pliable ring and/or to the distal portion 322 of the conduit 320. The pliable ring 323 may be configured such that when it is not under external force, the ring 323 assumes the shape shown in FIG. 3, causing the distal portion 322 of the flexible conduit 320 to flare outward. In other words, the pliable ring 323 may be biased toward an annular or open shape. However, the pliable ring 323 may be bent into a folded shape, such as a hyperbolic paraboloid, by the application of an external force. Such external force may come from a user pulling on suture 324.

In more detail, the pliable ring 323 may be constructed as follows. The flexible membrane of the conduit 320 may include a multi-lumen channel therein that allows a nitinol wire, for example, to be wrapped multiple times around the conduit 320, thereby avoiding needing to connect one end of the wire to another, which may prevent problems due to bending of the wire at that point during use. In at least one exemplary embodiment, the pliable ring may be approximately 0.089" in cross-sectional diameter. Further, the flexible membrane of the conduit 320 may include three lumens, with each lumen being approximately 0.024" in diameter, and a nitinol wire, which may be approximately 0.019" or 0.021" in diameter. As one will appreciate, using thicker wire may provide a stiffer ring and thinner wire may provide a less stiff ring. In any event, the wire may make two complete loops around the conduit 320 which may include a wall of approximately 0.008" in thickness. Further, the lumens may be have an inner diameter of approximately 0.090" and may be approximately 5/8" to approximately 3/4" long to cover the ring once formed in the conduit 320. In a working test, ring inner diameters in the range of about 2 1/8" to about 2 3/4" were made and used in prototypes. A benchtop test showed that the 2⅛" and 2⅝" rings have relative pull through forces of 9 and 16 lbs respectively. Accordingly, as the ring should be able to completely pass through a vagotomy to be placed inside a patient's body cavity, a shorter ring may have an advantage.

In at least one embodiment, referring now to FIG. 7, and as discussed above, a suture holder, such as suture holder 240 of the surgical delivery device 200, may releasably hold suture 324. Accordingly, after attaching the suture 324 to suture holder 240, the pliable ring 323 may be pulled in a distal direction, toward tip 220 of the surgical delivery device 200, such that the pliable ring 323 collapses, buckles, or otherwise bends into a compact or folded shape. The folded shape of ring 323 may allow the ring 323, and hence, the distal portion 322 of the flexible conduit 320 to move through a smaller opening, such as incision 14 (see FIG. 10) than the ring 323 would fit through if the ring were in an unfolded, annular shape.

Notably, the port assembly 310 and the flexible conduit 320 may be configured to receive a surgical tool therethrough. Specifically, regarding positioning the transorifice device 300 at least partially within a patient, in at least one embodiment and referring to FIG. 7, the body 210 of the surgical delivery device may be placed through a port, such as third port 313, such that the tip 220 protrudes out the distal portion 322 of the flexible conduit 300. The suture 324 of the transorifice device 300 may subsequently be attached, hooked, snagged, or otherwise held by the suture holder 240 of the surgical delivery device 200.

Figure 10:
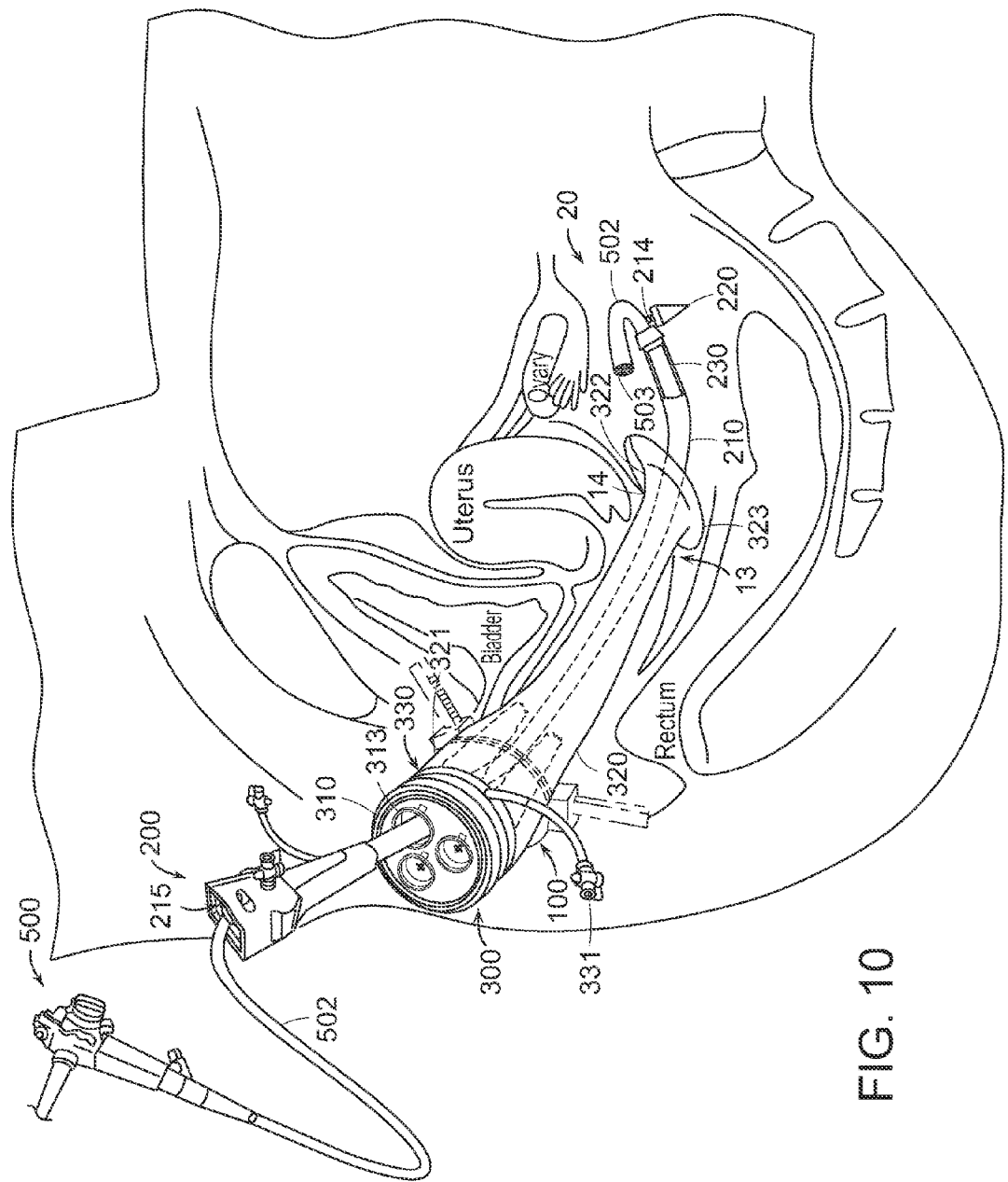
FIG. 10 illustrates the speculum, the surgical delivery device, the transorifice device, and the endoscope of FIG. 8 after advancing the surgical delivery device to position a pliable retention ring of the surgical delivery device within the patient's body cavity; further, the suture of the transorifice device has been released from the distal portion of the surgical delivery device to enable the pliable retention ring to also expand or unfold within the body cavity, adjacent to the otomy site in the vagina.

Thus, in at least one embodiment, and as noted above, referring to FIGS. 7 and 11, the suture holder 240 may allow for the surgical delivery device 200 to pull transorifice device 300 via suture 324 and then release the transorifice device 300 at a desired position and/or location within a patient's body cavity 20. For example, the suture holder 240 may pull the suture 324 and, thus the pliable ring 324 and distal portion 322 of the flexible conduit 320, through the incision 14 at otomy site 14. Then, the suture holder 240 may release the suture 324, as described above, such that the pliable ring expands to an annular-like shape as shown in FIG. 10, thereby sealing and retaining the distal portion 322 of the flexible conduit 320 within the patient's body cavity 20 at incision 14. Accordingly, the transorifice device 300 may provide a sealed passageway, through flexible conduit 320, from outside a patient's body to body cavity 20. The pliable ring 323 may also prevent inadvertent removal or dislodgment of the distal portion 322 from a patient's body, thereby retaining the transorifice device 300 within the patient during a surgical procedure.

After a surgical procedure is completed, the transorifice device may be removed by pulling the port assembly 310 away from the patient, thereby forcing the pliable ring 323 to bend and fit through incision 14. Alternatively, the suture 324 may continue in a proximal direction at least to the port assembly such that a user may pull on the suture to collapse or buckle the pliable ring 323 to fit it through the incision prior to pulling on the port assembly 310. Further, a tie off structure such as a protrusion may be part of the port assembly 310 to hold the suture 324 at that position until needed.

Focusing now on the support member 330, in various embodiments, the support member 330 may be configured to provide support for the port assembly 310 and/or the flexible conduit 320 after the transorifice device 300 is positioned at least partially within a speculum, such as speculum 100, see FIGS. 1 and 8. In various embodiments, the support member 330 may comprise an expandable bladder 332 that is expandable or inflatable between an unexpanded and an expanded configuration. For example, FIG. 10 shows the expandable bladder 332 in an unexpanded configuration and FIG. 11 shows the expandable bladder 332 in an expanded configuration. The bladder 332 may be expanded via port 331. Port 331 may comprise a stopcock valve and may allow gas and/or liquid to be passed through port 331 into bladder 332 to inflate and/or expand the same. The port 331 may then be closed to maintain gas and/or liquid pressure within the expanded bladder 332, see FIG. 11. Then, after a surgical procedure is completed, the bladder 332 may be deflated or compressed to an unexpanded configuration by opening port 331 to release gas and/or liquid pressure.

Figure 11:
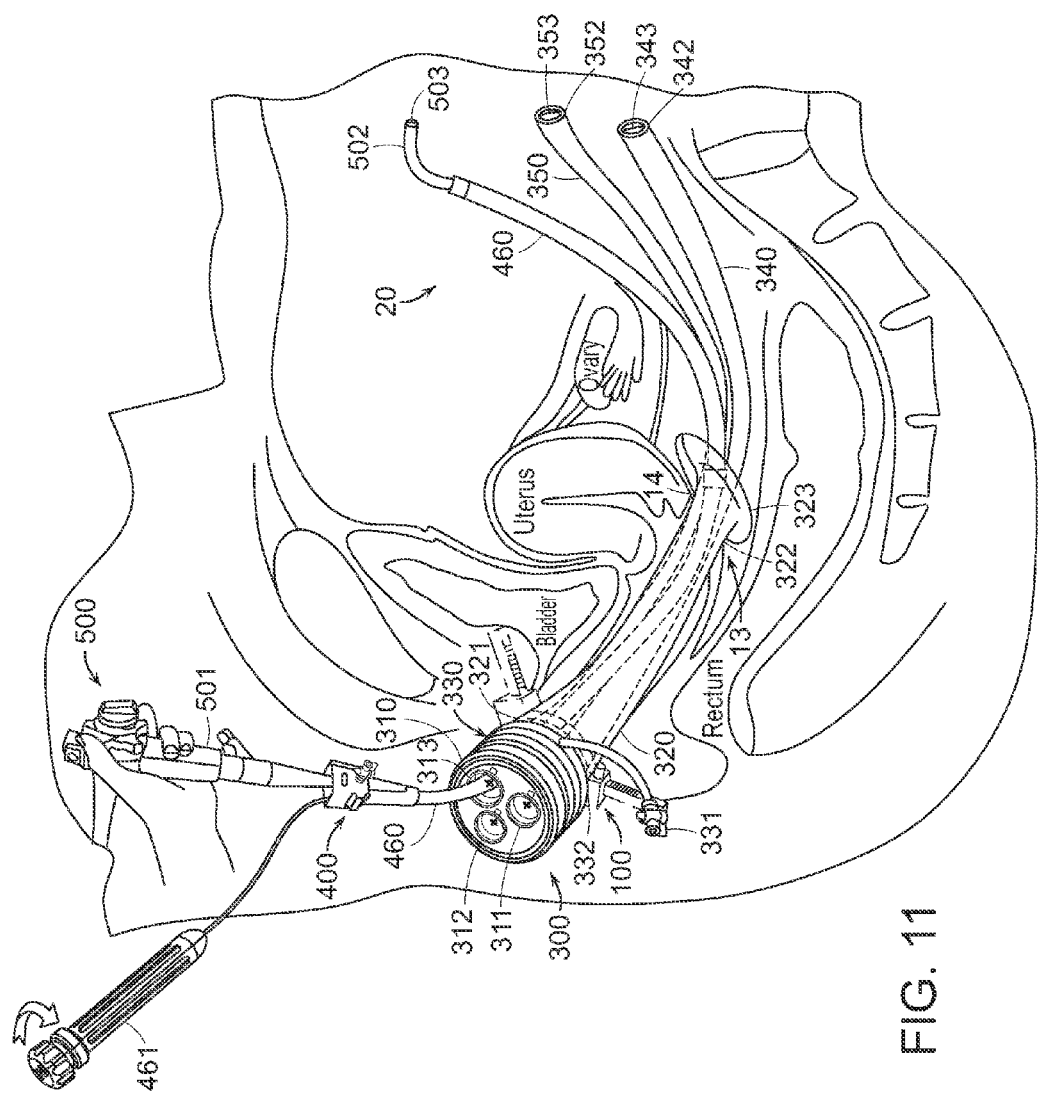
FIG. 11 illustrates the speculum, the surgical delivery device, the transorifice device, and the endoscope of FIG. 10 after expanding a bladder of the transorifice device into contact with the speculum, inserting the steerable flexible trocar of FIG. 4 through a port of the transorifice device, passing an endoscope through the steerable flexible trocar and into the body cavity, and extending two sleeves associated with two additional ports of the transorifice device into the body cavity to perform a surgical procedure therein.

Still referring to FIG. 11, as noted above, while the transorifice device 300 is positioned at least partially through speculum 100, the bladder 332 may provide support to the port assembly 310 and/or to the flexible conduit 320 during a surgical procedure. Accordingly, the expandable bladder 332 may be configured such that at least a portion, e.g., a proximal portion, of the bladder 330 contacts the port assembly 310 when the bladder 332 is expanded.

Further, in at least one embodiment and as seen in FIG. 11, the bladder 332 may also contact at least a portion of the speculum 100 when the bladder 332 is expanded. In such embodiments, the bladder 332 may serve as a flexible shock absorber and/or resilient mount between the transorifice device 300 and the speculum. The expanded bladder 332 thus may provide support to the port assembly 310 and/or the flexible conduit 320 while permitting flexible maneuverability to a surgical tool inserted through the transorifice device 300. Additionally, referring still to FIG. 11, when expanded, the bladder 332 may take up obstructive slack in the flexible conduit, between the distal portion 322 and the proximal portion 321. In other words, a portion of the bladder 332 may move with respect to the distal portion 322 of the flexible conduit 320 such that the port assembly 310 and/or the proximal portion 321 of the conduit 320 move away from the distal portion 322 and/or pliable ring 323, secured through incision 14. Accordingly, the flexible conduit 320 may be made taught by way of expanding bladder 332 and anatomical variation between patients' vaginal lengths may be further removed as a significant surgical factor. In at least one such embodiment, the flexible conduit may be approximately five inches in length and/or the bladder may expand to approximately three inches in height to thereby accommodate a majority of the patient population.

In at least one embodiment, the expandable bladder 332 may be connected to the port assembly 310 and the flexible conduit may pass through the expandable bladder 332. Alternatively, the bladder 332 may be discontinuous with the port assembly 310; however, the flexible conduit 320 may still pass through the expandable bladder. In such embodiments, the bladder 332 may also be movable with respect to the flexible conduit 320. Further, in at least one embodiment, the flexible conduit may be integrally formed with the bladder 332.

Further, referring to FIGS. 6B and 11, in at least one embodiment, the bladder 332 may have an outer diameter that is larger than the flexible conduit 320 and/or the speculum base 110, such that the conduit 320 may pass through the base 110 while the bladder 332 may contact and be supported by the proximal surface 112 of the base 110, as noted above.

The transorifice device 300 may be further configured to provide additional protection to tissue and/or organs within a patient's body during a surgical procedure. For example, in at least one embodiment, the transorifice device 300 may further comprise a first extendable sleeve 340 extending from at least one port, such as first port 311. The extendable sleeve 340 may be further located at least partially within the flexible conduit 320. Further, in another embodiment, the transorifice device 300 may further comprise a second extendable sleeve 350 extending from the second port 312. The second extendable sleeve 350 may further be located at least partially within the flexible conduit 320. As shown in FIG. 3, the first extendable sleeve 340 and the second extendable sleeve 350 may be seen through and residing within flexible conduit 320, each in a retracted configuration. In at least one embodiment, one or both of sleeves 340, 350 may be pleated or crinkled such that each sleeve 340, 350 may rest, accordion-style, in the retracted configuration seen in FIG. 3, for instance.

In at least one embodiment, referring to FIG. 11, one or both of extendable sleeves 340, 350 may be extended into an extended configuration such that first extendable sleeve 340 and/or second extendable sleeve 350 extends beyond the distal portion 322 of the flexible conduit and into a body cavity, such as abdominal cavity 20. In such embodiments, the extendable sleeves 340, 350 may help provide further protection to internal organs and/or tissue during surgical instrument exchanges through first port 311 and/or second port 312. For example, as seen in FIG. 11, after placement of the transorifice device 300 at least partially within the patient, the extendable sleeves 340, 350 have both been extended into an extended configuration within abdominal cavity 20, thereby providing individual and separably positionable conduits through which tools may pass farther into a patient than flexible conduit 320 may provide by itself. In other words, first sleeve 340 may be extended and positioned apart from second sleeve 350 and vice versa. The extendable sleeves 340, 350 allow the surgeon to pass instruments without having the need to distract the surgeon from the procedure and to ensure safe instrument passage.

In various embodiments, one or more of the extendable sleeves 340, 350 may include features to facilitate their extension. For example, referring to FIG. 3, in one embodiment, the first extendable sleeve 340 may comprise a proximal end 341 abutting the first port 311 and a distal end 342, and the second extendable sleeve 350 may likewise comprise a proximal end 351 abutting the second port 312 and a distal end 352. The extendable sleeves 340, 350 may be made of a flexible material such as a plastic or rubber-based material such that they can be easily manipulated and positioned, yet not easily tear or rupture. Further, referring to FIG. 11, first extendable sleeve 340 may also include a first suture 343 located at the distal end 342 of sleeve 340 and/or the second extendable sleeve may include a second suture 353 located at the distal end 352 of sleeve 350.

In at least one embodiment, the extendable sleeves 340, 350, may be extended as follows. Initially, the extendable sleeves 340, 350 may be received by a user in a retracted configuration, see FIG. 3. Then, after placement of the transorifice device 300 within the patient, referring to FIG. 11, an endoscopic or laparoscopic tool, such as a grasper known in the field, may be inserted through first port 311. The grasper may be used to grab the first suture 343 and/or the distal end 342 of the first extendable sleeve 340. Next, the grasper may be moved distally, thereby pulling the distal end 342 through the distal portion 322 of the flexible conduit 320 and into the patient's body cavity 20. Similar such steps may be performed to extend second flexible sleeve 350; e.g., inserting a grasper through second port 312 and grabbing the distal end 352 and/or second suture 353 to pull the second extendable sleeve 350 into an extended configuration, as seen in FIG. 11.

In at least one embodiment, an extendable sleeve may extend from each of the ports 311, 312, 313. Alternatively, and as illustrated in FIGS. 3 and 11, in at least one other embodiment, no extendable sleeve may extend from the third port 313. Accordingly, as shown, two of the ports, e.g., ports 311 and 312, have extendable sleeves 340, 350, respectively associated with them, and port 313 does not have an extendable sleeve associated with it. In such embodiments, port 313 may therefore accommodate relatively larger instruments therethrough, such as a steerable flexible trocar 400 and/or an endoscope 500, owing to port 313's size and/or lack of a protective, extendable sleeve. This may also be desirable, where, as illustrated, a surgical device, such as the steerable flexible trocar 400 and/or endoscope 500 are positioned and left as such during the majority of the surgical procedure (e.g., for viewing purposes through endoscope 500). Therefore, because instrument exchanges through the third port 313 may be kept to a minimum, inclusion of a third extendable sleeve associated with port 313 may be unnecessary and/or undesirable.

By way of overview and with reference above as needed, and/or helpful, in various embodiments, referring to FIGS. 1-3, a surgical system or kit comprising speculum 100, surgical delivery device 200, and transorifice device 300 may be used in a surgical procedure as follows. Referring to FIG. 6A, the speculum 100, in a closed configuration, may first be inserted into a patient's vagina 10. Then, referring to FIG. 6B the speculum 100 may be expanded into an opened configuration such that the speculum blades 120, 130, 140 dilate or otherwise stretch apart vaginal walls 11. Also, sutures 12a, 12b, 12c may be added to the vaginal walls 11 between the blades 120, 130, 140 of the speculum 100 to identify an otomy site 13. Such an otomy site 13 may correspond with the fornix of the vagina, and/or with the rectouterine pouch of the peritoneal cavity, between the uterus and the rectum. Further, the sutures 12a, 12b, 12c, for example, may enhance access to the rectouterine pouch.

Referring to FIG. 7, the surgical deliver device 200 and the transorifice device 300 may now be coupled outside the patient's body. Alternatively, a user may receive or obtain a surgical delivery device 200 pre-coupled to the transorifice device 300. In any event, the surgical delivery device's body 210 may be inserted through port 313 of the transorifice device 300. The surgical delivery device 200 may also thereafter be positioned such that the delivery device's body 210 extends through the transorifice device's flexible conduit 320 and the delivery device's tip 220 extends beyond the distal portion 322 of the flexible conduit 320. The delivery device's suture holder 240 may then be connected to the flexible conduit's suture 324. Further, the tube-like portion 502 of endoscope 500 may also be at least partially inserted into the tool receiving passageway 211 (see FIG. 2) via proximal opening 215 of the surgical delivery device 200.

Next, referring to FIG. 8, the coupled surgical delivery device 200 and transorifice device 300 may be at least partially inserted through the opened speculum 100, and into the patient's vagina 10 (see FIG. 6B). In at least one embodiment, the endoscope's distal end 503 (see FIG. 9B) may be near the transparent tip 220 such that a user can visualize tissue near the tip 220 through the endoscope located at least partially within passageway 211 (see FIG. 2). Thus, the endoscope may help guide the devices into the patient's body to otomy site 13. Then, the tip 220 may be advanced against the vaginal walls at otomy site 13 until an incision 14 (see FIG. 9B) is created. As illustrated, the tip may then protrude into a body cavity 20, which may include the peritoneal cavity. In at least one embodiment, the tip 220 may protrude into the rectouterine pouch of the peritoneal cavity.

Referring to FIG. 9A, which shows an enlarged view of the distal portions of the components of the surgical system near the otomy site 13, after the surgical delivery device's tip 220 has created an incision 14 under vision through the vaginal wall 11 at an otomy site 13, the balloon 230 of the surgical delivery device 200 may be positioned within the incision 14 and expanded to dilate the incision 14. Then, as shown in FIG. 9B, the endoscope's tube-like portion 502 may be advanced to push open the delivery devices' tip 220. Thereafter, the distal tip 503 of the endoscope may be articulated using the endoscope's control handle 501 (see FIG. 8) to inspect the body cavity 20, otomy site 13, and/or incision 14.

Further, in various embodiments, the body cavity 20 may be insufflated prior to, during, and/or after the insertion of surgical delivery device 200 into cavity 20. For example, referring to FIG. 7, the surgical delivery device 200 may further include an insufflation port 251. Port 251 may be configured to deliver a gas, such as carbon dioxide or nitrogen, for example, to the passageway 211 (see FIG. 2) such that when the tip 220 is opened (see FIG. 9B), gas may pass therethrough to insufflate the body cavity. Alternatively, referring still to FIG. 9B, after the tip 220 is opened, insufflation may also occur through the endoscope 500. In other words, gas may be passed through a working channel or other conduit of endoscope 500 to insufflate the body cavity 20. Alternatively, as is know in the field, a veress needle or other laparoscopic tool may be inserted through the patient's body wall, such as their abdominal wall, to provide a gas therethrough and thereby insufflate the body cavity 20. Alternatively, referring to FIG. 10, the port assembly 310 of the transorifice device 300 may include an insufflation port (not shown) to provide gas therethrough and into body cavity 20.

Next, referring to FIG. 10, once the incision 14 has been sufficiently dilated, the surgical delivery device 200 may be advanced distally such that the transorifice device's pliable ring 323 is pulled through the incision 14. In at least one embodiment, the transorifice device's port assembly 310 may contact the speculum 100 prior to the ring 323 passing through the incision 14 such that pulling the ring 323 through the incision results in the flexible conduit 320 elongating along the length of the patient's vagina. In any event, after the pliable ring 323 is pulled through the incision 14, the transorifice device's suture 324 (see FIG. 9A) may then be released from the surgical delivery device 200 by moving the delivery device 200 in a proximal direction, for example. Then, the transorifice device's pliable ring 323 may expand and/or unfold into a retaining position as shown, distal to incision 14. The delivery device's balloon 230 may also be deflated and/or unexpanded and then the surgical delivery device may be removed from the body cavity by pulling it proximally, through the transorifice device's flexible conduit 320, and out port 313.

Referring to FIG. 11, the transorifice device's support member 330 may also be brought into contact with the speculum 100. In at least one embodiment, the support member 330 may include an expandable bladder 332 that may be inflated and/or expanded to bring the bladder 332 into contact with the speculum 100 and/or to raise the port assembly 310 with respect to the speculum and/or to remove slack from the flexible conduit 320. As discussed previously, this may provide additional support for the port assembly 310 and/or enable flexible maneuverability of the transorifice device 300 when surgical tools are passed therethrough.

Ultimately, a surgical procedure, such as an oophorectomy, cholecystectomy, and/or hepatectomy, for example, may be performed through the transorifice device 300. For example, an endoscope 500 may be inserted into a steerable flexible trocar 400 to provide additional control and stability to the endoscope 500. The endoscope 500 and steerable flexible trocar 400 may then be inserted into a port, port 313 for example, which may not have an extendable sleeve associated therewith. A sheath 460 of the flexible trocar 400, the endoscope's tube-like portion 502, and/or the endoscope's distal end 503 may then be at least partially advanced distally, through the flexible conduit 320 and into the body cavity 20. The flexible trocar's sheath 460 may be steered or otherwise articulated via a control handle 461 coupled to the sheath 460 by at least one control wire contained within control cable 463. Adjusting the handle 461 may move the control wires to articulate the sheath 460 and thereby position the endoscope's distal end 503 within the cavity 20. The surgical procedure may thus be visualized through the endoscope 500. Further, in at least one embodiment, the endoscope 500 may have working channels (not shown) for passing endoscopic tools therethrough.

Still referring to FIG. 11, the transorifice device's extendable sleeves 340, 350 may also be extended such that the distal ends 342, 352, respectively, are located past the distal portion 322 of the flexible conduit, within the body cavity 20. Each sleeve 340, 350 may be positioned independently of the other to provide conduits through which surgical tools, such as endoscopic tools, may be passed. Accordingly, an entire surgical procedure may be performed through the transorifice device 300 and, thus, through the patient's natural orifice, e.g., through the patient's vagina.

After completing the surgical procedure, various components of the system may be removed from the patient as described above. Then, the incision 14 may be closed using one or more sutures and/or biocompatible adhesives or sealants as is known in the field.

Figure 12A:
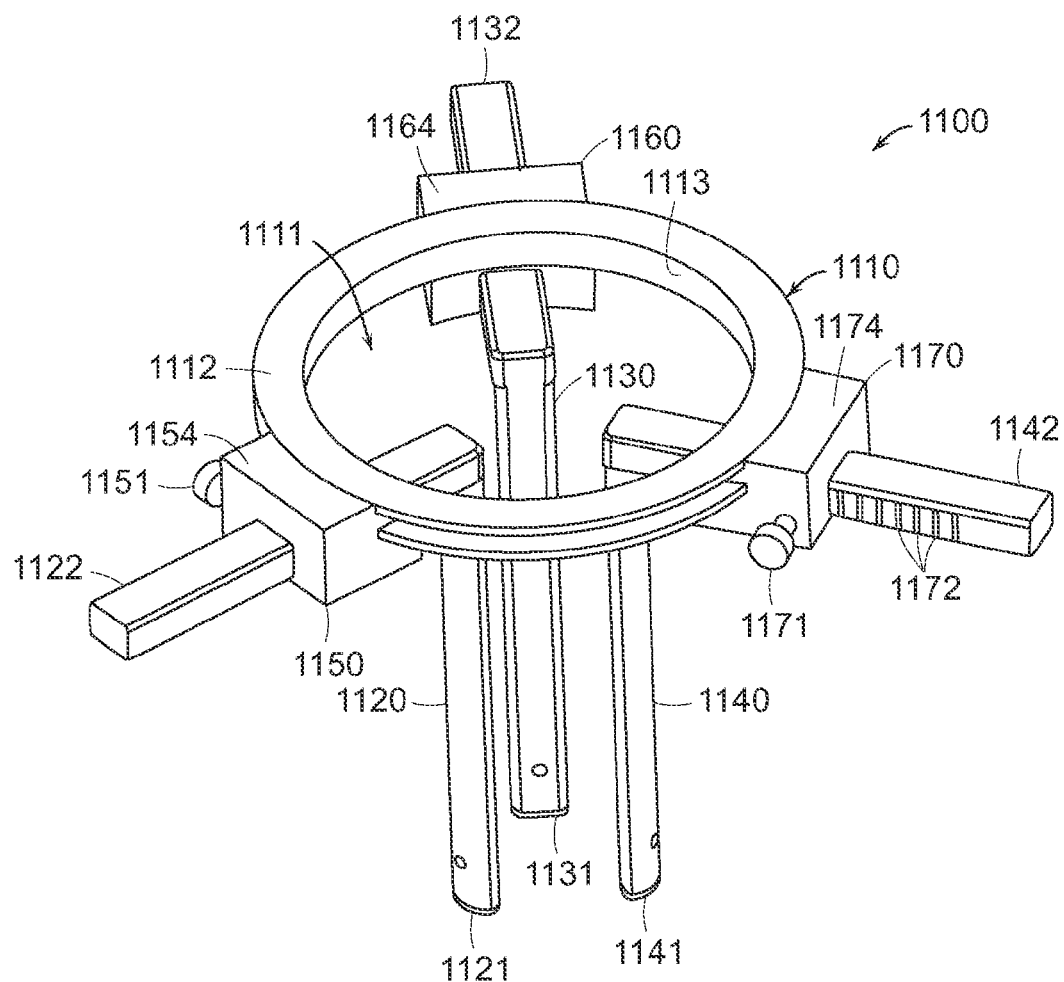
FIG. 12A is a perspective view of a speculum according to a non-limiting embodiment.
Figure 12B:
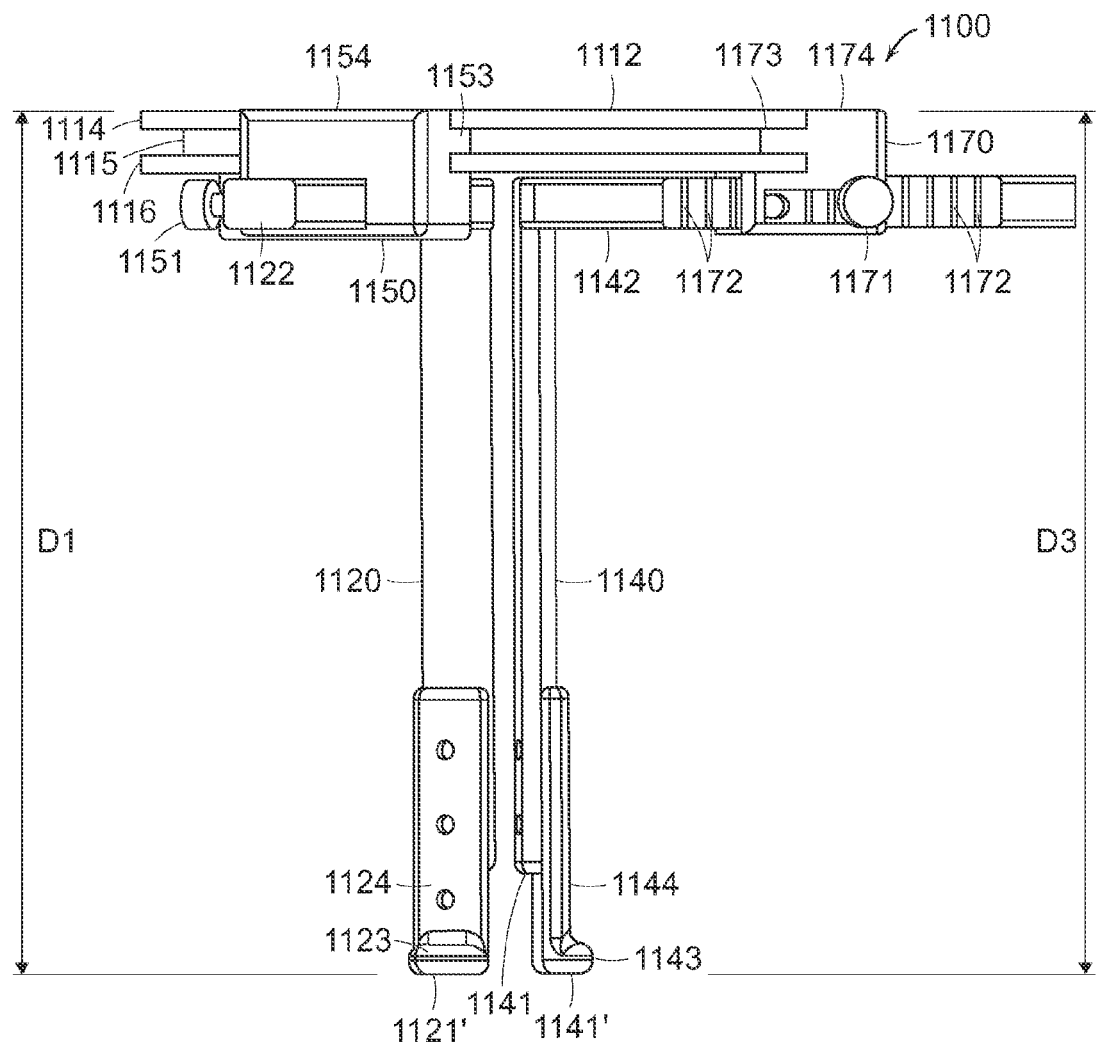
FIG. 12B is a side view of the speculum of FIG. 12A with blade tip attachments connected to blades of the speculum.

In various embodiments, additional speculums and speculum features are envisioned which may, among other things, provide similar advantages to that described above with respect to speculum 100 and may also be substituted for speculum 100 in a surgical system, kit, and/or method such as that shown and portrayed in one or more of FIGS. 1-11. Referring now to FIGS. 12A-12B, in at least one embodiment, an exemplary speculum 1100 is provided. Speculum 1100 is similar to speculum 100 described above in that speculum 1100 may include a base 1110 comprising a proximal surface 1112 and an inner wall 1113 defining an opening 1111. Further, the speculum 1100 may comprise a first blade 1120, a second blade 1130, and a third blade 1140, each attached to the base and movable with respect to each other. As with speculum 100, speculum 1100 may include at least one locking assembly in the form of first ratchet assembly 1150, second ratchet assembly 1160, and third ratchet assembly 1170. These ratchet assemblies function similarly to the ratchet assemblies 150, 160, 170 described above in that each may include a pawl (not shown) that operably engages teeth formed in or attached to support bars 1122, 1132, 1142 which are subsequently connected to blades 1120, 1130, 1140, respectively. For example, as shown in FIGS. 12A-12B, third ratchet assembly 1170 operably receives teeth 1172 formed in support bar 1142. In any event, the ratchet assemblies 1150, 1160, and 1170 allow the bars 1122, 1132, 1142, and thus blades 1120, 1130, 1140 to be independently moved apart and locked or held at a desired distance from one another. Further, the ratchet assemblies 1150, 1160, 1170 may, as described above with respect to ratchet assemblies 150, 160, 170, allow blades 1120, 1130, 1140 to move towards each other when buttons 1151, 1161, 1171 are operated thereby unlocking the ratchet assemblies 1150, 1160, 1170.

Additionally, referring to FIG. 12A, each blade 1120, 1130, 1140, may include a distal end 1121, 1131, 1141, respectively, that are each at approximately the same distance from the proximal surface 1112 of base 1110, such that, when inserted into a patient, the proximal surface 1112 may serve as a support surface for another surgical device, where the entrance to the body, through an otomy site found between blades 1121, 1131, 1141, may be at a known distance past the proximal surface 1112, thereby alleviating at least one potentially unknown variable from the surgical procedure. In at least one embodiment, referring to FIG. 12B, attachments, such as blade tip attachments 1124, 1144, for example, may be added to each of the blades 1120, 1140, respectively, to extend their length and/or alter the shape of the blades. In such embodiments, the blades 1120, 1140 may have extended tip ends 1121', 1141', respectively. Further, although not shown in FIG. 12B, blade 1130 may likewise have a similar attachment coupled thereto. Referring still to FIG. 12B, each blade tip attachment 1124, 1144 may include a distal portion 1123, 1143 that has a shape which at least partially projects or protrudes outward, away from the other blades to which each attachment 1124, 1144 is attached. For example, in the illustrated embodiment of FIG. 12B, the distal portion 1123 of attachment 1124 attached to first blade 1120 protrudes away from the third blade 1140 (and, although not seen in FIG. 12B, from the second blade as well). Such a shape may facilitate gripping or retention of the speculum in the vaginal walls 11 (see FIG. 6B, for example); for instance, the shape may be configured to press against the pubis bone and/or other tissues through the vaginal walls, thereby securing the speculum 1100 within the vagina. Further, the attachments 1124, 1144 may similarly be detached and replaced with a different attachment if desired. For example, attachments such as blade tip attachments 1124, 1144 may be replaced with an attachment having a different shape such as that of blade tip attachments 2124, 2134, and/or 2144 (see FIG. 13A) described in more detail below. Also, each blade tip attachment may have a shape that contacts or meets another blade tip attachment when the blades are in a fully closed position, thereby providing a closed insertion tip to ease insertion into a patient's vagina, for example. Referring back to FIG. 12A, each blade tip attachment may be releasably secured to one of blades 1120, 1130, and/or 1140 using adhesives, fasteners, and/or snap-fit features, for example. Additionally, each blade tip attachment may be attached to one of the blades 1120, 1130, 1140 at different points than that illustrated in FIG. 12B. In such embodiments, the overall length of each blade may be independently adjusted.

Additionally, while it may be desirable to attach different blade tip attachments to a speculum, it is also possible for each blade to have an integral blade tip portion that includes a shape which protrudes away from the other blade(s) without requiring a separate attachment as shown in FIG. 12B. For example, referring briefly back to FIGS. 1 and 5B, speculum 100 may include, according to at least one embodiment, blades 120, 130, and 140 which respectively include distal portions 123, 133, 143 having shapes which protrude outwardly, away from the other blades of speculum 100.

Figure 20A:
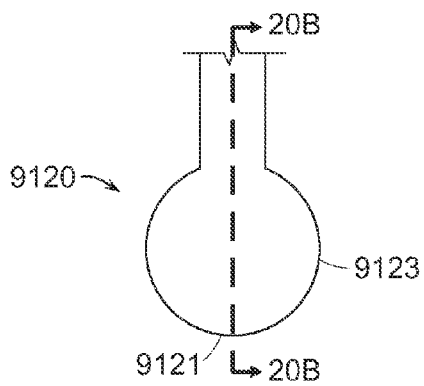
FIG. 20A is a front view of a speculum blade according to a non-limiting embodiment.
Figure 20B:
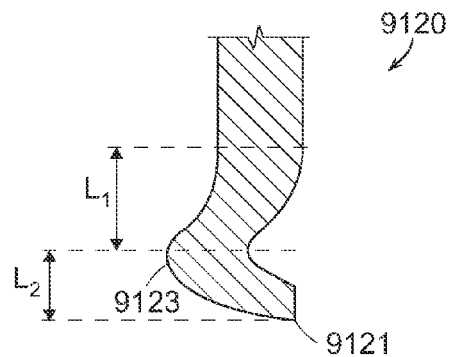
FIG. 20B is a cross-sectional view of the speculum blade of FIG. 20A, taken along line 20B-20B.

In any event, regardless of whether one or more blades have an integral blade tip portion or a blade tip attachment, each blade may vary in width length, thickness, contour, and distal shape to address anatomical variation between patients, to provide enhanced position holding or retention of the speculum at a desired location in the vagina, or to address exposure preferences when opening the speculum. By way of example and in at least one embodiment, referring to FIG. 20A, a speculum blade, such as speculum blade 9120, for example, may include a distal portion 9123 that includes an enlarged and/or semi-circular tip at or near a distal end 9121 of the blade 9120. FIG. 20A shows a front view of the blade, which may engage tissue in the direction of a viewer of the figure. Further, FIG. 20B is a cross-sectional view of the speculum blade 9120, taken along line 20B-20B. In at least one embodiment, referring to FIG. 20B, the distal portion 9123 may have a configuration which, moving from a proximal portion to distal end 9121, curves outward, to the left of FIG. 20B over a first length L1, and then inward, to the right of FIG. 20B, over a second length L2. In such embodiments, tissue, e.g., a vaginal wall, may be engaged to the left of FIG. 20B. Accordingly, the shape of distal portion 9123 shown in FIGS. 20A-20B may help retain an opened speculum in a patient by providing a gripping force against tissue provided, in part, by the outward curve of portion 9123 shown in FIG. 20B. However, owing at least partially to the semi-circular shape of distal portion 9123 shown in FIG. 20A and/or the inward curve shown in FIG. 20B, the blade 9120 may be easily inserted into a patient when a speculum is in a closed position. The first and second lengths L1, L2, and the associated curves' radii may be adjusted to maximize gripping and/or insertion capability. Thus, a variety of shapes may be utilized to provide, among other things, the above benefits.

Referring back to FIGS. 12A and 12B, in at least one embodiment, the blades 1120, 1130, 1140 may be substantially parallel with each other (straight with respect to each other from the top to the bottom of the page of FIG. 12B) when the first blade and the second blade are in a locked position, such as the positions shown in FIGS. 12A and 12B, for example. Such parallel uniformity between the blades allow each to more uniformly engage the vaginal walls 11 (see FIGS. 6A-6B) along the length of each of the arms 1120, 1130, 1140 when the arms are moved apart. Uniform engagement of the vaginal walls may help reduce localized stress around and between the arms such that tissue tearing may be avoided and the relative position of the speculum 1100 in the vagina 10 (FIG. 6B) may be maintained. Alternatively, in at least one embodiment, the blades may be at an angle other than 90 degrees with the proximal surface of the base. In such embodiments, the blades may be angled outward, away from each other, such that the blades do not angle inward when expanded or moved apart from each other. Such an outward angling of the speculum blades may help hold the speculum in place during an operation.

Additionally, referring to FIG. 12B, as noted above with respect to speculum 100, the shortest distances between a plane defined by the proximal surface 1112 of base 1110 and each of the blades' distal ends (e.g., first distal end 1121', second distal end (not shown), and third distal end 1141') may be substantially equal therebetween. As seen in FIG. 12B, the plane defined by proximal surface 1112 may be defined as a plane which is transverse to the page of FIG. 12B and which passes through the surface 1112. Further, for example, the distance D1 from end 1121' to the plane of the proximal surface 1112 may be approximately equal to the distance D2 from end 1141' to the plane of the proximal surface 1112. Accordingly, the proximal surface 1112 of base 1110 may serve as a support or contact surface for another surgical device, where the entrance to the body, through an otomy site 13 (see FIG. 6B) between blades 1120, 1130, 1140, is at a known distance past the proximal surface 1112, thereby alleviating at least one potentially unknown variable from the surgical procedure. Further, referring still to FIG. 12B, in such embodiments, the first blade 1120, the second blade 1130 (see FIG. 12A), and the third blade 1140 may be movable with respect to each other such that the first distal end 1121', the second distal end (not shown), and the third distal end 1141' may substantially move in the same plane, e.g., a plane perpendicular to the page of FIG. 12B and passing through the distal ends 1121', 1141'. Thus, because a user knows the distance that each blade 1120, 1130, 1140 extends into a patient, the user may be confident that each distal end of the blades will move in a known plane and thereby, once otomy site 13 (see FIG. 6B) is drawn taught between the blades 1120, 1130, 1140, as described above, the user will know not only the depth from the proximal surface 1112 of the speculum base 1110 to the otomy site, but he or she will also know the orientation of the tissue at the site.

Continuing, referring to both FIGS. 12A and 12B, in at least one embodiment, proximal surface 1112 may be enhanced as a support surface by limiting other components of speculum 1100 from protruding in a proximal direction (toward the top of the page of FIG. 12B) beyond the proximal surface 1112. In other words, the speculum 1100 may be low in profile. For example, the first blade 1120, second blade 1130, and third blade 1140 and/or the locking assemblies, e.g., ratchets 1150, 1160, 1170, may be configured not to protrude proximally beyond the proximal surface 1112. In other words, if proximal surface 1112 defines a plane, then none of the other various components of speculum 1100 may extend proximally beyond that plane. However, other components may serve to increase the contact area available to another surgical device over that provided by the proximal surface 1112 of the base 1110 alone. For example, in at least one embodiment, and still referring to FIGS. 12A-12B, ratchet assemblies 1150, 1160, 1170 may be configured to be flush with proximal surface 1112 of the base 1110. In other words, ratchet assemblies 1150, 1160, 1170 may include ratchet housing surfaces 1154, 1164, 1174, respectively, that are in the same plane as that of the base's proximal surface 1112.

Referring to FIG. 12B, to facilitate speculum 1100 including such a low profile, speculum base 1110 may include an annular groove 1115 defined in between a proximal lip 1114 and a distal lip 1116 of an outer side of the base 1110. Further, each ratchet assembly 1150, 1160, 1170 may include a protrusion that is received in the groove 1115, such as protrusions 1153, 1173 seen in FIG. 12B as part of ratchet assemblies 1150, 1170, respectively (the protrusion for ratchet assembly 1130 cannot be seen in FIGS. 12A-12B, but it may be similar to the illustrated protrusions 1153, 1173). Accordingly, ratchet assemblies 1150, 1160, 1170 may be attached to the base 1110 in a low-profile fashion.

Figure 13A:
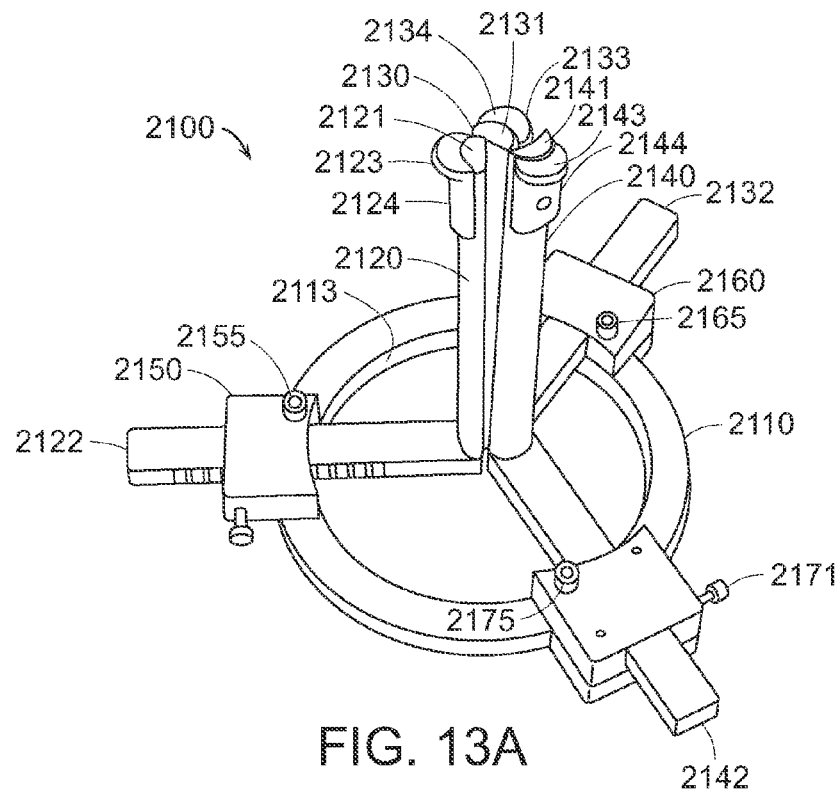
FIG. 13A is a perspective view of a speculum in a closed configuration according to a non-limiting embodiment.
Figure 13B:
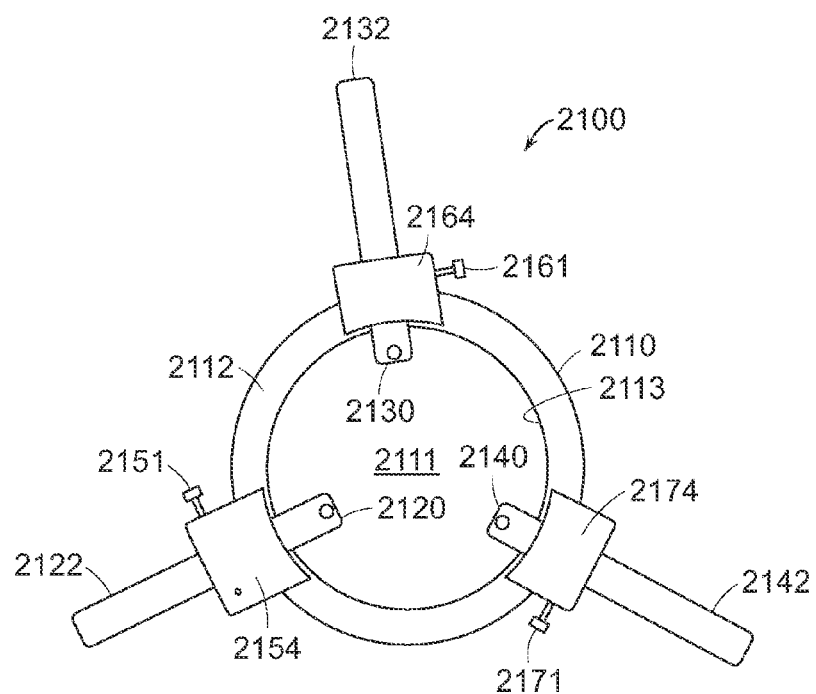
FIG. 13B is a top view of the speculum of FIG. 13A in an opened configuration.

Moving now to FIGS. 13A-13B, another embodiment of an exemplary speculum, speculum 2100 is shown. Speculum 2100 is similar to speculum 100 described above in that speculum 2100 may include a base 2110 comprising a proximal surface and an inner wall 2113 defining an opening 2111. Further, the speculum 2100 may comprise a first blade 2120, a second blade 2130, and a third blade 2140, each attached to the base via ratchet assemblies 2150, 2160, 2170 and support bars 2122, 2132, 2142, respectively. Also, as discussed previously, the blades 2120, 2130, 2140 may be movable with respect to each other. As with speculum 100, speculum 2100 may include at least one locking assembly in the form of first ratchet assembly 2150, second ratchet assembly 2160, and third ratchet assembly 2170. These ratchet assemblies function similarly to the ratchet assemblies 150, 160, 170 described above in that each may include a pawl (not shown) that operably engages teeth or detents formed in or attached to support bars 2122, 2132, 2142 which are subsequently connected to blades 2120, 2130, 2140, respectively. For example, as shown in FIG. 13A, first ratchet assembly 2150 may operably engage teeth 2152 formed in support bar 2122. In any event, the ratchet assemblies 2150, 2160, and 2170 allow the bars 2122, 2132, 2142, and thus blades 2120, 2130, 2140 to be independently moved apart and locked or held at a desired distance from one another. Further, the ratchet assemblies 2150, 2160, 2170 may, as described above with respect to ratchet assemblies 150, 160, 170, allow blades 2120, 2130, 2140 to move towards each other when buttons 2151, 2161, 2171 are operated thereby unlocking the ratchet assemblies 2150, 2160, 2170. In the embodiment illustrated in FIG. 13A, the ratchet assemblies 2150, 2160, 2170 are each clamped to annular base 2110 via screws 2155, 2165, 2175, respectively. While screws 2155, 2165, 2175 are shown as protruding out from the ratchet assemblies 2150, 2160, 2170, the screws may be set therein such that no part of the screws 2155, 2165, 2175 extends out of the respective ratchet assembly 2150, 2160, 2170 to provide a smooth surface against which the ratchet assemblies 2150, 2160, 2170 may contact a patient's exterior, e.g., a patient's skin.

In at least one embodiment, referring to FIG. 13A, an attachment, such as blade tip attachments 2124, 2134, 2144, for example, may be added to each of the blades 2120, 2130, 2140, respectively, to alter the shape of the blades 2120, 2130, 2140, similar to that described with respect to speculum 1100, above. However, in the embodiment of FIG. 13A, the blades 2120, 2130, 2140 may have tip ends 2121, 2131, 2141, respectively, where the blade attachments 2124, 2134, 2144, do not extend from the blades 2120, 2130, 2140 distally. Referring still to FIG. 13A, as with speculum 1100 discussed above, each blade tip attachment 2124, 2134, 2144 may include a distal portion 2123, 2133, 2143 that has a shape which at least partially projects or protrudes outward, away from the other blades 2120, 2130, 2140 to which each attachment 2124, 2134, 2144 is attached. However, the blade tip attachments 2124, 2134, 2144, as illustrated, may have a shape which extends outward over a greater portion of blades 2120, 2130, 2140 than that shown with respect to speculum 1100 (see, e.g., FIG. 12B). For example, in the illustrated embodiment of FIG. 13A, almost all of attachment 2124 attached to first blade 2120 protrudes away from the second blade 2130 and the third blade 2140. Similarly, almost all of attachment 2134 attached to second blade 2130 protrudes away from the first blade 2120 and the third blade 2140, and almost all of attachment 2144 attached to third blade 2140 protrudes away from the first blade 2120 and the second blade 2130. Such a shape, or series of shapes, may facilitate gripping or retention of the speculum in the vaginal walls 11 (see FIG. 6B, for example) while reducing the localized stress where the vaginal walls contact the blade tip attachments 2124, 2134, 2144. Also, as noted above, the blade tip attachments 2124, 2134, 2144 may similarly be removed and replaced with a different attachment if desired. For example, attachments such as blade tip attachments 2124, 2144 may be replaced with an attachment having a different shape such as that of blade tip attachments 1124 and/or 1144 (see FIG. 12B) described above. Each blade tip attachment may be releasably secured to one of blades 2120, 2130, and/or 2140 using adhesives, fasteners, and/or snap-fit features, for example.

Figure 14A:
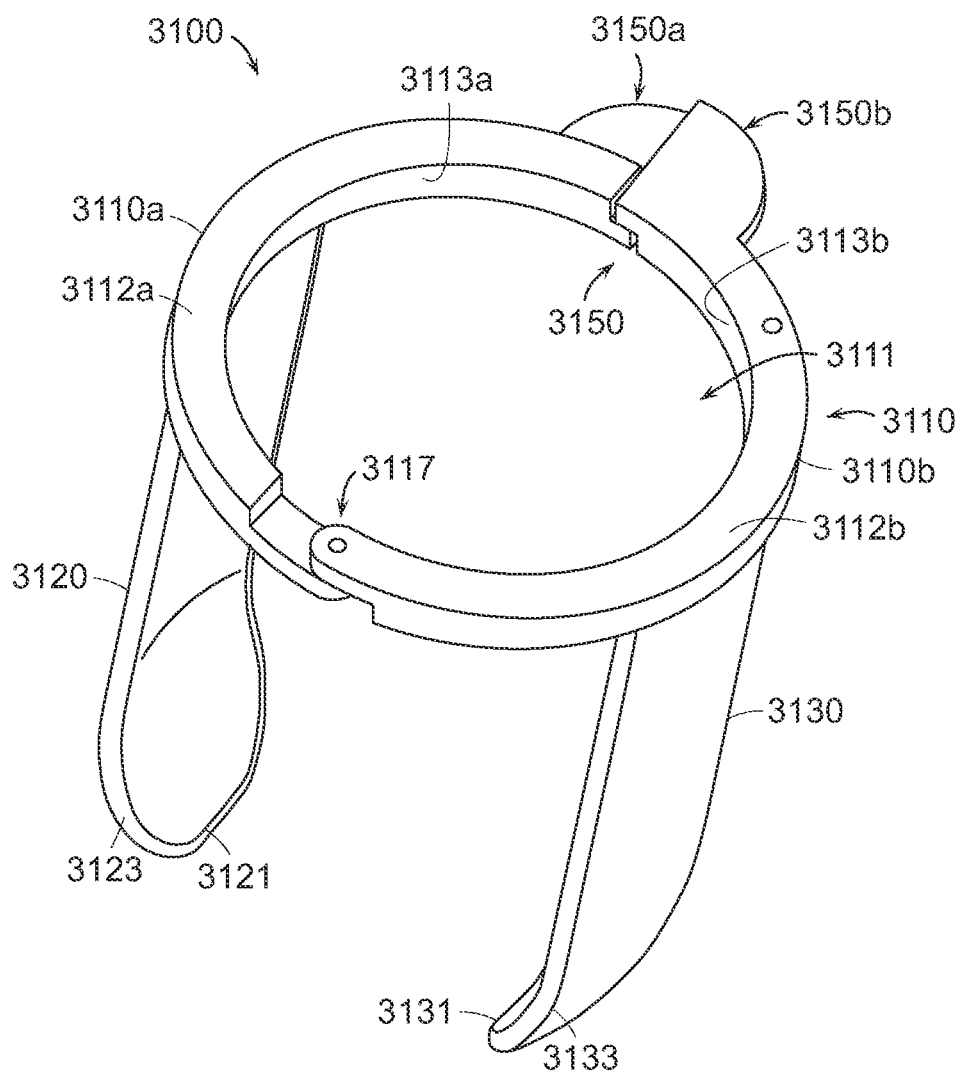
FIG. 14A is a perspective view of a speculum according to a non-limiting embodiment; the speculum is shown in an opened configuration.
Figure 14B:
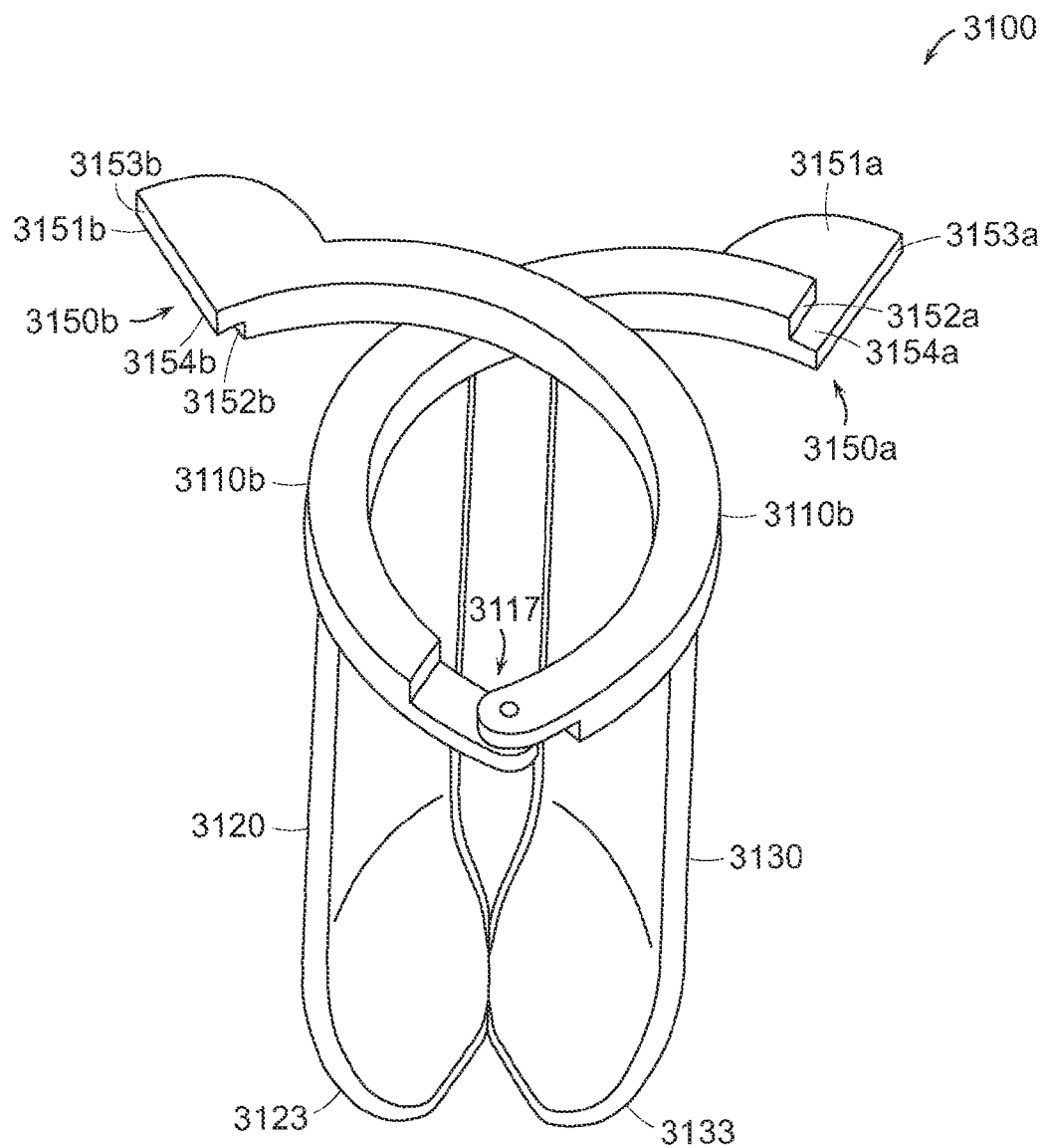
FIG. 14B is a perspective view of the speculum of FIG. 14B in a closed configuration.

In various embodiments, a speculum may include additional and/or different locking assemblies to those described herein, e.g., the ratchet assemblies. By way of example, a locking assembly may comprise a latch or catch that may work in conjunction with a hinge to allow the speculum blades to move relative to one another and subsequently be locked into an open position. In particular, FIGS. 14A-14B illustrate such a version of a hinged speculum, speculum 3100, that comprises a hinge 3117 disposed between a first blade 3120 and a second blade 3130. In such embodiments, the base 3110 may be divided into a first portion 3110*a* and a second portion 3110*b*. Further, referring to FIG. 14A, the speculum 3100 may include a locking assembly which may comprise at least one latch 3150 operably coupled to at least one of the first portion 3110a and the second portion 3110b. The latch 3150 may be configured to releasably hold the first portion 3110a and the second portion 3110b relative to each other in at least one locked position, as shown in FIG. 14A. Accordingly, speculum 3100, like other speculums described above, such as speculum 100, for example, can comprise a base 3110 defining an opening 3111 therethrough, e.g., as further defined by inner walls 3113a, 3113b of first and second base portions 3110a, 3110b, respectively, for insertably receiving at least one surgical device. Similar to speculum 100 and base 110, discussed above, the base 3110 can comprise at least one proximal surface, such as proximal surfaces 3112a and 3112b of first and second portions 3110a, 3110b, respectively. In the illustrated embodiment of FIG. 14A, when the speculum 3100 is in a locked configuration, as described in more detail below, the surfaces 3112a, 3112b may be approximately flush with each other. In other words, the surfaces 3112a, 3112b, as shown in FIG. 14A, can lie in substantially the same plane as defined by each surface 3112a, 3112b. Thus, the base portions 3110a, 3110b can together provide a level surface to support other surgical tools, as explained above.

Further, referring to FIGS. 14A-14B, the speculum 3100 can also comprise a first blade 3120 attached to the first base portion 3110a and a second blade 3130 attached to the second base portion 3110b. The blades 3120, 3130 may be attached to the base portions 3110a, 3110b, respectively, by adhering, fastening, and/or snapping the components together, for example. Further, the blades 3120, 3130 may be integrally formed with the base portions 3110a, 3110b, respectively, such that each are formed from the same material, e.g., a plastic or metal, and are contiguous with each other. In other words, the first blade 3120 may be integral and contiguous with first base portion 3110a and second blade 3130 may be integral and contiguous with second base portion 3110b. In any event, when the latch 3150 is unlocked, as explained below, the base portions 3110a, 3110b and thus the first blade 3120 and the second blade 3130 are movable with respect to each other and may be moved together into a closed position, such as a fully closed position shown in FIG. 14B, for insertion into or removal from a natural orifice, such as vagina 10, seen in FIG. 6A.

As noted above, referring to FIG. 14A, the speculum 3100 may include a locking assembly which may comprise latch 3150 operably coupled to the first portion 3110a and/or to the second portion 3110b. The latch 3150 may be configured to releasably hold the first blade 3120 and the second blade 3130 relative to each other in a locked position, as shown in FIG. 14A. Also, as mentioned previously, the latch 3150 may be unlocked such that the base portions 3110a, 3110b and, accordingly, blades 3120, 3130 may move relative to each other until the blades 3120, 3130 contact each other in a fully closed position as shown in FIG. 14B. Such movement is guided by hinge 3117, which may allow some separation and/or flexibility between base portions 3110a, 3110b such that one base portion slides over the other. For example, as shown in FIG. 14B, the hinge 3117 has permitted the base portions 3110a, 3110b to rotate about hinge 3117 while the second base portion 3110b slides or moves over the first base portion 3110a.

Further, referring to FIG. 14A, portions of latch 3150 may be formed (as shown) or attached to both of base portions 3110a, 3110b. For example, as best seen in FIG. 14B, latch 3150 (see FIG. 14A) can comprise a first latch portion 3150a coupled to first base portion 3110a and a second latch portion 3150b coupled to second base portion 3110b. Respectively, each latch portion 3150a, 3150b may comprise a projected surface 3153a, 3153b, a recessed surface 3152a, 3152b, and a stabilizing surface 3154a, 3154b extending transverse to one or both of surfaces 3152a, 3152b and 3153a, 3153b. Referring to FIGS. 14A-14B, the projected surfaces 3153a, 3153b are configured to engage and/or abut the recessed surfaces 3152a, 3152b, respectively, when the latch 3150 is locked as shown in FIG. 14A. Further, still referring to FIGS. 14A-14B, when the latch is locked (FIG. 14A), the stabilizing surfaces 3154a, 3154b are configured to contact each other to prevent the latch from unlocking undesirably; in other words, the stabilizing surfaces 3154a, 3154b help align the latch portions 3150a, 3150b such that the projected surfaces 3153a, 3153b properly interact with the recessed surfaces 3152a, 3152b. The latch further may comprise finger tabs 3151a, 3151b extending outward, away from each base portion 3110a, 3110b, respectively. The finger tabs 3151a, 3151b may facilitate the unlocking of latch 3150. For example, viewing FIG. 14A, the latch 3150 is shown locked, which, when in such a locked position inside a patient's vagina 10 (see FIG. 6B) may be held in the locked position of FIG. 14A by forces applied by vaginal walls 11 (see FIG. 6B) against blades 3120, 3130 which subsequently presses the base portions 3110a, 3110b together and creates friction between the surfaces 3152a and 3153b and/or surfaces 3152b and 3153a. Alternatively, the stabilizing surfaces 3154a and 3154b may include a tongue and groove feature such that the latch portions 3150a, 3150b are held together by friction created therebetween. In any event, thereafter, such frictional forces may be overcome when a user presses finger tabs 3151a, 3151b apart, thereby unlocking the latch 3150 to allow the base portions 3110a, 3110b and thus blades 3120, 3130 to be moved to a closed position, such as the fully closed position shown in FIG. 14B. Subsequently, the closed speculum 3100 may be removed from a patient after a surgical procedure is completed.

Further, one or both of speculum blades 3120, 3130 may respectively include a distal portion 3123, 3133 including a shape which is partially parabolic. In other words, the distal portions 3123, 3133 of blades 3120, 3130 may curve towards each other to ease insertion into a natural orifice, such as vagina 10, seen in FIG. 6A.

After closing the speculum 3100, as shown in FIG. 14B, the speculum 3100 may be inserted into a vagina 10 (see FIG. 6A), for example. After insertion, the speculum 3100 may be opened and locked into an open or locked position, as shown in FIG. 14A. Opening the speculum 3100 moves the blades 3120, 3130 apart and stretches, expands, or otherwise spreads apart the vaginal walls 11 (see FIG. 6B). Thereafter an otomy site 13 (see FIG. 6B) may be located and a surgical procedure performed therethrough, as described above.

Also, as noted above, speculum 3100 may serve as a support structure for at least one other surgical device. Thus, the proximal surfaces 3112a, 3112b of the base portions 3110a, 3110b may collectively serve as support or contact surfaces for at least one additional surgical device of a surgical system, for example, for a transorifice device 300 (see FIGS. 3 and 11). Referring briefly to FIG. 14A, and as discussed above, when the latch 3150 is locked such that the first and second blades 3120, 3130 are in the locked position as shown, the shortest distance between a first distal end 3121 of blade 3120 and the plane of the proximal surfaces 3112a, 3112b may be substantially equal to the shortest distance between the second distal end 3131 of blade 3130 and the plane of the proximal surfaces 3112a, 3112b. Accordingly, the proximal surfaces 3112a, 3112b of base portions 3110a, 3110b may serve collectively as support surfaces for another surgical device, where the entrance to the body, through taught otomy site 13 (see FIG. 6B), is at a known distance past the proximal surfaces 3112a, 3112b, thereby alleviating at least one potentially unknown variable from a surgical procedure.

The hinged speculum 3100 shown in FIGS. 14A-14B may include blades 3120, 3130 that are oriented with respect to each other such that they are not angled with respect to each other when viewed through opening 3111 and when in the open or locked configuration as shown in FIG. 14A. In other words, the blades 3120, 3130 mirror each other or are at 180 degrees to each other about annular base 3110. Accordingly, as seen in FIG. 14B, when the blades 3120, 3130 are fully closed, the blades are angled with respect to each other. Therefore, when inserted into a vagina, the blades 3120, 3130 may not provide a uniform insertion tip. Accordingly, in various embodiments, the speculum blades may be oriented, when closed, to provide a more uniform insertion tip.

Figure 15:
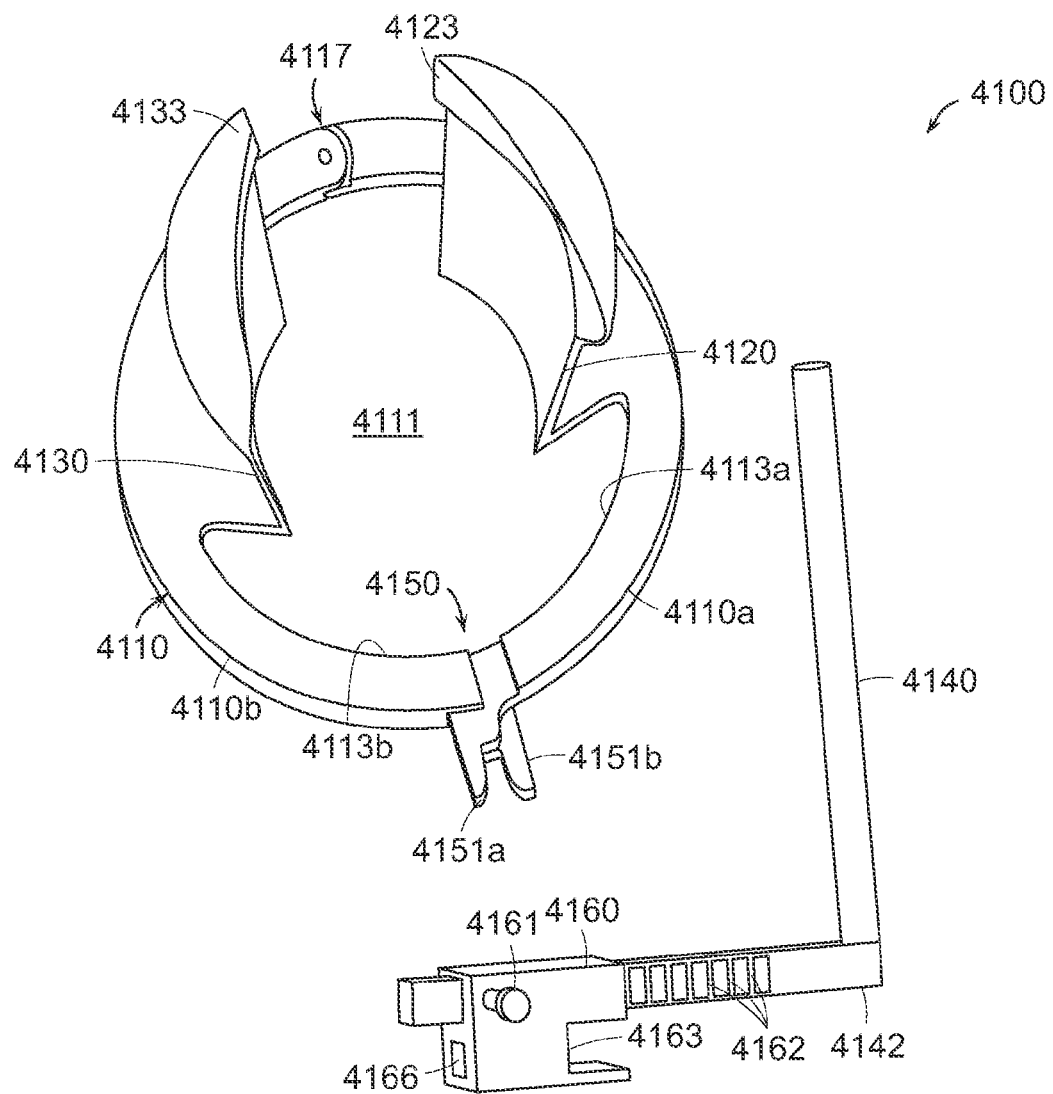
FIG. 15 is a bottom perspective view of a speculum according to a non-limiting embodiment; the speculum is shown in an open configuration and a detachable speculum blade is also shown laid on its side next to the speculum.

Referring now to FIG. 15, another version of a hinged speculum, speculum 4100 is illustrated. In this embodiment, the blades 4120, 4130 are oriented such that they are angled with respect to each other when viewed through opening 4111 defined by inner walls 4113a, 4113b and when in the open or locked configuration as shown in FIG. 15. However, the blades 4120, 4130 are not angled with respect to each other when the blades 4120, 4130 are rotated about hinge 4117 to a fully closed position. In other words, when a latch 4150 of speculum 4100 is unlocked, base portions 4110a, 4110b and, thus, the blades 4120, 4130 may be moved towards each other such that when the blades 4120, 4130 contact each other in a fully closed position (not shown), the blades 4120, 4130 mirror each other about base 4110. Therefore, in various embodiments, when inserted into a vagina, the blades 4120, 4130 may provide a more uniform insertion tip.

However, when the blades 4120, 4130 of speculum 4100 are opened to the locked position shown in FIG. 15, the two blades 4120, 4130 may not provide a balanced set of forces on vaginal walls into which the blades contact. Accordingly, speculum 4100 may further comprise a third blade 4140 that is attachable to and detachable from the base 4110 (shown detached in FIG. 15). In at least one embodiment, third blade 4140 is operably coupled to a ratchet assembly 4160, similar to ratchet assemblies described above in that ratchet assembly comprises a pawl (not shown) within the assembly that receives and operably engages teeth 4162 formed in support bar 4142 connected to blade 4140. As explained above with respect to ratchet assembly 160, the ratchet assembly may be unlocked and the pawl may be released form the teeth via button 4161. Further, as seen in FIG. 15, the ratchet assembly, and thus the blade 4140 may be attached to the open and locked speculum 4100 by inserting the finger tabs 4151a, 4151b of latch 4150 through a hole 4166 defined through a portion of ratchet assembly 4160 such that the base 4110 is received without a groove 4163 defined at the end of hole 4166. After attaching the ratchet assembly, the third blade 4140 may be moved and locked in a desired position relative to the first and/or second blade 4120, 4130.

Briefly, the speculum 4100 may be used as follows. The speculum 4100 may first be fully closed such that the blades 4120, 4130 mirror each other. Second, the speculum 4100 may then be inserted into a patient's vagina. Third, the speculum 4100 may be opened and the first and second blades 4120, 4130 locked via latch 4150 into the position shown in FIG. 15. Fourth, the third blade 4140 may be adjusted such that the blade 4140 is moved at least partially away from the ratchet assembly 4160, analogous to the closed positions described above with respect to ratcheted speculums 100, 1100, and/or 2100. Fifth, the third blade 4140 may be attached to the base 4110 as described above and the blade 4140 inserted into the vagina. Fifth, the third blade 4140 may be moved away from the other blades 4120, 4130 and toward ratchet assembly 4160 to an open and locked position. Accordingly, vaginal walls of the patient's vagina may be moved apart in a balanced fashion to create space for a surgical procedure therethrough.

After the surgical procedure is completed, the ratchet assembly 4160 may be unlocked by manipulating button 4161 and then the third blade 4140 may be moved away from the ratchet assembly, towards a closed position. Then, the ratchet assembly 4160 and blade 4140 can be detached from the base 4110 in reverse fashion to that with which they were attached thereto. Next, the finger tabs 4151a, 4151b may be pressed apart to release latch 4150 and unlock the speculum 4100 such that the first blade 4120 and the second blade 4140 may move towards each other into a closed position. Finally, the closed speculum 4100 may be removed from the patient.

Additionally, the blades 4120, 4130 of speculum may each comprise a distal portion 4123, 4133, respectively, which has an enlarged semi-spherical shape to assist with both insertion and gripping of the vaginal walls. Alternatively, as described above, the blades 4120, 4130 may have different shapes, including those disclosed herein. Further, while not shown, speculum blades according to various embodiments may include a roughened or textured surface to enhance gripping of the vaginal walls.

Figure 18:
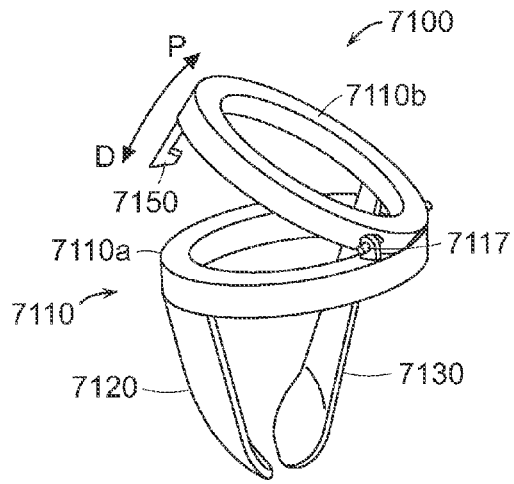
FIG. 18 is an illustration of a speculum according to a non-limiting embodiment.

As noted above, FIGS. 14A-15 illustrate various embodiments of hinged speculums that are low in profile and do not require a handle to operate. Another embodiment of a hinged speculum, speculum 7100, is shown in FIG. 18. Hinged speculum 7100 can include a base 7110 divided into a first portion 7110a and a second portion 7110b by a hinge 7117. Further, the speculum 7100 may comprise a first blade 7120 extending from the first base portion 7110a and a second blade extending from the second base portion 7110b. The second base portion 7110b may rotate in a proximal direction P and a distal direction D about hinge 7117. Accordingly, movement of the second base portion 7110b in a proximal direction P may rotate the second blade 7130 about hinge 7117 and toward the first blade 7120 to a closed or insertable position as shown in FIG. 18. Moving the second base portion 7110b in a distal direction D may subsequently move the second blade 7130 away from the first blade 7120 until the second base portion 7110b contacts the first base portion 7110a and thus places the blades 7120, 7130 into an open or expanded position. Once the speculum 7100 is opened, it may be locked in a locked position via at least one locking assembly, such as catch 7150 which extends from second base portion 7110b and is configured to snap onto or into a part of first base portion 7110a.

As discussed above, a speculum according to various embodiments may include additional and/or different locking assemblies to those described herein. By way of another example, a locking assembly may comprise a linkage or set of linkages to allow the speculum blades to move relative to one another and subsequently be locked into an open position. In particular, referring to FIGS. 16A-16C, in at least one exemplary embodiment, a linked speculum, such as speculum 5100 is illustrated. Speculum 5100 may be similar to other speculums described herein, in that speculum 5100 can comprise a base 5110 defining an opening 5111 therethrough, e.g., inner wall 5113 of base 5110 may define the opening 5111, and the base 5110 can also comprise a proximal surface 5112 which, similar to that discussed above at least with respect to speculum 100, may serve as a support surface for another surgical device. Further, speculum 5100 may comprise a first blade 5120 attached to the base 5110 and blade 5120 may include a first distal end 5121. Speculum 5100 may additionally comprise a second blade 5130 attached to the base and blade 5130 may also comprise a second distal end 5131. Similar to various embodiments described above, the blades 5120, 5130, may comprise distal portions 5123, 5133, respectively, that include a shape that is at least partially parabolic.

Figure 16A:
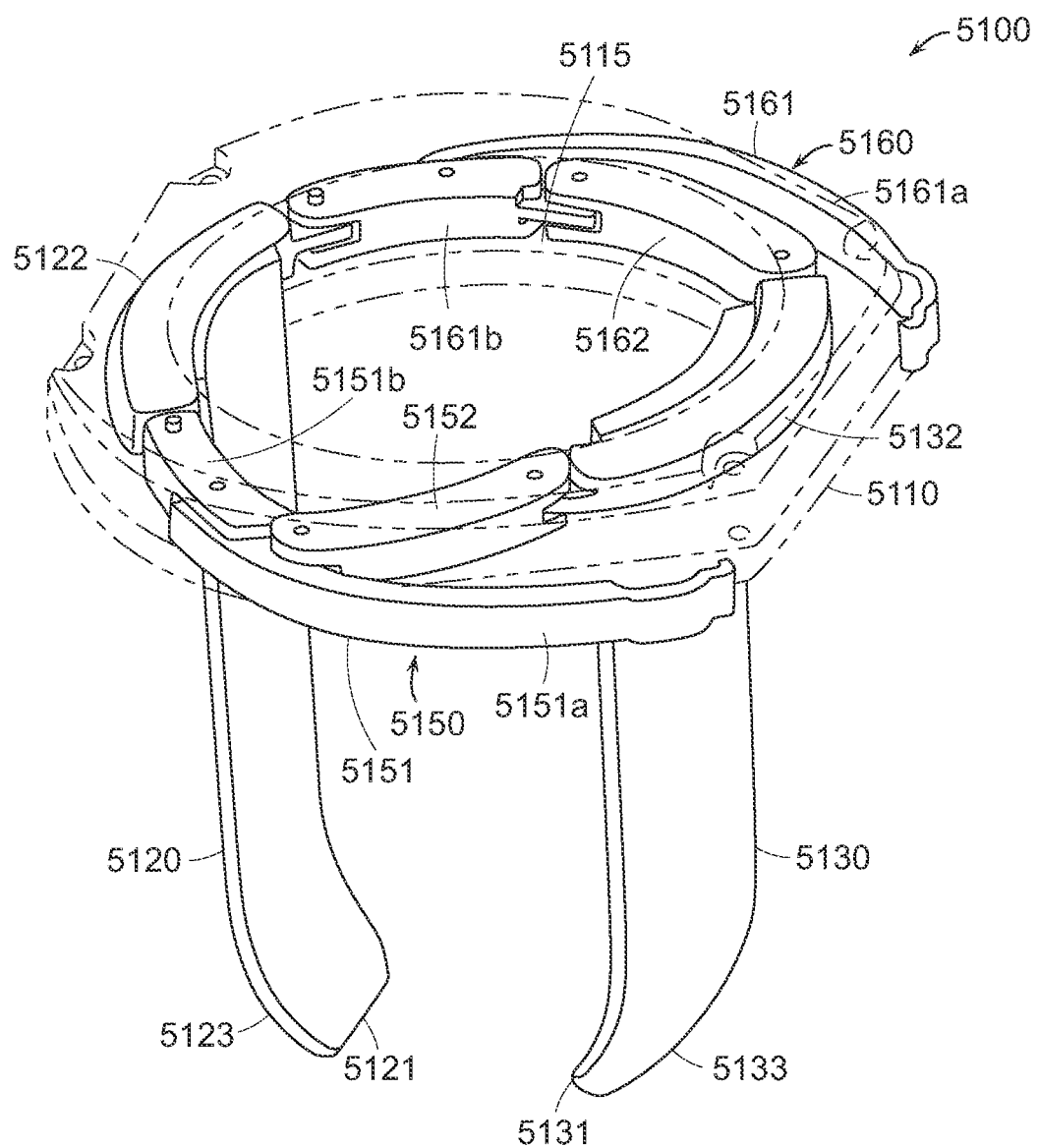
FIG. 16A is a perspective view of a speculum according to a non-limiting embodiment; the speculum is shown in a partially opened configuration.

The attachment of the blades 5120, 5130 to the base 5110 may be described as follows. Note, FIG. 16A shows the base 5110 in dashed lines to allow visualization of internal components. Each blade 5120, 5130 may extend from a support bar 5122, 5132 fixedly attached thereto or formed therewith. Further, the support bars 5122, 5132 may be received within a groove 5115 defined within base 5110. Also, the support bars 5122, 5132, as will be explained in more detail below, may cooperate with linkage assemblies 5150, 5160, portions of which may also be received within groove 5115, to attach blades 5120, 5130 to base 5110.

Figure 16B:
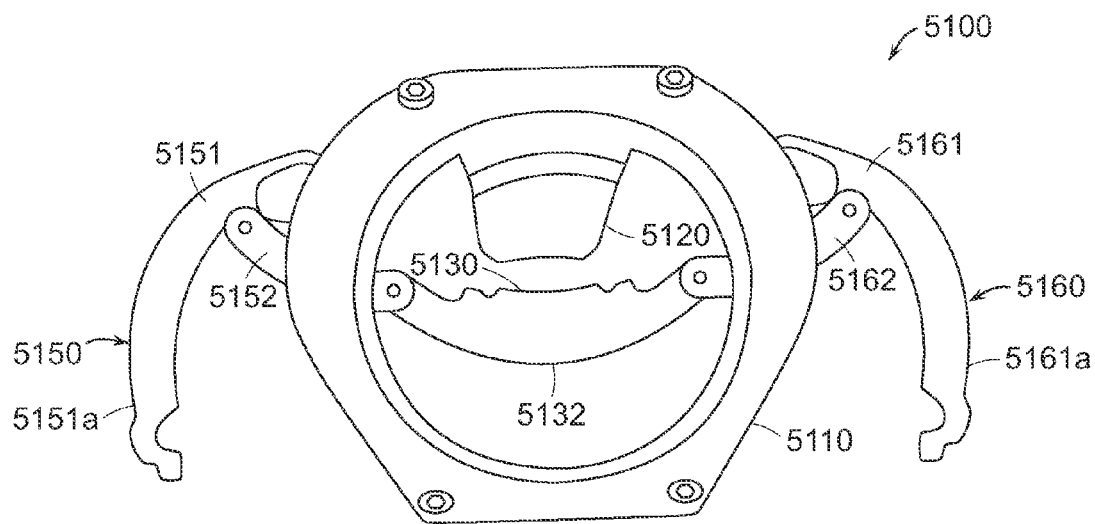
FIG. 16B is a top view of the speculum of FIG. 16A in a closed configuration.
Figure 16C:
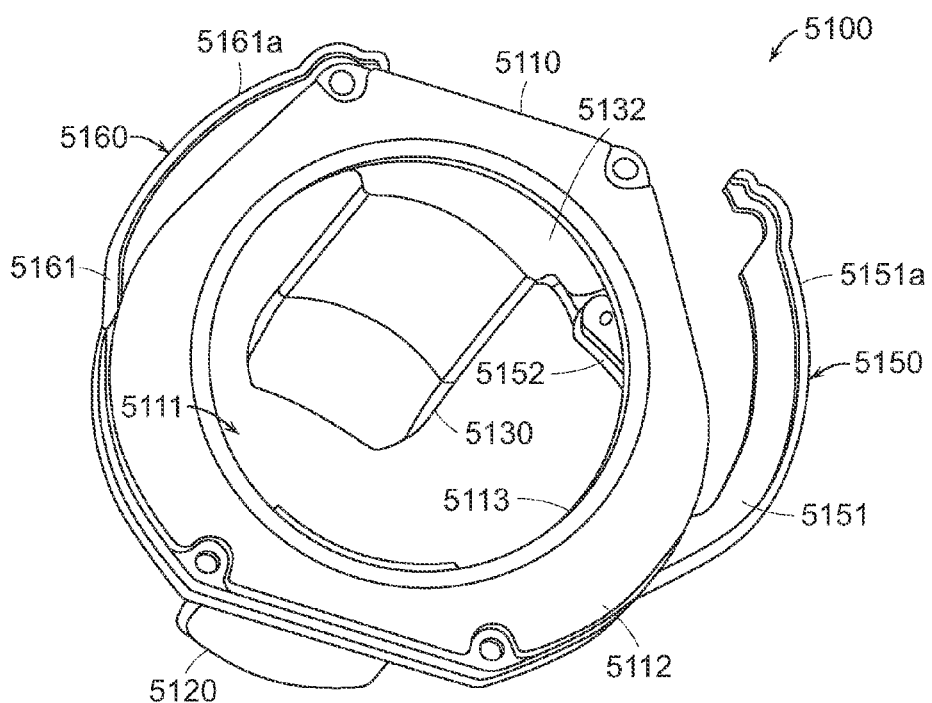
FIG. 16C is a top perspective view of the speculum of FIG. 16A in a partially opened configuration.

Additionally, the blades 5120, 5130 may also be movable with respect to each other to move between a closed position, as seen in FIG. 16B and an open position; FIGS. 16A and 16B show the blades 5120, 5130 approaching a fully opened position. In at least one embodiment, first blade 5120 may be fixedly attached to the base 5110 and the second blade 5130 may be movably attached to the base 5110. In such embodiments, the first support bar 5122 may be adhered, welded, formed, fastened, or otherwise fixedly connected to the groove 5115 in base 5110. Further, the second support bar 5132 may be configured to slide in and out of the groove 5115; for example, FIGS. 16A and 16C show the support bar 5132 at least partially slid into groove 5115 and FIG. 16B shows the support bar 5132 slid out of the groove 5115.

As with the other exemplary speculums described herein, the speculum 5100 may include one or more locking assemblies, such as first and second linkage assemblies 5150, 5160, that are configured to releasably hold the first blade 5120 and the second blade 5130 relative to each other in at least one locked position. Referring to FIG. 16A, in various embodiments, the first linkage assembly 5150 may be connected to the first blade 5120 and to the second blade 5130, on one side of the speculum 5100, and the second linkage assembly 5160 may be connected to the first blade 5120 and to the second blade 5130, on another side of the speculum 5100, for example.

Further, still referring to FIG. 16A, the first linkage assembly 5150 may comprise a first locking lever 5151 pivotally coupled to the first blade 5120 via support bar 5122 and a first link 5152 pivotally coupled to the second blade 5130 via support bar 5132. The first locking lever 5151 may also be pivotally coupled to the first link 5152. In more detail, the locking lever 5151 may include a finger operable portion 5151a that is configured to be pushed and/or pulled by a user to move the linkage assembly 5150, and, subsequently, to also move the second blade 5130 relative to the first blade 5120. Also, the locking lever 5151 may include a link portion 5151b integrally formed with or fixedly attached to the finger operable portion 5151a. The link portion 5151b may pivotally connect to both the first support bar 5122 and the first link 5152 at or near the ends of link portion 5151b. Likewise, the first link 5152 may be pivotally connected to both the link portion 5151b and the second support bar 5132 at or near the ends of first link 5152.

Moving now to the other side of speculum 5100, second linkage assembly 5160 may be similar to and/or mirror the first linkage assembly 5150 about base 5110. Accordingly, the second linkage assembly 5160 may comprise a second locking lever 5161 pivotally coupled to the first blade via support bar 5122 and a second link 5162 pivotally coupled to the second blade 5130 via support bar 5132. The second locking lever 5161 may also be pivotally coupled to the first link 5152. In more detail, and as with first linkage assembly 5150, the locking lever 5161 may include a finger operable portion 5161a that is configured to be pushed and/or pulled by a user to move the linkage assembly 5160, and, subsequently, to also move the second blade 5130 relative to the first blade 5120. Also, the locking lever 5161 may include a link portion 5161b integrally formed with or fixedly attached to the finger operable portion 5161a. The link portion 5161b may pivotally connect to both the first support bar 5122 and the second link 5162 at or near the ends of link portion 5161b. Likewise, the second link 5162 may be pivotally connected to both the link portion 5161b and the second support bar 5132 at or near the ends of second link 5162.

The first and second linkage assemblies 5150, 5160 and the first and second blades 5120, 5130, thus form a six-bar linkage, that, when the locking levers 5151, 5161, are pulled out, away from base 5110 via finger operable portions 5151a, 5151b, will move the blades 5120, 5130 toward each other, see, e.g., FIG. 16B. Likewise, referring to FIGS. 16A and 16C, when one or both of the locking levers 5151, 5161 are pressed in, toward base 5110 via finger operable portions 5151a, 5151b, the blades 5120, 5130 will move apart from each other. Further pressing down on the locking levers 5151, 5161 to reach a fully locked position will result in the six-bar linkage locking into position. For example, FIG. 16C shows locking lever 5161 in such a fully locked position, whereas locking lever 5151 is approaching the same. To unlock the linkage assemblies 5150, 5160, a user may pull on each lever 5151, 5161 via finger operable portion 5151a, 5161a to move the blades towards each other, see FIG. 16B. Accordingly, the speculum 5100 may be first closed as seen in FIG. 16B, then inserted into a patient's orifice, e.g., vagina 10 seen in FIG. 6A, and then opened and locked into an open position such as that seen in FIGS. 16A and 16C, or a fully open position. Then, a surgical procedure may be performed through the speculum 5100. After the procedure, the speculum 5100 may be unlocked and closed into a closed position, such as that seen in FIG. 16B, and removed from the patient.

The first and second linkage assemblies 5150, 5160 may be operated independently or in unison to move second blade 5130 relative to first blade 5120. It will be readily appreciated that, due to the linkage assemblies 5150, 5160, the second blade 5130 may be moved directly away or towards the first blade 5120 by operating both levers 5151, 5161 at the same time, see, e.g., FIG. 16B, or the second blade 5130 may be moved at an angle away or towards the first blade 5120, see, e.g., FIG. 16C by moving one lever farther towards or away from the base 5110. For example, in FIGS. 16A and 16C, lever 5161 is rotated closer to the base 5110 than is lever 5151, and thus, the blades are at an angle with respect to each other, see again, FIG. 16C. Accordingly, variances in patients' anatomy may be taken into account by adjusting the travel of one blade relative to the other.

Additionally, speculum 5100 may provide various additional advantages. For example, when the blades 5120, 5130 are in a locked position, the shortest distance between the first distal end 5121 and a plane defined by the proximal surface 5112 may be substantially equal to the shortest distance between the second distal end 5131 and the plane defined by the proximal surface 5112. Accordingly, the working distance from the proximal surface 5112, which, again, may serve as a support surface for another surgical instrument, to an otomy site located between the blades 5120, 5130 may be known, thereby helping remove anatomical variation between patients as a significant surgical factor.

Figure 17:
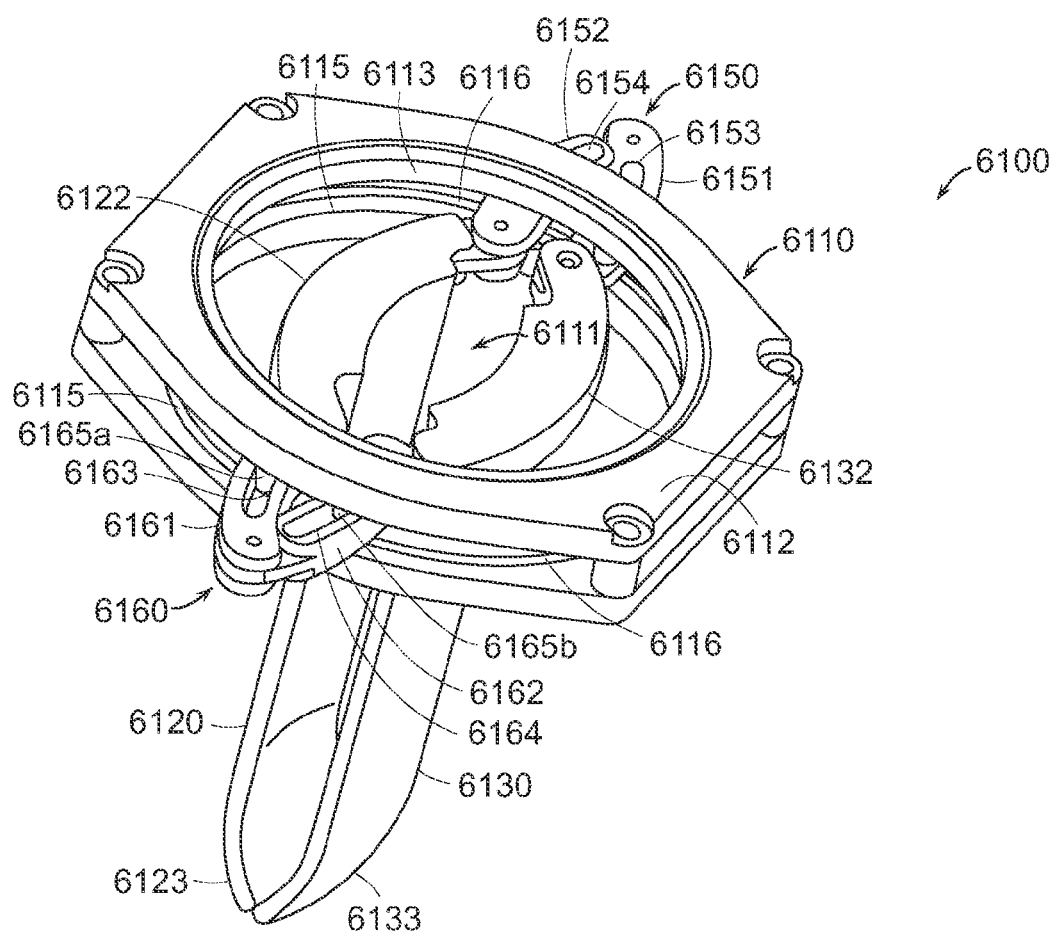
FIG. 17 is a perspective view of a speculum according to a non-limiting embodiment; the speculum is shown in a fully closed configuration.

As will be appreciated from the disclosure above, FIGS. 16A-16C illustrate at least one embodiment of a linked speculum that is low in profile and does not require a handle to operate. Another embodiment of a linked speculum, speculum 6100, is shown in FIG. 17. Generally, linked speculum 6100 may be similar to speculum 5100. However, notably, while the first blade 5120 of speculum 5100 may be fixedly attached to the base 5110, a first blade 6120 of speculum 6100 may be movable attached to a base 6110. Further, a second blade 6130 may also be movably attached to the base 6110. Accordingly, both blades 6120, 6130 of speculum 6100 may move away or towards each other; FIG. 17 depicts the blades 6120, 6130 after they have been moved together to a fully closed position with each of blades 6123, 6133 contacting each other.

In more detail, and similar to other speculums described herein, such as speculum 5100, speculum 6100 can comprise base 6110 defining an opening 6111 therethrough, e.g., inner wall 6113 of base 6110 may define the opening 6111, and the base 6110 can also comprise a proximal surface 6112 which, similar to that discussed above at least with respect to speculum 100, may serve as a support surface for another surgical device. Further, speculum 6100 may comprise first blade 6120 attached to the base 6110 and blade 6120 may include a first distal end 6121. Speculum 6100 may additionally comprise a second blade 6130 attached to the base 6110 and blade 6130 may also comprise a second distal end 6131. As described above, the blades 6120, 6130, may comprise distal portions 6123, 6133, respectively that have a shape that is at least partially parabolic.

The blades 6120, 6130 may be attached to the base 6110 as follows. Each blade 6120, 6130 may extend from a support bar 6122, 6132 fixedly attached thereto or formed therewith. Further, the support bars 6122, 6132 may be configured to fit, slide, and/or be received within a groove 6115 defined within base 6110. The support bars 6122, 6132 may cooperate with linkage assemblies 6150, 6160, portions of which may also be received within groove 6115, to attach blades 5120, 5130 to base 5110.

As with the other exemplary speculums described herein, such as speculum 5100, for example, the speculum 6100 may include one or more locking assemblies, such as first and second linkage assemblies 6150, 6160, that are configured to releasably hold the first blade 6120 and the second blade 6130 relative to each other in at least one locked position. Referring to FIG. 17, in various embodiments, the first linkage assembly 6150 may be connected to both the first blade 6120 and the second blade 6130, on one side of the speculum 6100, and the second linkage assembly 6160 may be connected to both the first blade 6120 and the second blade 6130, on another side of the speculum 6100, for example.

Further, still referring to FIG. 17, the first linkage assembly 6150 may comprise a first link 6151 pivotally coupled to the second blade 6130 via support bar 6132 and a second link 6152 pivotally coupled to the first blade 6120 via support bar 6122. The first link 6151 may also be pivotally coupled to the second link 6152. In more detail, the first link 6151 may pivotally connect to both the second support bar 6132 and the second link 6152 at or near the ends of link 6151. Likewise, the second link 6152 may be pivotally connected to both the first link 6151 and the first support bar 6122 at or near the ends of second link 6152. Additionally, to maintain a central positioning of blades 6120, 6130 in relation to opening 6111 and to provide a pair of fulcrum points against which the linkage assembly 6150 may be leveraged, the linkage assembly 6150 may further comprise a pair of pins (not shown), one of which may be disposed in each of arced channels 6153, 6154 formed in links 6151, 6152, respectively. The pins may be further sized and configured to slide in at least one slot 6116 formed in base 6110 within groove 6115. Accordingly, movement of either or both of links 6151, 6152 is controlled such that a portion of each arced channel 6153, 6154 remains within groove 6115 of base 6110.

Moving now to the other side of speculum 6100, second linkage assembly 6160 may be similar to the first linkage assembly 6150. Accordingly, the second linkage assembly 6160 may comprise a third link 6161 pivotally coupled to the first blade 6120 via support bar 6122 and a fourth link 6162 pivotally coupled to the second blade 6130 via support bar 6132. The third link 6161 may also be pivotally coupled to the fourth link 6162. In more detail, the third link 6161 may pivotally connect to both the first support bar 6122 and the fourth link 6162 at or near the ends of link 6161. Likewise, the fourth link 6162 may be pivotally connected to both the third link 6161 and the second support bar 6132 at or near the ends of link 6162. Additionally, similar to that described with respect to first linkage assembly 6150, to maintain a central positioning of blades 6120, 6130 in relation to opening 6111 and to provide a pair of fulcrum points against which the second linkage assembly 6160 may be leveraged, the linkage assembly 6160 may further comprise a pair of pins 6165$a$, 6165$b$. Pin 6165$a$ may be disposed in an arced channel 6163 formed in link 6161 and pin 6165$b$ may be disposed in an arced channel 6164 formed in link 6162. The pins 6165$a$ and 6165$b$ may be further sized and configured to slide in at least one slot 6116 formed in base 6110 within groove 6115. Accordingly, movement of either or both of links 6161, 6162 is controlled such that a portion of each arced channel 6163, 6164 remains within groove 6115 of base 6110.

Similar to that described above with respect to speculum 5100, the first and second linkage assemblies 6150, 6160 and the first and second blades 6120, 6130 of speculum 6100, thus form a six-bar linkage, that, when the one or both sets of links 6151, 6152 and 6161, 6162 are pulled or pushed out, away from base 6110, will move the blades 6120, 6130 toward each other, see, e.g., FIG. 17. Likewise, when one or both sets of links 6151, 6152 and 6161, 6162 are pressed in, toward base 6110, the blades 6120, 6130 will move apart from each other. Further pressing down on both sets of links 6151, 6152 and 6161, 6162 to reach a fully locked position will result in the six-bar linkage locking into position with the blades 6120, 6130 at their farthest position from each other (not illustrated). To unlock the linkage assemblies 6150, 6160, a user may push on one or both of links 6151, 6152 and 6161, 6162, respectively, from within the opening 6111 to unlock and move the blades towards each other, see FIG. 17. Accordingly, the speculum 6100 may be first closed as seen in FIG. 16B, then inserted into a patient's orifice, e.g., vagina 10 seen in FIG. 6A, and then opened and locked into an open position analogous to that shown with respect to speculum 100 in FIG. 6B. Then, a surgical procedure may be performed through the speculum 6100. After the procedure, the speculum 6100 may be unlocked and closed into a closed position, such as that seen in FIG. 17, and removed from the patient.

Similar to that described above with respect to link speculum 5100, the first and second linkage assemblies 6150, 6160 of speculum 6100 may be operated independently or in unison to move the first and/or second blade 5130 relative each other. It will be readily appreciated that, due to the linkage assemblies 6150, 6160, the second blades 6120, 6130 may be moved directly away or towards each other by operating both linkage assemblies 6150, 6160 at the same time, see, e.g., FIG. 17, or the blades 6120, 6130 may be moved at an angle away or towards each other by moving one linkage assembly 6150, 6160 farther towards or away from the base 6110. For example, although not illustrated, linkage assembly 6150 may be pressed into a locked position, while the other linkage assembly 6160 is not in a locked position and, thus, the blades may be at an angle to each other. Accordingly, variances in patients' anatomy may be taken into account by adjusting the travel of one blade relative to the other.

Additionally, speculum 6100 may provide various additional advantages. For example, when the blades 6120, 6130 are in a locked position, the shortest distance between the first distal end 6121 and a plane defined by the proximal surface 6112 may be substantially equal to the shortest distance between the second distal end 6131 and the plane defined by the proximal surface 6112. Accordingly, the working distance from the proximal surface 6112, which, again, may serve as a support surface for another surgical instrument, to an otomy site located between the blades 6120, 6130 may be known, thereby helping remove anatomical variation between patients as a significant surgical factor.

Figure 19:
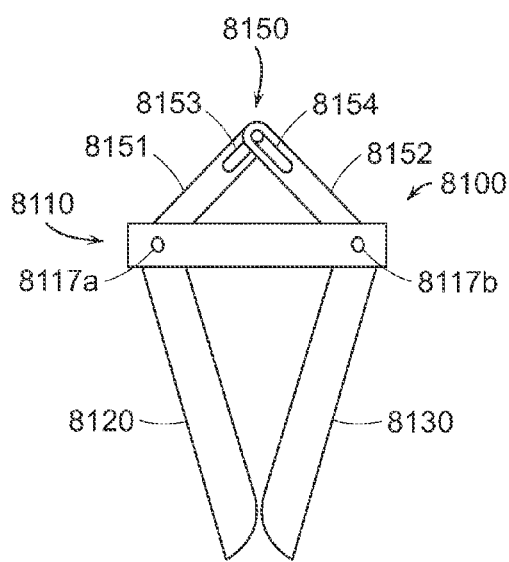
FIG. 19 is an illustration of a speculum according to a non-limiting embodiment.

As noted above, the features illustrated or described in connection with one embodiment may be combined with the features of other embodiments. By way of non-limiting example, and referring now to FIG. 19, a speculum, such as speculum 8100, may include both hinged and linked features to move and/or lock blades 8120, 8130 relative to each other. A side view of speculum 8100 is shown in FIG. 19. Speculum 8100 may include a first blade 8120 pivotally connected to a base 8100 via first hinge 8117a and a second blade 8130 pivotally connected to the base 8100 via second hinge 8117b. The blades 8120, 8130 may be moved in relation to each other and opened to a locked position via a locking assembly in the form of linkage assembly 8150 comprising first and second links 8151, 8152. In more detail, extending from first blade 8120 may be first link 8151 which may also be integrally formed with or otherwise fixedly attached to the blade 8120 such that both the blade 8120 and the link 8151 may rotate in fixed relation about hinge 8117a. Likewise, extending from second blade 8130 may be second link 8152 which may also be integrally formed with or otherwise fixedly attached to the blade 8130 such that both the blade 8130 and the link 8152 may rotate in fixed relation about hinge 8117b. Further, the links may be movably connected by a first pin (not shown) protruding from first link 8151 that is slidably received within a second channel 8154 formed within second link 8152. Similarly, a second pin (not shown) may protrude from the second link 8152 that is slidably received within a first channel 8153 formed within first link 8151. Accordingly, the links 8151, 8152 may be moved, in a proximal direction, away from the base 8110 to a closed position, such as the fully closed position shown in FIG. 19, where the blades 8120, 8130 are contacting each other. Similarly, the links 8151, 8152 may be moved, in a distal direction, toward base 8110 to an open position (not illustrated). Further moving the links 8151, 8152 toward the base 8110 may lock the blades 8120, 8130 in an open or locked position. Such opening and closing of the blades 8120, 8130 may be used to hold open a natural orifice, such as vagina 10 seen in FIGS. 6A-6B, for example, during a surgical procedure, as described herein. Also, the first linkage assembly 8150 may function on one side of the base 8110 and a second linkage assembly (not shown) may function in a similar fashion on another side of the base 8110. In any event, the speculum 8100 may provide various advantages as described with respect to other speculums taught herein.

The various speculum embodiments described herein may include various materials for the speculum components. For example, the various parts of the speculum may be made from a clear plastic to allow visualization of the patient's tissues. Further, the materials may be made of any color to help indicate various portions which are to be operated by a user. Additionally, the materials may be disposable after use. Such disposable materials may include polycarbonate. However, the materials may be re-sterilized after use. Such re-sterilizable materials may include polysulfone. Further, the materials may also be one or more metals, such as stainless steel, aluminum, magnesium, and titanium, for example. Various combinations of materials, such as those outlined above, are also possible. For example, the base may be made from a plastic, while the blades are made from a metal.

Further, additional modifications and/or uses of the speculums described herein are encompassed by various embodiments. By way of a first, non-limiting example, a light port may be added to at least one of the speculum blades to disperse light. In such embodiments, the light dispersing blade (s) may be made from a clear polycarbonate and an independent light source may be coupled to the blade(s) to cause light to travel through the blade and radiate light or glow, thereby providing enhanced lighting of the vagina and/or the otomy site therein, for example. Alternatively, a light tube, e.g., a fiber optic cable, may be added to one or more of the speculum blades to enable light to be fed to a distal portion of the blade. Light of any frequency may be provided. In at least one embodiment, the light frequency may be tuned or chosen to provide enhanced viewing of the tissue, e.g., the vaginal walls. Further, to better enable a user to see through a distal portion of at least one of the blades, one or more blades may include a video camera lens which may provide a signal to an external monitor, for example.

By way of a second, non-limiting example, a suction, a pressure, and/or an irrigation port may be added to one or more of the speculum blades. Such a port may be incorporated into the blade shape itself or independent tubing may run through the blade. Further, the port may be a carbon dioxide port which may assist with insufflation.

By way of a third, non-limiting example; a speculum may be configured for use through a body wall, such as the abdominal wall, and not through a natural orifice. In such embodiments, the speculum may function to help dilate an incision to increase the working area therethrough. In at least one embodiment, one or more of the distal ends of the speculum blades may form a sharp point. Further, all of the distal ends of the speculum blades may forma sharp point, that, when the speculum is in a closed configuration, cooperate together to form an incising point. The incising point may be applied to a patient's body wall, e.g., the abdominal wall, to incise the wall and pass the blades therethrough. Then, the speculum blades may be opened, thereby dilating the incision. In at least one embodiment, the speculum base and/or locking assembly/assemblies may be advanced until at least one of them contacts the exterior of the patient. Thereafter, a plug, such as the transorifice device described above, may be added to permit a sealed, port-based surgical procedure to be completed utilizing endoscopic, including laparoscopic, tools, for example. In such embodiments, a port, such as the suction, pressure, and/or irrigation port mentioned above, may be used to perform additional functions through the speculum (e.g., insufflation) without requiring additional incisions beyond that needed to introduce the speculum through the body wall.

By way of a fourth, non-limiting example, one or more speculum blades may include a conduit that forms a channel other delivery mechanism for providing various energy or signals to and/or from the blades. For instance, the blades may include an energy delivery mechanism for producing radio frequency energy, for example, to assist with coagulation. Additionally, ultrasound and/or laser energy may also be produced from a portion, e.g., a distal portion, of the speculum blade(s). Further, imaging modalities, such as static pictures, or dynamic videos may be recorded at or through the blades and passed to an external recording media. In any event, such energy and/or signal transmission may be passed through wires embedded in or pass along a surface of one or more of the speculum blades.

By way of a fifth, non-limiting example, in embodiments including a port or other conduit, such as those described above, a manifold may be incorporated into the speculum, near the base, for example, to allow multiple inputs and/or outputs. The outputs may be connected to an extension, either rigid or flexible, that allows one to continue to perform the functions of the manifold, such as irrigation, suction, and/or energy deliver, for example.

By way of a sixth, non-limiting example, one or more sensors may be incorporated into one or more of the speculum blades. Such sensors may provide various types of feedback, including, but not limited to, their position relative to one another or their depth in a patient's body, temperature, moisture, heart rate, blood pressure, and the like. Any such sensor(s) may also provide anatomical and/or calibration reference indicators for a user.

By way of a seventh, non-limiting example, one or more of the speculum blades may be configured to deliver a drug. In such embodiments, the blade(s) may provide a port or conduit through which a needle, or extendable needle, may pass through to allow direct injection into a patient's body, through the speculum blade(s).

Figure 21:
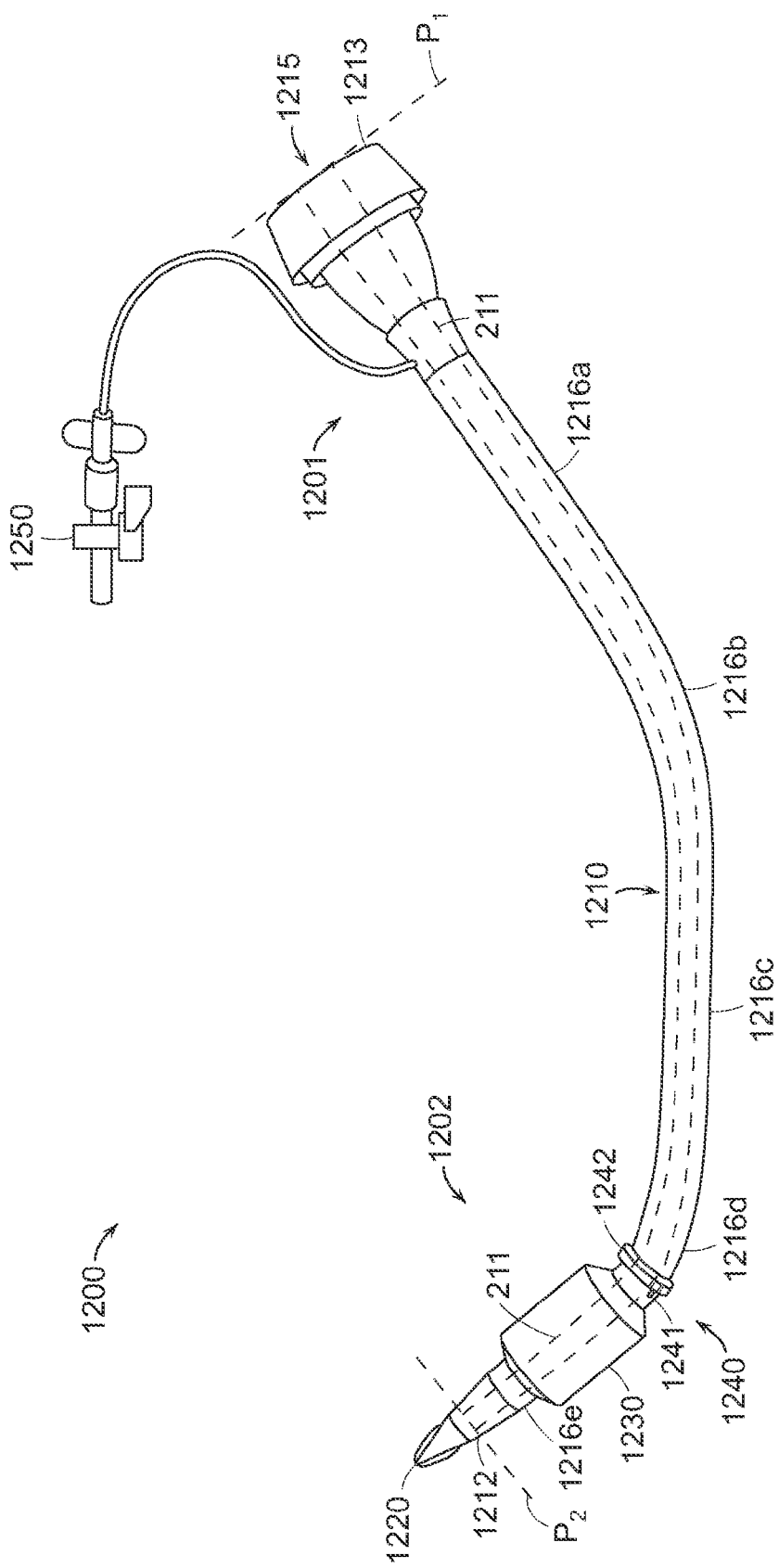
FIG. 21 is a side view of a surgical delivery device according to a non-limiting embodiment.

In various embodiments, additional surgical delivery devices and related surgical delivery device features are envisioned which may, among other things, provide similar advantages to that described above with respect to surgical delivery device 200 and may also be substituted for surgical delivery device 200 in a surgical system, kit, and/or method such as that shown and portrayed in one or more of FIGS. 1-11. For example, FIGS. 21-22C illustrate a non-limiting embodiment of a surgical delivery device 1200. Surgical delivery device 1200 may be similar to surgical delivery device 200. For instance, the surgical delivery device 1200 may also include a body 1210, a tip 1220, and a balloon 1230. The body 1210 may comprise a proximal end 1213 and a distal end 1212. A tool receiving passageway 1211 may be defined by body 1210 and include a proximal opening 1215 located at the proximal end 1213 and a distal opening 1214 (see, e.g., FIG. 22B) located at the distal end 1212. As noted above with respect to surgical delivery device 200, a body, such as body 1210 may be rigid and define at least one curve corresponding to the passageway 1211.

In more detail regarding the curved shape of a surgical delivery device, in various embodiments, referring now to FIG. 21, a side view of a surgical delivery device 1200 is shown. The body 1210 may be further shaped to assist a surgeon using the surgical delivery device 1200 to enter a patient's body cavity, through a vagina, for example, at a desired angle and position. Accordingly, the body 1210 may define multiple curves and/or linear portions. For example, the body 1210 may include a linear, first section 1216a, a curved, second section 1216b, a linear, third section 1216c, a curved, fourth section 1216d, and a linear, fifth section 1216e. Further, in at least one embodiment, referring to FIGS. 21 and 22B, the proximal opening 1214 and/or the proximal end 1212 of body 1210 may define a first plane P1 (transverse to the plane of the page of FIG. 21), and the distal opening 1214 and/or the distal end 1215 of body 1210 may define a second plane P2 (also transverse to the plane of the page of FIG. 21). The first plane P1 and the second plane P2 may intersect, thereby providing an entry angle at the proximal opening 1215 that is different from an exit angle at the distal opening 1214.

Figure 22A:
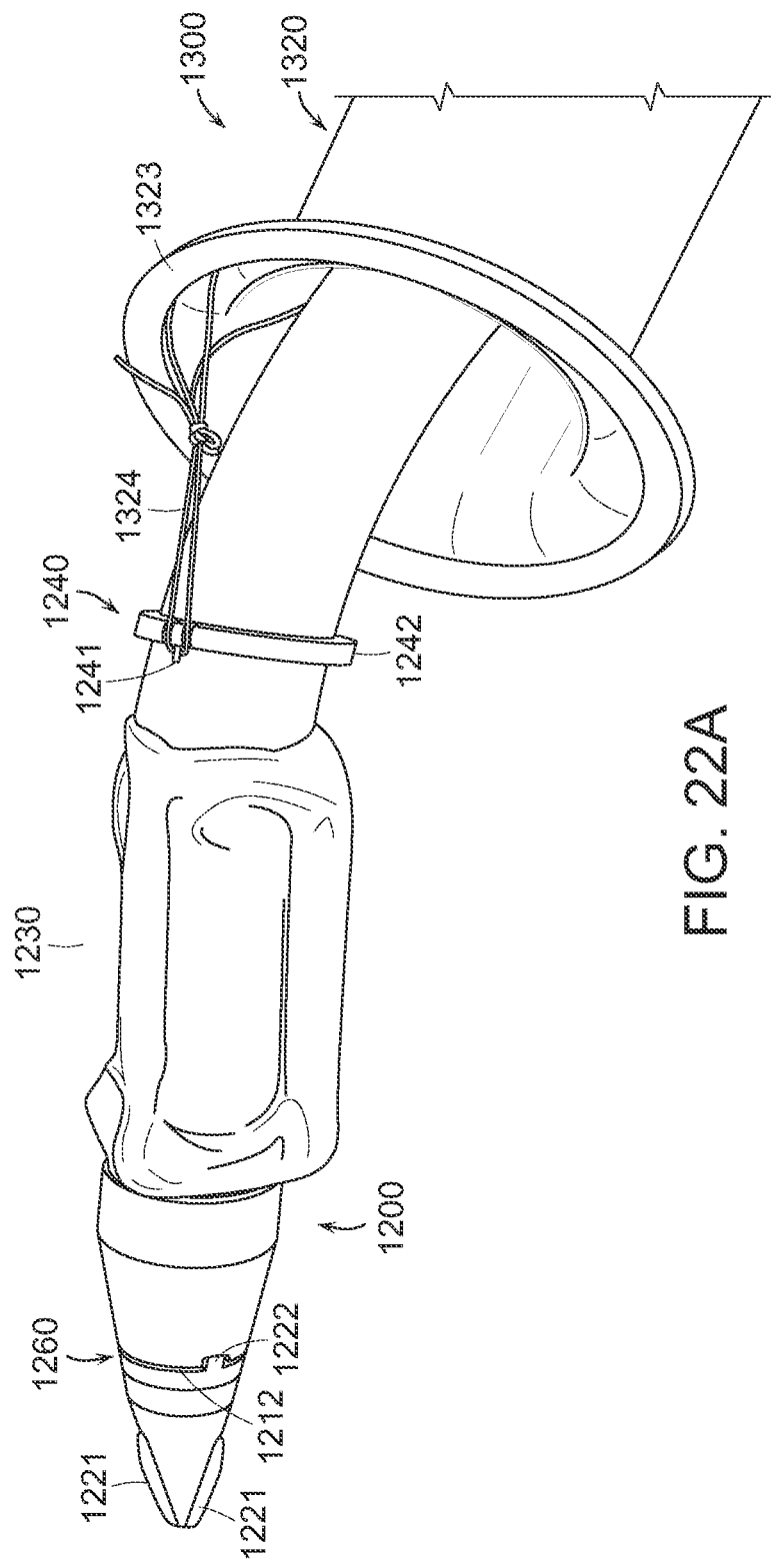
FIG. 22A illustrates the distal portion of the surgical delivery device of FIG. 21 extending through a distal end of a transorifice device and connected to a suture located at the distal end of the transorifice device; a dilating balloon of the surgical delivery device is in a deflated state and a distal tip of the surgical delivery device is in a closed position.
Figure 22B:
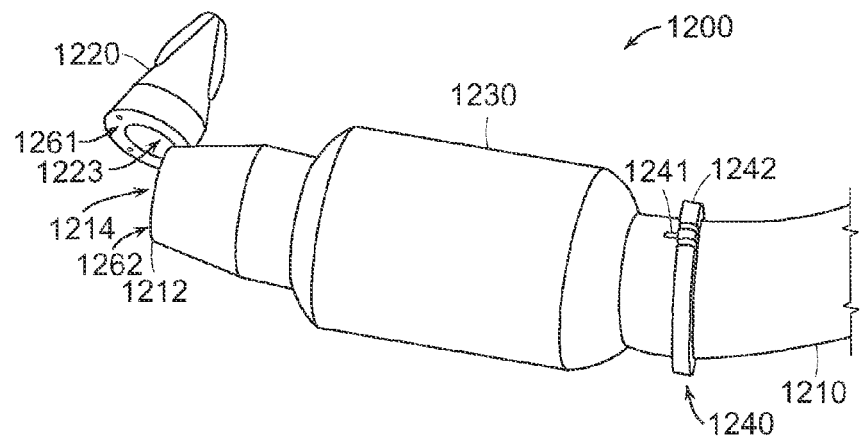
FIG. 22B illustrates the distal portion of the surgical delivery device of FIG. 22A; the distal tip of the device is shown in an opened position and a dilating balloon of the surgical delivery device is in an expanded state.
Figure 22C:
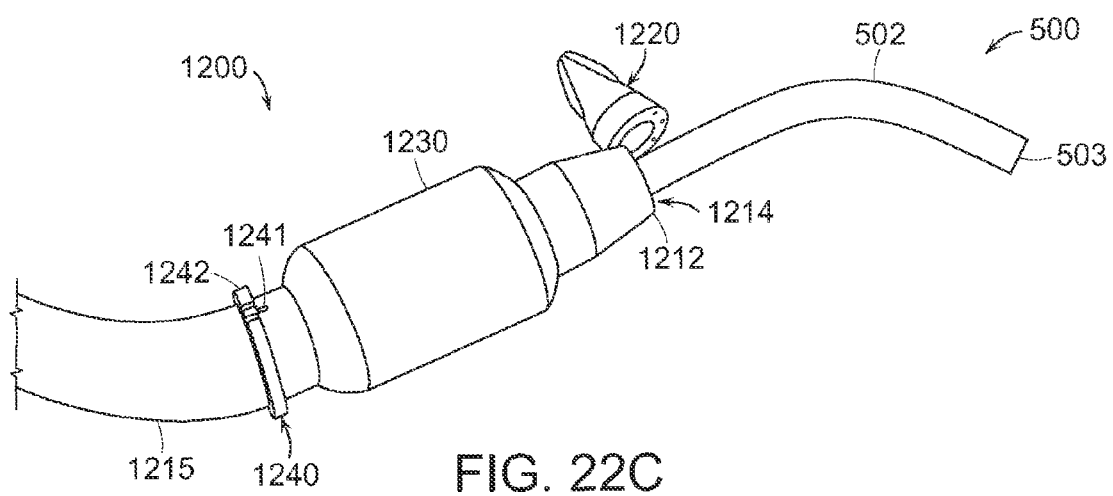
FIG. 22C illustrates a distal portion of the surgical delivery device of FIG. 22B with a portion of an endo scope extending past the opened tip.

Focusing now on tip 1220 and FIGS. 22A-22C, the surgical delivery device 1200, similar to that described with respect to delivery device 200, may further comprise a tip 1220 movably mounted to the distal end 1213 of the body 1210 such that the tip 1220 can move between an opened position (see, e.g., FIG. 22B) and a closed position (see, e.g., FIG. 22A). As explained above with respect to surgical delivery device 200, the tip 1220 of delivery device 1200 may conceal a portion of a surgical tool (e.g., endoscope 500 seen in FIG. 22C), that is inserted into passageway 1211, such that the tool may be revealed and/or delivered to a body cavity within a patient, such as peritoneal cavity 20, see, e.g., FIG. 10.

As explained above with respect to delivery device 200, the tip 1220 may be mounted to the distal end 1213 of the body 1210 in various ways. For example, referring to FIG. 22A, the tip 1220 may be mounted to the distal end 1213 by a hinge 1222. However, during use, it may be undesirable for the surgical delivery device's tip to open prematurely. Accordingly, in various embodiments, a surgical delivery device, such as surgical delivery device 1200 seen in FIGS. 21-22B, may comprise a catch 1260 located at the distal end 1212 of the body and configured to releasably hold the tip 1220 over the distal opening 1214 in a closed position, see FIG. 22A, such that the tip 1220 does not inadvertently open to the position seen in FIG. 22B. In more detail, referring to FIG. 22B, the catch may further include a first magnetic portion 1261 located at the tip 1220 and a second magnetic portion 1262 located at the distal end 1212. The first magnetic material 1261 may be magnetically attracted to the second magnetic portion 1262 such that opening the tip 1220 requires a certain amount of force, that may be provided by advancing endoscope 500 through the surgical delivery device 1200 such that the endoscope's distal end 503 pushes the tip 1220 open, see FIG. 22C.

Also as noted above with respect to surgical delivery device 200, referring now to FIGS. 22A-22C, the tip 1220 of delivery device 1200 may comprise a material that is at least partially transparent to facilitate viewing therethrough. However, in at least one embodiment, the transparent tip 1220 may further include a cavity 1223 that is configured to receive a distal end 503 of an endoscope 500. Accordingly, the distal end 503 of the endoscope 500 may rest inside cavity 1223 such that the tissue and/or organs near the tip 1220 may be visualized during a surgical procedure.

Further, also similar to that described with respect to surgical delivery device 200, the tip 1220 of delivery device 1200 may be configured to incise tissue. For example, referring to FIG. 22A, in at least one embodiment, the tip 220 may taper and/or include incising blades or wings 1221 extending outwardly therefrom. Such incising wings 1221 may be useful for cutting and/or separating tissue, such as the tissue at otomy site 13, seen in FIG. 6B.

Again, similar to that discussed above with respect to surgical delivery device 200, the surgical delivery device 1200 may be configured to dilate an incision by expanding a balloon 1230 that surrounds at least part of the body 1210 and that may be located adjacent the distal end 1212 of the body 1210. The balloon 1230 is shown in an unexpanded and/or deflated configuration in FIG. 22A and in an expanded and/or inflated configuration in FIG. 22C, for example. In at least one embodiment, referring to FIG. 21, the balloon 1230 may be inflated by providing a gas, such as air, nitrogen, and/or carbon dioxide, through a port 1250 operably coupled to the body 1210. Alternatively, a liquid, or a liquid mixed with a gas, may be used to expand the balloon 1230 through port 1250. The port 1250 may include a stopcock valve to maintain gas and/or liquid pressure in balloon 1230, after liquid and/or gas is introduced into the balloon 1230. In any event, a tube or other conduit (not shown) may connect the port 1250 with the balloon 1230 through body 1210 along or within passageway 1211.

Similar to balloon 230 described above with respect to surgical delivery device 200, as illustrated in FIGS. 21 and 22B-22C, the balloon 1230, when expanded, may have a shape with outward sides that are linear, as viewed from the side. In other words, the balloon 1230 may have a uniform, straight shape in a proximal-to-distal (or vice-versa) direction. However, as explained above, various configurations are possible for the balloon 1230 to expand and dilate tissue at an incision or other opening into a patient's body and/or body cavity.

In various embodiments, as with surgical delivery device 200, the surgical delivery device 1200 may also serve to assist in the proper placement and/or sealing of a transorifice device, such as transorifice device 1300 within a body cavity. For example and referring to FIG. 22A, in at least one embodiment, the surgical delivery device 1200 may further comprise a suture holder 1240 located near the distal end 1212 of the body 1210, wherein the suture holder 1240 is configured to releasably hold a suture, such as suture 1324 from the transorifice device 1300 (discussed below). As shown in FIG. 22A, the suture holder 1240 may be positioned on or along the body 1210 proximal to the balloon 1230. Notably, this arrangement is different than that discussed above with respect to surgical delivery device 200. Here, owing to the relative position of suture holder 1240 and balloon 1230, the held suture 1324 need not pass over the balloon 1230 and, therefore, the suture 1324 may be less likely to interfere with the balloon-tissue interface when the balloon 1230 expands within an incision. In more detail, as best seen in FIGS. 22A-22B, the suture holder may comprise a hook or protrusion 1241 that is configured to releasably snag a suture, such as suture 1324. Further, the protrusion may extend from and/or be integrally formed with a collar 1242 that is attached to the body 1210. Accordingly, when the protrusion 1241 is advanced in a distal direction (to the left of FIG. 22A, for example), the suture holder 1240 may snag and releasably hold the suture 1324. Then, the suture 1324 may be released when the protrusion 1241 is moved in a proximal direction (to the right of FIG. 22A, for example). Thus, the suture holder 1240 may allow for the surgical delivery device to pull transorifice device 1300 via suture 1324 and then release the transorifice device 1300 at a desired position and/or location.

In various embodiments, additional transorifice devices and related transorifice device features are envisioned which may, among other things, accomplish similar advantages to that described above with respect to transorifice device 300 and may also be substituted for transorifice device 300 in a surgical system, kit, and/or method such as that shown and portrayed in one or more of FIGS. 1-11. For example, referring to FIGS. 23A-23E, a non-limiting embodiment of an exemplary transorifice device, transorifice device 1300, is shown.

Figure 23A:
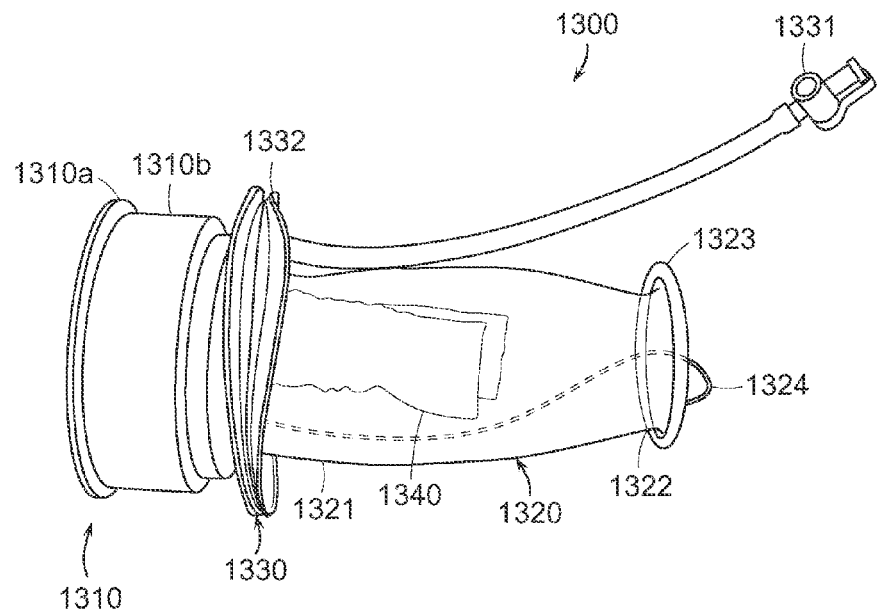
FIG. 23A is a side view of a transorifice device according to a non-limiting embodiment.
Figure 23B:
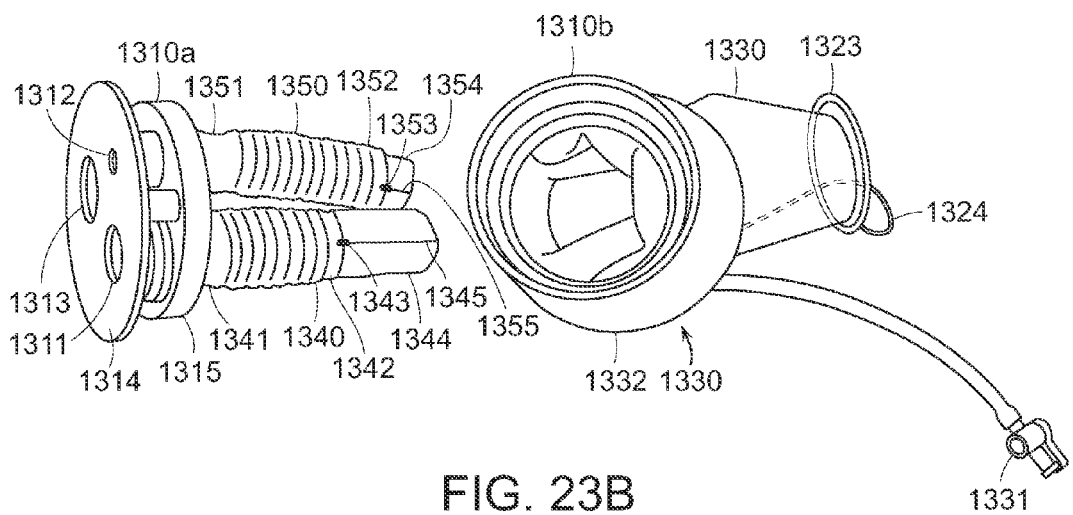
FIG. 23B is an illustration of the transorifice device of FIG. 23A with a port portion of a port assembly detached from a conduit portion of the port assembly.

Transorifice device 1300 may be similar to transorifice device 300. For instance, referring to FIG. 23A, which shows a side view of transorifice device 1300, transorifice device 1300 may comprise a port assembly 1310 and a flexible conduit 1320. In at least one embodiment, the transorifice device may further comprise at least one support member 1330. Referring to FIG. 23D, which shows a top perspective view of the transorifice device 1300, the port assembly 1310 may define at least one port therein, such as first port 1311, second port 1312, and third port 1313. Referring to FIGS. 23A and 23B, the port assembly 1310 may also have a proximal side 1314 and a distal side 1315 (see FIG. 23B). The flexible conduit 1320 may extend from the distal side 1315 of the port assembly 1310 and may also have a proximal portion 1321 adjacent to the port assembly 1310 and a distal portion 1322. The support member 1330 may be movably associated with the distal portion 1322 of the flexible conduit 1320 and extendable to the distal side of the port assembly 1310.

Referring briefly to FIGS. 23A and 23B, the port assembly 1310 may additionally comprise a port portion 1310a and a conduit portion 1310b that are detachable from each other. FIG. 23A shows the port portion 1310a coupled to the conduit portion 1310b and FIG. 23B shows the port portion 1310a detached from the conduit portion 1310b. The conduit portion 1310b may be attached to the flexible conduit 1320 and the port portion 1310a may include ports 1311, 1312, 1313. As mentioned above with respect to transorifice device 300, such collective detachment of ports 1311, 1312, 1313 may facilitate removing tissue and/or organ specimens from a patient's body during a surgical procedure. The port portion 1310a may be releasably attached to the conduit portion 1310b by a threaded and/or snap-fit engagement between the portions 1310a, 1310b, for example. Further, one or more release buttons may be included as part of either or both of portions 1310a, 1310b to enable a user to quickly and easily decouple the two portions 1310a, 1310b of the port assembly 1310.

Notably, in at least one embodiment and referring to FIG. 23B, the port portion 1310a may also be connected to extendable sleeves 1340 and 1350. Accordingly, removing the port portion 1310a from the conduit portion 1310b may enable a user to also pull sleeves 1340, 1350 from the patient during a surgical procedure.

Similar to that described above with respect to transorifice device 300, referring to FIG. 23D, each of the ports 1311, 1312, 1313 may be a different size. For example, in at least one embodiment, port 1311 may accommodate a 10 mm or smaller diameter tool, port 1312 may accommodate a 5 mm or smaller diameter tool, and port 1313 may accommodate an 18 mm or smaller diameter tool. Further, each port 1311, 1312, 1313 may include one or more seals as described above with respect to transorifice device 300.

Further, similar to transorifice device 300, the flexible conduit 1320 may also comprise a flexible, resilient, or pliable ring 1323 located at the distal portion 1322 of the conduit 1320. Additionally, the flexible conduit 1320 may also comprise a suture 1324 connected to the pliable ring 1323 and/or to the distal portion 1322 of the conduit 1320. The pliable ring 1323 may be configured such that when it is not under external force, the ring 1323 assumes the shape shown in FIG. 23A, causing the distal portion 1322 of the flexible conduit 1320 to flare outward. In other words, the pliable ring 1323 may be biased toward an annular or open shape. However, the pliable ring 1323 may be bent into a folded shape, such as a hyperbolic paraboloid, by the application of an external force. Such external force may come from a user pulling on suture 1324.

However, in at least one embodiment referring now to FIG. 22A and as mentioned above, a suture holder, such as suture holder 1240 of surgical delivery device 1200, may releasably hold suture 1324. Accordingly, after attaching the suture 1324 to suture holder 1240, the pliable ring 1323 may be pulled in a distal direction, toward tip 1220 of the surgical delivery device 1200, such that the pliable ring 1323 collapses, buckles, or otherwise bends into a compact or folded shape. The folded shape of ring 1323 may allow the ring 1323, and hence, the distal portion 1322 of the flexible conduit 1320 to move through a smaller opening, such as incision 14 (see FIG. 10), than the ring 1323 would fit through if the ring were in an unfolded, annular shape. Additionally, the suture 1324 may be of a varying length. For example, in one embodiment, although not shown, the suture 1324 may be relatively shorter than illustrated in FIG. 22A such that the pliable ring 1323 and/or the transorifice device's distal portion 1322 to be close to and/or tangential to suture holder 1240.

Focusing now on the support member 1330, in various embodiments, the support member 1330 may be configured to provide support for the port assembly 1310 and/or the flexible conduit 1320 after the transorifice device 1300 is positioned at least partially within a speculum, such as speculum 2100, see FIGS. 13A-13B. For example, FIG. 23E shows a side perspective view of the transorifice device 1300 supported by the speculum 2100 with the flexible conduit 1320 positioned between the speculum blades 2120, 2130, 2140 (in FIG. 23E, a view of blade 2140 is obstructed by the conduit 1320). Further, in various embodiments, similar to that described above with respect to transorifice device 300, the support member 1330 may comprise an expandable bladder 1332 that is expandable or inflatable between an unexpanded and an expanded configuration. For example, FIG. 23A shows the expandable bladder 1332 in an unexpanded configuration and FIG. 23E shows the expandable bladder 1332 in an expanded configuration. The bladder 1332 may be expanded via port 1331. Port 1331 may comprise a stopcock valve and may allow gas and/or liquid to be passed through port 1331 into bladder 1332 to inflate and/or expand the same. The port 1331 may then be closed to maintain gas and/or liquid pressure within the expanded bladder 1332, see FIG. 23E. Then, after a surgical procedure is completed, the bladder 1332 may be deflated or compressed to an unexpanded configuration by opening port 1331 to release gas and/or liquid pressure.

Referring to FIG. 23E, while the transorifice device 1300 is positioned at least partially through speculum 2100, the expandable bladder 1332 may provide support to the port assembly 1310 and/or to the flexible conduit 1320 during a surgical procedure. Accordingly, the expandable bladder 1332 may be configured such that at least a portion, e.g., a proximal portion 1333, of the bladder 1330 contacts the port assembly 1310 when the bladder 1332 is expanded.

Further, similar to transorifice device 300, in at least one embodiment and as seen in FIG. 23E, the bladder 1332 may also contact at least a portion of the speculum 2100 when the bladder 1332 is expanded. In such embodiments, the bladder 1332 may serve as a flexible shock absorber and/or resilient mount between the transorifice device 1300 and the speculum 2100. The expanded bladder 1332 thus may provide support to the port assembly 1310 and/or the flexible conduit 1320 while permitting flexible maneuverability to a surgical tool inserted through the transorifice device 1300. Additionally, referring to FIGS. 23A and 23E, when expanded (as shown in FIG. 23E), the bladder 1332 may take up slack in the flexible conduit, between the distal portion 1322 and the proximal portion 1321 (see FIG. 23A). In other words, a portion of the bladder 1332 may move with respect to the distal portion 1322 of the flexible conduit 1320 such that the port assembly 1310 and/or the proximal portion 1321 of the conduit 1320 move away from the distal portion 1322 and/or pliable ring 1323, secured through incision 14 (see FIG. 11). Accordingly, the flexible conduit 1320 may be made taught by way of expanding bladder 1332, and, thus, anatomical variation between patients' vaginal lengths may be further removed as a significant surgical factor. In at least one such embodiment, the flexible conduit may be approximately five inches in length to accommodate a majority of the patient population.

Further, referring still to FIG. 23E, in at least one embodiment, the bladder 332 may have an outer diameter that is larger than the flexible conduit 320 and/or the speculum base 2110, such that the conduit 1320 may pass through the base 2110 while the bladder 1332 may contact and be supported by the proximal surface 2112 (see FIG. 13B) of the base 2110, as noted above.

In at least one embodiment, referring to FIG. 23A, the bladder 1332 may be discontinuous with the port assembly 1310; however, the flexible conduit 1320 may pass through the expandable bladder 1332. In such embodiments, the bladder 1332 may also be movable with respect to the flexible conduit 1320. In other words, the bladder 1332 may form an annular ring-like structure movably surrounding the proximal portion 1332 of the flexible conduit 1320.

The transorifice device 1300 may be further configured to provide additional protection to tissue and/or organs within a patient's body during a surgical procedure. For example, in at least one embodiment, the transorifice device 1300 may further comprise a first extendable sleeve 1340 extending from first port 1311. The extendable sleeve 1340 may be further located at least partially within the flexible conduit 1320, when the port portion 1310a is connected to the conduit portion 1310b. Further, in another embodiment, the transorifice device 1300 may further comprise a second extendable sleeve 1350 extending from the second port 1312. The second extendable sleeve 1350 may further be located at least partially within the flexible conduit 1320, when the port assembly portions 1310a, 1310b are connected to each other. As shown in FIG. 23B, the first extendable sleeve 1340 and the second extendable sleeve 1350 may be seen in retracted configurations. In at least one embodiment, one or both of flexible sleeves 1340, 1350 may be collapsed upon themselves in a random buckling or crinkled configuration such that each flexible sleeve 1340, 1350 may rest, accordion-style, in the retracted configuration seen in FIG. 23B, for instance. Alternatively, the sleeves 1340, 1350 may be pleated. Referring still to FIG. 23B, the extendable sleeves 1340, 1350 may further include at least partially rigid tubular supports 1344, 1354, respectively, that are attached to port portion 1310a and extend inside extendable sleeves 1340, 1350 for a portion of or past their lengths to provide support to the sleeves 1340, 1350 while they are in the retracted configurations as shown. In at least one embodiment, the tubular supports may be partially flexible, yet more rigid than the extendable sleeves such that the tubular supports hold the sleeves until the latter are extended, as discussed below.

Figure 23C:
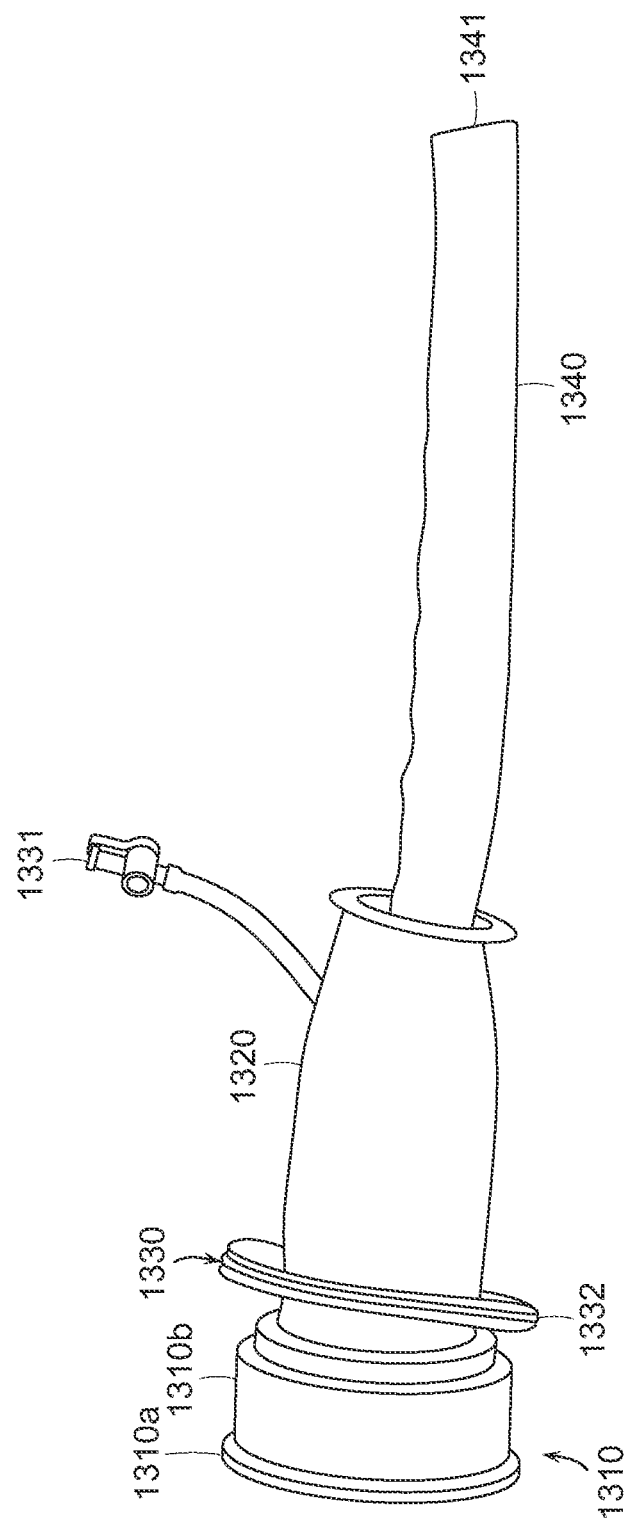
FIG. 23C is a side view of the transorifice device of FIG. 23A with an extendable sleeve extended out of a flexible conduit of the device.
Figure 23D:
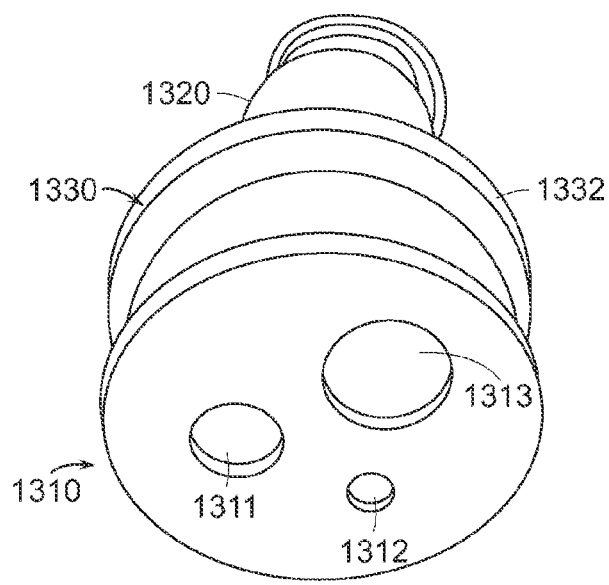
FIG. 23D is a top perspective view of the transorifice device of FIG. 23A.
Figure 23E:
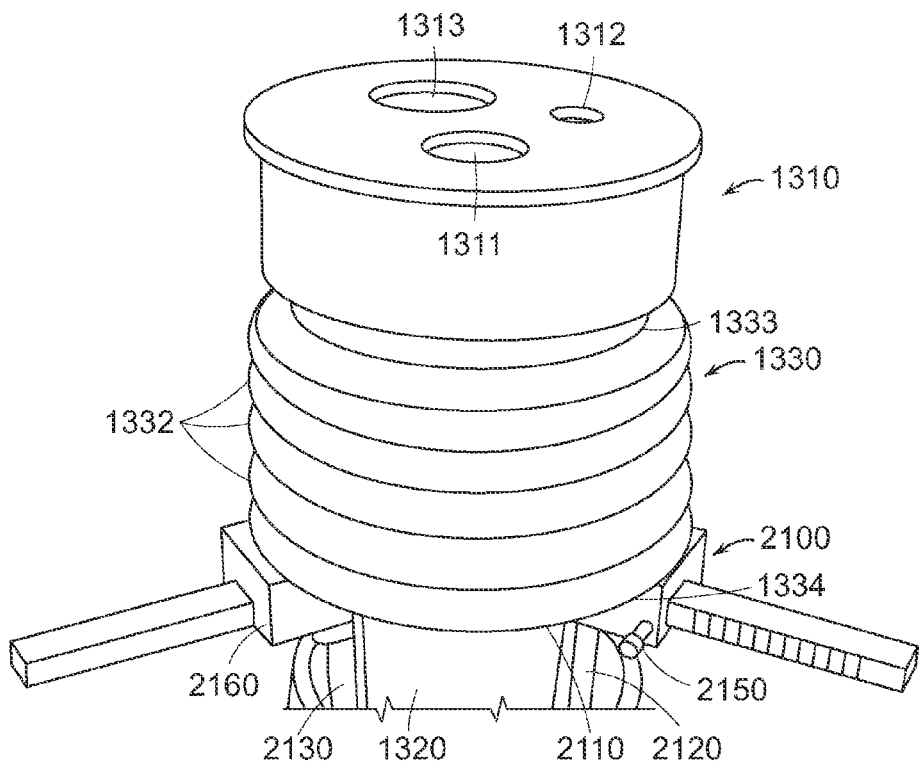
FIG. 23E is a side perspective view of the transorifice device of FIG. 23A supported by the speculum of FIG. 13A; an expandable bladder is expanded to support the port assembly of the transorifice device against the speculum; the flexible conduit of the transorifice device is shown passing between the speculum blades.

Further, in at least one embodiment, referring to FIG. 23C, one or both of extendable sleeves 1340, 1350 may be extended into an extended configuration such that first extendable sleeve 1340 and/or second extendable sleeve 1350 extends beyond the distal portion 1322 of the flexible conduit and into a body cavity. In such embodiments, the extendable sleeves 1340, 1350 may help provide further protection to internal organs and/or tissue during surgical instrument exchanges through first port 1311 and/or second port 1312. For example, as seen in FIG. 23C, the extendable sleeve 1340 has been extended into an extended configuration.

Similar to transorifice device 300, described above, in various embodiments, one or more of the extendable sleeves 1340, 1350 may include features to facilitate their extension. For example, referring to FIG. 23B, in at least one embodiment, first extendable sleeve 1340 may comprise a proximal end 1341 abutting the first port 1311 and a distal end 1342, and the second extendable sleeve 1350 may likewise comprise a proximal end 1351 abutting the second port 1312 and a distal end 1352. Further, first extendable sleeve 1340 may also include a first suture 1343 located at the distal end 1342 of sleeve 1340 and/or the second extendable sleeve may include a second suture 1353 located at the distal end 1352 of sleeve 1350. Thus, the extendable sleeves 1340, 1350 may be extended similar to that described above with respect to transorifice device 300 and as illustrated in FIG. 11. When the sleeves are in the retracted configurations, as seen in FIG. 23B, for example, the sutures may also be positioned and/or releasably held in slits 1345, 1355 formed in the tubular supports 1344, 1354 mentioned above, thereby assisting a user to locate the suture with a grasper by maintaining the position of the sutures near the center of each tubular support, prior to extension.

Figure 24:
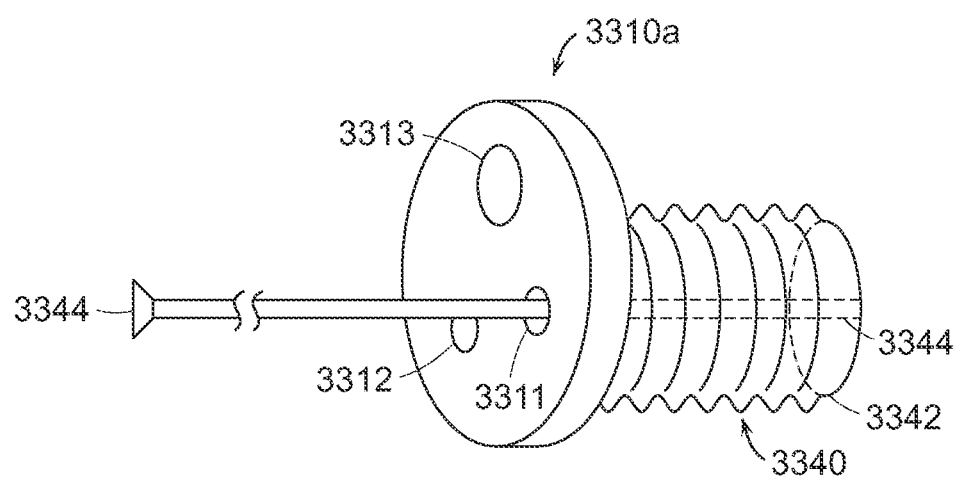
FIG. 24 is a side perspective view of a port assembly's port portion of a transorifice device with an extendable sleeve extending from the port portion according to a non-limiting embodiment.

Varying options are discussed above to allow a user to extend the extendable sleeves of a transorifice device. However, additional options are possible to achieve the same or similar result. For example, in at least one embodiment and referring to FIG. 24, an extension rod or tab, such as extension tab 3344 may be included in a transorifice device comprising a port assembly including a port portion 3310a. Port portion 3310a may be similar to port portion 1310a discussed above in reference to transorifice device 1300. For example, an extendable sleeve 3340 may extend from the first port 3311. While not shown, each of the other ports, e.g., second port 3312 and/or third port 3313, may also be associated with an extendable sleeve extending therefrom. In any event, as shown in FIG. 24, the extendable sleeve 3340 may be in an accordion-like, retracted configuration. To facilitate extension of sleeve 3340, the tab 3344 may be attached to the sleeve 3340 at or near the sleeve's distal end 3340. Further, the tab 3344 may be sized and configured that, when the sleeve is in a retracted configuration as shown, the tab 3344 also extends through the sleeve 3340 and out of port 3311 in a proximal direction. Thus, when the port portion 3310a is in place with a conduit portion (not shown, see however, conduit portion 1310a in FIG. 23B, for example), or otherwise in position during a surgical procedure, the extendable sleeve 3340 may be extended when a user presses on the tab 3344 such that the sleeve's distal end 3342 extends in a distal direction (to the right of FIG. 24). The tab 3344 may be configured such that it rests on a lip or in a pocket (not shown) at distal end 3342 and thus may only apply a force to the sleeve 3340 in a distal direction. Moving the tab 3344 in a proximal direction may thus disconnect or otherwise release the tab 3344 from the sleeve's distal end 3342. In such embodiments, the tab 3344 may be removed from the sleeve 3340, after extending sleeve 3340, by pulling the tab 3344 in a proximal direction, and out through port 3311. Further, the tab 3344 may be rigid or at least partially rigid such that it does not significantly buckle when applying a force to the sleeve's distal end 3342.

Figure 25:
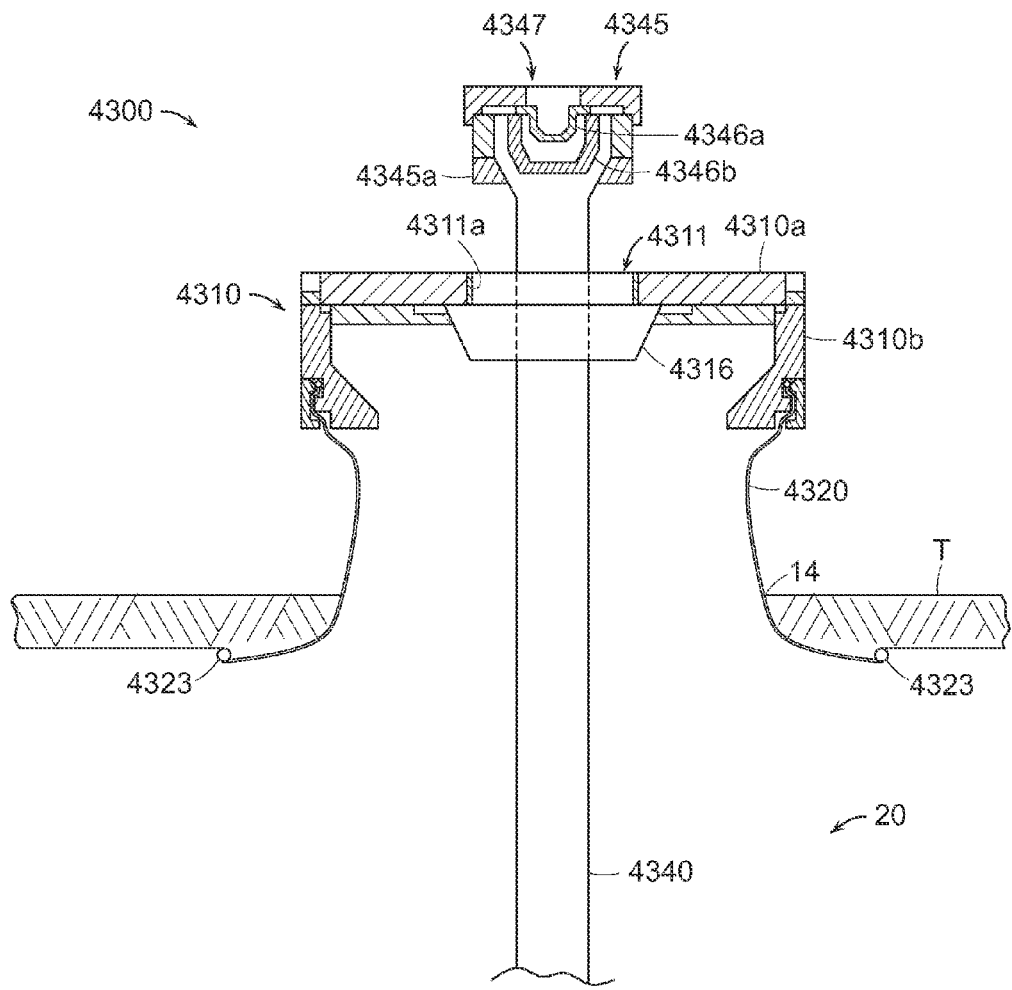
FIG. 25 is a side cross-sectional view of a transorifice device according to a non-limiting embodiment, after the transorifice device has been placed through an incision in a patient's tissue.

Another exemplary embodiment of a transorifice device 4300 including a sleeve 4340 is shown in FIG. 25. FIG. 25 shows a side cross-sectional view of transorifice device 4300 after the device 4300 has been placed through an incision 14 in tissue T. Transorifice device 4300 may be similar to transorifice device 300, described above. The transorifice device 4300 may include a port assembly 4310 defining at least one port, e.g., port 4311, and a flexible conduit 4320 including a distal pliable ring 4323 configured to seal the flexible conduit against tissue T through an incision 14. As noted above with respect to transorifice device 1300, the port assembly 4310 may comprise a port portion 4310a and a conduit portion 1310b that are detachable from each other. Further, the port 4311 or a portion of it may be detached from port portion 4310a. For example, the port 4311 may releasably receive a seal assembly 4345. Seal assembly 4345 may be attached to sleeve 4340. Further, seal assembly may include a luer-like taper 4345a that is configured to releasably engage and/or lock with a luer-like taper 4311a formed in port 4311. Alternatively, the seal assembly 4345 and/or port 4311 may include other interconnective seals or mating arrangements, such as compressive O-rings, gaskets, compressive rubber, and polymers, for example. In any event, the seal assembly 4345 may be attached and detached from port portion 4310a such that gas pressure (for insufflation purposes, for example) may be maintained after connecting the seal assembly 4345 to the port 4311.

Further, referring still to FIG. 25, the port 4311 may further include at least one seal 4316, which may be similar to at least one of the seals described above with respect to transorifice device 300. In at least one embodiment, the seal 4316 may be sized and configured to allow any size instrument shaft from 2-30 mm to pass therethrough. Additionally, the seal 4316 may be sized and configured to allow sleeve 4340 to pass therethrough. For example, in at least one embodiment, the sleeve 4340 may be at least partially rigid owing to a wire, for example, running along its length. Accordingly, after positioning the pliable ring 4323 distal to incision 14 and/or tissue T, the sleeve 4340 may be advanced through the port 4311, through the flexible conduit 4320, past ring 4323, and into body cavity 20, for example. Accordingly a protected pathway for surgical tools through an opening 4347 defined by seal assembly 4345 and sleeve 4340 into cavity 20 may be provided during a surgical procedure. Sleeve 4340 may provide similar other advantages to that described above with respect to transorifice device 300.

Additionally, the seal assembly 4345 may further comprise at least one seal. In at least one embodiment, the seal assembly 4345 may further comprise a first seal 4346a and a second seal 4346b. The first seal 4346a may be a duckbill seal and the second seal 4346b may be a lip seal, or vice versa. A duckbill seal may help maintain pressure for insufflation, while the lip seal may accommodate varying sizes of surgical tools while keeping an edge of the seal flush with a surface of a surgical tool for sterility maintenance, for example.

The seal or seals mentioned herein in respect to any of the surgical system components, such as a transorifice device, may be substituted for various other seals known in the field. For example, each seal may include one or more of the following: a duckbill seal; a lip seal, an S-shaped seal, a foam seal, a gel seal, and a pierceable membrane. Alternatively, the seal(s) may be omitted entirely from the devices described herein.

Various embodiments are also envisioned for a support member associated with a transorifice device. For example, a support member may comprise an expandable bladder 332 or 1332, as describe above with respect to transorifice devices 300 and 1300, respectively. The expandable bladder may provide various advantages, such as assisting in taking up slack left in a flexible conduit 320, 1320, after the conduit has been at least partially inserted through an incision 14 and/or a pliable ring 323, 1323 has been positioned distal to the incision 14 (see FIG. 11, for example). Other support members are envisioned which may also provide similar such advantages to a transorifice device. For example, referring now to FIG. 26A, a side cross-sectional view is provided of a transorifice device 5300 resting on a speculum 5100 after the speculum has been inserted into an orifice to expand tissue walls 11, an incision 14 has been made in the tissue T, and a pliable ring 5323 of the transorifice device has been positioned distal to incision 14. As illustrated in FIG. 26A, only a portion of each device 5300, 10100 is shown, to the left of centerline C. The transorifice device 5300 may be similar to transorifice device 4300, described above. For example, the transorifice device may include a port assembly 5310 defining at least one port, e.g., port 5311, and a flexible conduit 5320 including a distal pliable ring 5323 configured to seal the flexible conduit against tissue T through the incision 14. As noted above with respect to transorifice device 4300, the port assembly 5310 may comprise a port portion 5310a and a conduit portion 5310b that are detachable from each other.

Similar to transorifice device 300, the port assembly 5310 may include a proximal side 5314 and a distal side 5315. Further, the flexible conduit 5320 may extend from the port assembly's distal side 5314 and the conduit 5320 may include a distal portion 5322. Additionally, the transorifice device 5300 may comprise at least one support member 5330 movable with respect to the distal portion 5322 of the flexible conduit and extendable to the port assembly's distal side 5315.

However, transorifice device 5300 may differ from transorifice device 300 in that the support member 5330 may comprise a rotatable push member 5331. Referring briefly to FIG. 26B, which shows a top view of the push member 5331 and a portion of the port assembly 5310, the push member 5331 is configured to rotate between a locked position (shown in solid lines), and an unlocked, pushable position (shown in dotted lines). Referring to FIGS. 26A-26B, when the push member 5331 is rotated to the pushable position, the push member 5331 may be moved or pushed in a distal direction (toward the bottom of FIG. 26A) such that the push member 5331 may contact the speculum's proximal surface 10112 and thus may lift the port assembly 5310 to subsequently take up slack in the flexible conduit 5320, between the port assembly 5310 and the pliable ring 5322, which is secured beyond the incision 14 in tissue T.

Figure 26C:
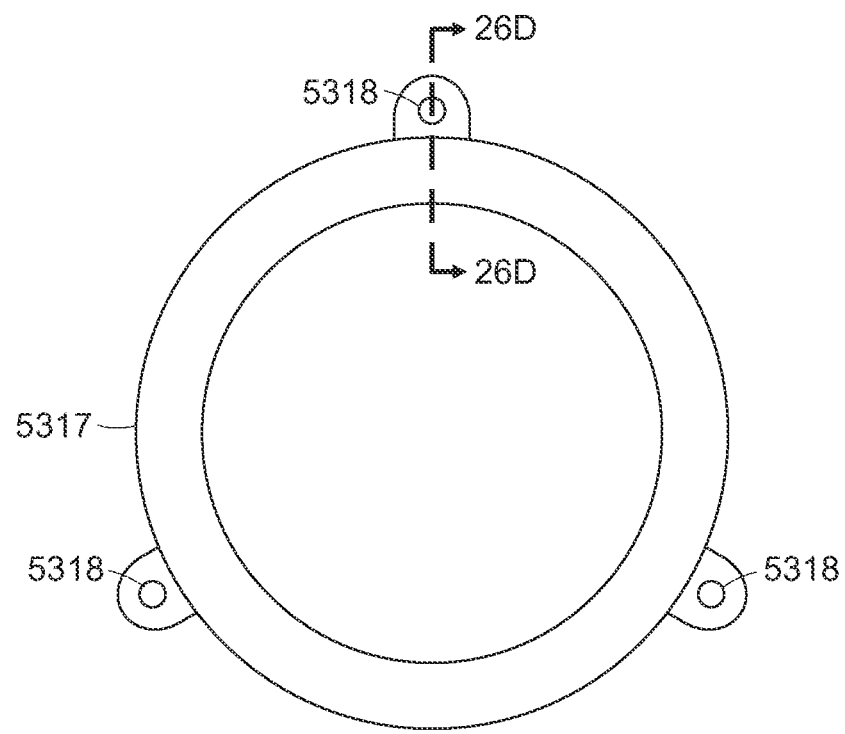
FIG. 26C is a top view of a support ring of the transorifice device of FIG. 26A.
Figure 26D:
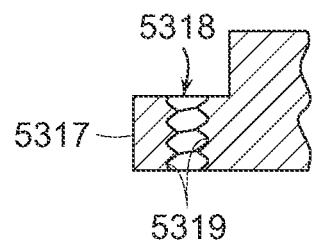
FIG. 26D is a partial cross-sectional view of the support ring of FIG. 26C, taken along line 26D-26D.

In more detail, referring to FIG. 26A, the push member 5331 may include an insertable portion 5334 sized and configured to be received in a locking hole 5318 of the port assembly 5310. The locking hole 5318 may be better seen in FIGS. 26C-26D. FIG. 26C is a top view of a support ring 5317. FIG. 26D shows a partial cross-sectional view of the support ring 5317, taken along line 26D-26D, showing a detail of the locking hole 5318 defined by support ring 5317. Support ring 5317 may be a part of the port assembly's conduit portion 5310b and may be coupled to flexible conduit 5320 and/or releasably attached to port portion 5310a. Briefly, referring to FIG. 26A, part of the conduit's proximal portion 5321 may be sandwich in a serpentine path between components of port portion 2310b, including support ring 5317. Further, the support ring may include a groove and/or O-ring to releasably attach to port portion 5310a such that the port portion 5310a may releasably connect thereto, yet rotate, if desired, 360 degrees about the centerline C.

Moving back to the push member 5331, the push member's insertable portion 5334 may include at least one threaded side 5332 and at least one non-threaded side (not shown). The threaded side(s) 5332 may be the sides to the left and/or right of the insertable portion 5334 as illustrated in FIG. 26A. The non-threaded side(s) may be the sides of the insertable portion 5334 that are parallel to the plane of FIG. 26A. Accordingly, the push member's threaded sides 5332 may be configured to engage the locking hole's threads 5319 when the push member is rotated within the hole 5318 to the locked position. Further, the push member's non-threaded sides may be configured to align with the threads 5319 of the locking hole 5318 when the push member 5331 is rotated therein to the pushable position. Alternatively, the push member may be constructed of a rigid material, such as steel, and the locking hole may be made of a softer material, a plastic, for example, such that the push member may be self tapping within the hole and not require perfect alignment therein.

Further, the locking hole 5318 may include threads 5319 on sides of the hole 5318 that correlate with the threaded sides 5332 of the insertable portion 5334. Further, the sides of the hole that are parallel to the plane of FIG. 26A may, similar to insertable portion 5334, be non-threaded (not shown). Accordingly, the locking hole 5318 may comprise at least one threaded side 5319 and at least one non-threaded side (not shown). The locking hole's threaded sides 5319 may thus be configured to engage the push member's threaded sides when the push member is in the locked position. Further, the hole's non-threaded sides may be configured to align with the push member's non-threaded sides when the push member is in the pushable position. Thus, when the push member 5331 is in the locked position (shown in solid lines in FIG. 26B), the push member 5331 may not readily translate with respect to hole 5318 and/or port assembly 5310. However, when the push member 5331 is rotated to the unlocked, pushable position (shown in dotted lines in FIG. 26B), the push member 5331 may translate in a proximal or distal direction with respect to hole 5318, port assembly 5310, and/or distal portion 5322 of the flexible conduit 5322.

Additionally, in various embodiments, the push member 5331 may be configured to be operable by a user while resisting freely falling out of the locking hole 5318. Accordingly, in at least one embodiment and referring to FIG. 26A, the push member 5331 further comprises a proximal end 5331a, which may be adjacent to the insertable portion 5334. The proximal end 5331a may be configured to be operated by a user. In one such embodiment, the proximal end 5331a may include a finger operable tab projecting away from the insertable portion 5334. Further, the push member 5331 may also comprise a distal end 5331b, which may be adjacent to the insertable portion 5334 and opposite the proximal end 5331a. The distal end 5331b may further comprise threads 5333 that may be aligned with, or on the same side as, the non-threaded portion (not shown, see discussion above) of the insertable portion 5334. Thus, when the push member 5331 is in a translatable or pushable position (see the dotted lines in FIG. 26B), the push member's distal threads 5333 may contact the hole's threads 5319 (see FIG. 26D) if the push member 5331 is moved sufficiently in a proximal direction (towards the top of FIG. 26A), thereby preventing the push member 5331 from freely falling or moving out of the locking hole 5318.

While the above has discussed one push member 5331, it is contemplated that more than one push member 5331 may be associated with port assembly 5310 and/or flexible conduit 5320. Accordingly, in at least one embodiment and referring to FIGS. 26A and 26C, the transorifice device 5300 may further comprise at least three push members 5331, spaced evenly about support ring 5317, thereby providing an even distribution of support members 5330 about port assembly 5310 and/or conduit 5320. While three push members define a plane, more or less push members may be used if desired. Each of the push members 5331 may be similar to that described above and each may also be received within a respective locking hole 5318, which also may be similar to that described above.

Figure 27B:
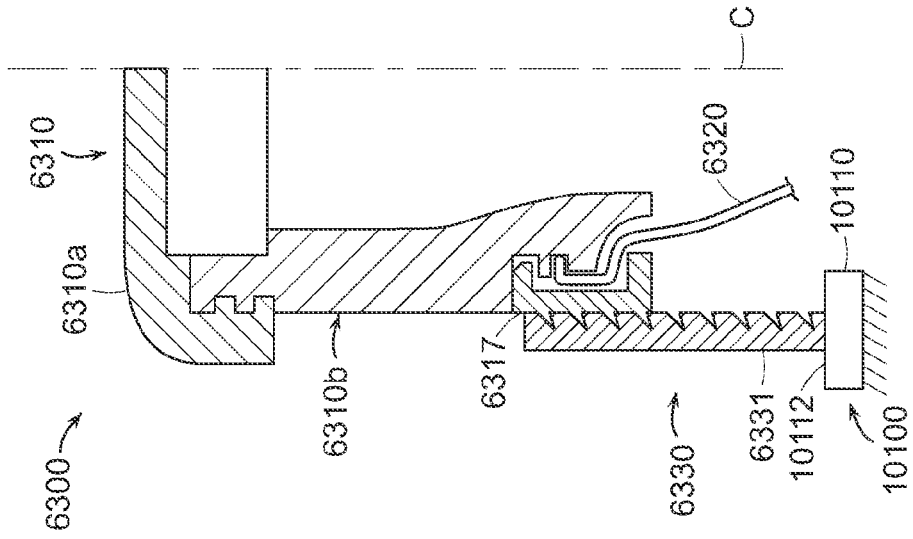
FIG. 27B is a side cross-sectional view of the portion of the transorifice device of FIG. 29A with a support member extended into contact with a speculum.
Figure 27A:
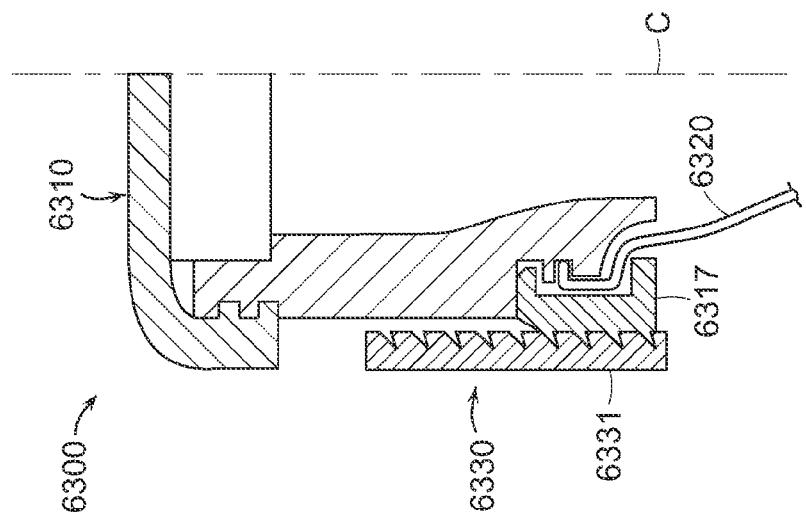
FIG. 27A is a side cross-section view of a portion of a transorifice device according to a non-limiting embodiment.

FIGS. 27A-27B illustrate another embodiment of an exemplary support member 6330 associate with a transorifice device 6330. As illustrated, only cross-sectional portions of port assembly 6310, flexible conduit 6320, and support member 6330 are shown. Transorifice device 6330 may be similar to transorifice device 5300 described above. However, in at least one embodiment, the support member 6330 may comprise a ratcheted sleeve 6331 operably engaged with the port assembly 6310. In more detail, the ratcheted sleeve 6331 may include teeth that engage teeth formed in a support ring 6317. The teeth of the support ring 6317 may be flexible such that the teeth may deflect as the sleeve 6331 is advanced in a distal direction (toward the bottom of FIG. 27A). Thus, the sleeve 6331 may be in a proximal position as shown in FIG. 27A, then after the transorifice device 6300 is positioned in a surgical site and/or within a speculum 10100, as described above, the sleeve 6331 may be moved in a distal direction, in a ratchet-like fashion, toward speculum 10100 until the sleeve 6331 contacts the proximal surface 10112 of speculum base 10110, for example. As shown in FIG. 27B, the sleeve 6331 may thereby be moved to a distal position to take up slack in conduit 6320. In at least one embodiment, the sleeve 6331 may be annular and/or surround all of support ring 6317. Alternatively, multiple sleeves 6331 may be spaced about support ring 6317. Additionally, the sleeve and/or ring may be threaded such that the sleeve may be moved proximally and/or distally by rotating the sleeve with respect to the ring. Further, the sleeve may be constructed of multiple telescoping segments such that additional extension may be achieved, if desired.

Further, as shown in FIG. 27B, the port assembly 6310 may include port portion 6310*a* that is detachable from conduit portion 6310*b*. The port portion 6310*a* may be screwed on to conduit portion 6310*b*. Accordingly, the port portion 6310*a* may be removed from the conduit portion 6310*b* by unscrewing the former from the later or vice versa.

Additionally, although not shown, a support member may comprise a spring between the port portion and the conduit portion of a port assembly. Alternatively, or additionally, a spring may extend distally beyond the port assembly to engage a speculum, for example, thereby providing the port assembly with the ability to deflect during a surgical procedure, if desired.

Figure 28A:
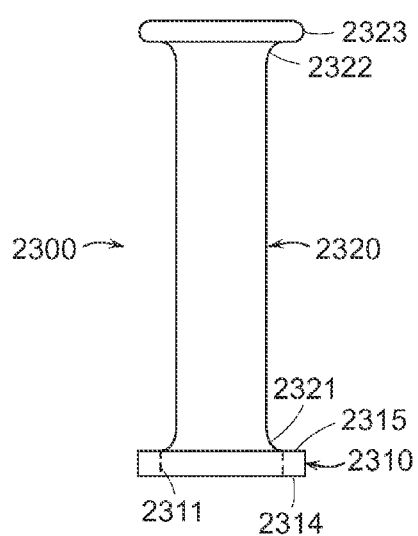
FIG. 28A is a side view of a transorifice device according to a non-limiting embodiment.

Another embodiment of an exemplary transorifice device, transorifice device 2300, is illustrated in FIG. 28A, which shows a side view of the transorifice device 2300. Transorifice device 2300 may be similar to transorifice device 300. For instance, the transorifice device 2300 may comprise a port assembly 2310 defining at least one port 2311 therein. In FIG. 28A, the walls of the port 2311 within port assembly 2310 are shown in dotted lines. The port assembly 2310 may also likewise include a proximal side 2314 and a distal side 2315. The transorifice device 2300 may further include a flexible conduit 2320 extending from the distal side 2315 of the port assembly 2310 and the flexible conduit may also include a proximal portion 2321 adjacent to the port assembly 2310, a distal portion 2322, and a pliable ring 2323 located at the distal portion 2322. The pliable ring 2323 may be configured such that when it is not under external force, the ring 2323 may assume the shape shown in FIG. 28A, thereby causing the distal portion 2322 of the flexible conduit 2320 to flare outward. In other words, the pliable ring 2323 may be biased toward an annular or open shape. However, the pliable ring 2323 may be bent into a folded shape, such as a hyperbolic paraboloid, by the application of an external force. Such external force may come from a user bending the ring with their fingers, for example.

Notably different from transorifice device 300, in at least one embodiment, transorifice device 2300 may not include a support member that may be positioned between the port assembly 2310 and a speculum, when the transorifice device 2300 is inserted at least partially through a speculum. However, in various alternative embodiments, a support member or members, as described herein, may be added to the transorifice device 2300, if desired.

In any event, similar to transorifice device 300, the transorifice device 2300, once properly positioned within a patient (discussed below), may be configured to provide a sealed passageway, through flexible conduit 2320, from outside a patient's body to body cavity. The pliable ring 2323, which may be positioned distal to an incision during a surgical procedure, may also prevent inadvertent removal or dislodgment of the distal portion 2322 from a patient's body, thereby retaining the transorifice device 2300 within the patient during a surgical procedure.

Figure 28B:
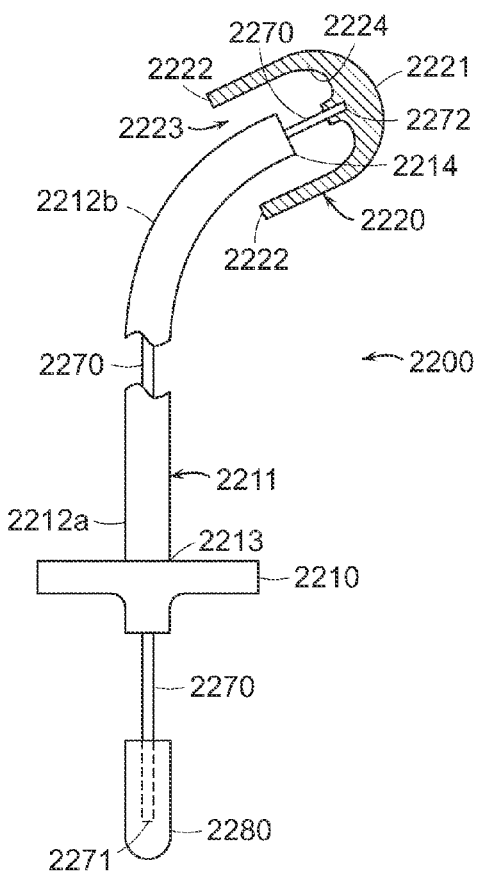
FIG. 28B is a side view of a surgical delivery device according to a non-limiting embodiment; part of a body of the device is shown cut-away and a tip of the device is shown cross-sectioned.

Moving now to FIG. 28B, another embodiment of an exemplary surgical delivery device, surgical delivery device 2200, is shown. FIG. 28B illustrates a side view of the delivery device 2200. Surgical delivery device 2200 may be similar to delivery device 200, described above, in that surgical delivery device 2200 may be configured to assist in the proper placement and/or sealing of a transorifice device, such as transorifice device 2300 (see FIG. 28A, discussed above) within a body cavity. For example and referring to FIG. 28B, in various embodiments, the surgical delivery device 2200 may comprise a foundation 2210, a shaft 2270, and a tip 220. The shaft 2270 may include a proximal end 2271 and a distal end 2272 and the shaft 2270 may also extend through the foundation 2210 such that the shaft 2270 is movable with respect to the foundation 2210. In other words, there may be a hole (not shown) defined by the foundation that slidably engages shaft 2270 therethrough such that the shaft 2270 may be slid or otherwise moved back and forth in a distal direction (toward the top of FIG. 28B) or a proximal direction (toward the bottom of FIG. 28B) through the foundation 2210.

Further, in various embodiments, the delivery device's tip 2220 may be mounted to the distal end 2272 of the shaft 2270 such that movement of the shaft's proximal end 2271 effectuates movement of the tip 2220 relative to the foundation 2210. The tip 2220 may include a distal side 2221 and a proximal side 2222, wherein the proximal side 2222 defines an opening 2223 sized and configured to receive at least a portion of a surgical tool. For example, in at least one embodiment and as discussed in more detail below, the opening 2223 may be sized and configured to receive the pliable ring 2323 of transorifice device 2300, see FIGS. 28A and 28C.

In at least one embodiment, referring back to FIG. 28B, the surgical delivery device 2200 may further comprise a body 2211 extending from the foundation 2210. Further, the body 2211 may be rigid. In such embodiments, the shaft 2270 may extend through the rigid body 2211. For example, the body 2211 may define a lumen (not shown) through which the shaft 2270 may slidably pass. The rigid body 2211 may define a path and/or provide support for the shaft 2270 when the shaft 2270 is moved back and forth, as noted above. Further, in at least one embodiment, the shaft 2270 may be made from a flexible material.

In various embodiments, the rigid body 2211 may also define at least one curve corresponding to the shaft. For instance, the rigid body 2211 may include a straight, linear portion 2212*a* located adjacent to the foundation 2210 and a curved, non-linear portion 2212*b* located distal to straight portion 2212 and/or adjacent to the tip 2220. Referring now to FIG. 28B and FIG. 6B, similar to that discussed above with respect to surgical delivery device 200, surgical delivery device 2200 may be inserted at an incision ultimately made at an otomy site 13 located in a patient's vagina 10, for example. The curved portion 2212b may enable the user to insert the tip 2200 through the incision and into a body cavity at a desired angle, e.g., between the rectum and the uterus in the rectouterine pouch.

Figure 28C:
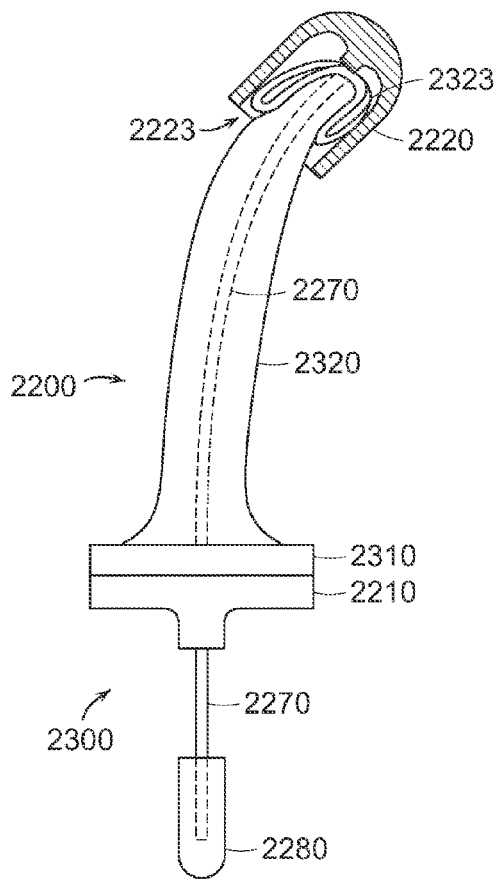
FIG. 28C is a side view of the transorifice device of FIG. 28A mounted to the surgical delivery device of FIG. 28B; a pliable ring of the transorifice device is received in the tip of the surgical delivery device.
Figure 28D:
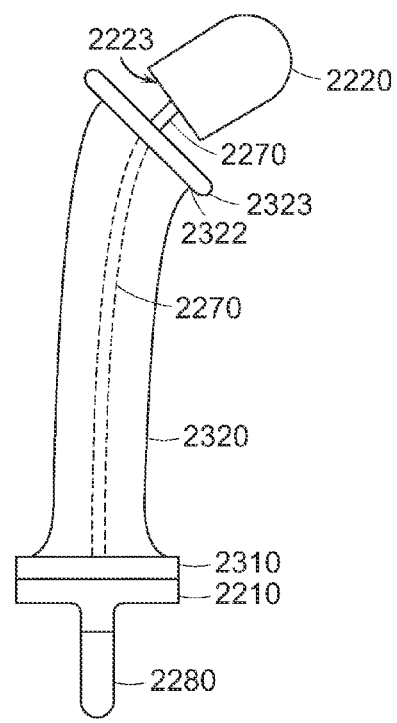
FIG. 28D is a side view of the transorifice device and the surgical delivery device of FIG. 28C after the tip of the surgical delivery device has been moved distally to release the pliable ring of the transorifice device.

Additionally, the surgical delivery device 2200, in at least one embodiment, may further comprise a handle 2280 attached to the proximal end 2271 of the shaft 2270. For example, the handle 2280 may be formed on or otherwise fixedly connected to the shaft's proximal end 2280. The handle 2280 may be configured for a user to grasp the handle 2280 and thereby move the shaft 2270 and, subsequently, the tip 2220 in a proximal or distal direction. For example, referring to FIGS. 28C-28D, a user may move the handle 2280 from a proximal position shown in FIG. 28C to a distal position shown in FIG. 28D, thereby also moving the tip 2220 from a proximal position (FIG. 28C) to a distal position (FIG. 28D). The tip 2220 and handle 2280 are also shown in a proximal position in FIG. 28B.

Further, in at least one embodiment, the handle 2280, the body 2211, and the shaft 2270 may cooperate to enable the tip 2220 to be moved a limited distance. In such embodiments, the body 2211 may also comprise a proximal end 2213 adjacent to the foundation 2210 and a distal end 2214. Also, the distance between the handle and the tip may be greater than the distance between the foundation and the distal end of the rigid body. Thus, referring still to FIG. 28B, the shaft 2270 may move in a distal direction (toward the top of FIG. 28B) until the handle contacts the foundation 2210. The handle 2280 may not pass through the foundation 2210 because the handle 2280 may be larger in diameter than shaft 2280 and/or the handle 2280 may be also larger than the foundation hole (not shown) through which the shaft 2270 passes. In more detail, for example, as seen in FIG. 28C, the shaft 2270 may extend a distance proximally beyond the foundation 2210, toward handle 2280. Moving the handle 2280 into contact with the foundation 2210, as seen in FIG. 28D, causes the tip 2220 to also move the distance that shaft 2270 was exposed beyond foundation 2210 in FIG. 28C. Accordingly, the tip 2220 may be moved a limited distance, as defined by the amount of shaft 2270 exposed proximally beyond foundation 2210 when the handle 2280 and/or tip 2220 are in a proximal position, see, again, FIG. 28C.

Additionally, the body 2211 may limit how far the tip 2220 may move in a proximal direction. In at least one embodiment, moving the handle 2280 in a proximal direction, e.g., toward the bottom of FIG. 28B, may cause the tip 2220 to contact body 2211. The tip 2220 may be larger than the body 2211, and thus, may not pass therethrough. Accordingly, the tip 2220 may be limited to moving from a proximal position where the tip 2220 contacts the body 2211 to a distal position, such as that shown in FIG. 28D, where the handle 2280 contacts the foundation 2210.

In various embodiments, and as illustrated in FIG. 28B, the tip 2220 may be blunt. For example, the tip 2220, as shown in FIG. 28B, may be curved or parabolic in shape. In such embodiments, the surgical delivery device 2220 may not, itself, make an incision at an otomy site 13, see FIG. 6B. Therefore, where the tip 2220 is blunt, another tool, such as surgical delivery device 200, a scalpel, needle, or other incision-making device may be used to create an incision in the patient's tissue. Thereafter, the tip 2220 may be advanced through the incision. Further, owing to the curved shape of the tip 2220, the tip 2220 may dilate or expand the incision as the tip 2220 is advanced therethrough.

As mentioned above, the surgical delivery device 2200 may be configured to deliver a portion of a surgical device to a patient's body cavity. In various embodiments, the surgical delivery device 2200 may be configured to deliver a transorifice device, such as transorifice device 2300. In more detail, referring now to FIGS. 28C-28D, the transorifice device 2300 may first be mounted to the surgical delivery device 2200. In at least one embodiment, the delivery device's tip 2200 may be passed through the transorifice device's flexible conduit 2320. Further, the transorifice device's port assembly 2310 may be brought into contact with and/or releasably connected to the delivery device's foundation 2210. For example, the foundation 2310 and/or the port assembly 2310 may include snap-fit features, screws, tabs, or other mechanisms to releasably connect the two components together.

As shown in FIG. 28C, after passing the tip 220 through the flexible conduit 2320, the transorifice device's pliable ring 2323 may be folded or otherwise compacted to fit within the tip's opening 2223 such that the pliable ring 2323 may be held or biased against an inner wall 2224 of tip 2220 (see FIG. 28B). To aid in later deployment of the ring 2323 from the tip 2220, medical lubricants may be added to either inner wall 2224 and/or to ring 2323 before inserting the ring 2323 into tip 2220.

Next, the coupled transorifice device 2300 and surgical delivery device 2200 may be at least partially inserted into a patient as described above with respect to transorifice device 300 and delivery device 200, see FIGS. 8-11, for example. Notably, if the tip 2220 is blunt, then the incision 14 (see FIG. 9A) may be made before inserting the coupled devices into the patient, as discussed above. If another device is used to make the incision 14, then a guidewire may be placed into the incision during its creation, e.g., where an endoscope is used to assist in the creation of the incision 14, the guide wire may be placed through a working channel of an endoscope. The guidewire may assist a user in placing the tip 2220 of the surgical deliver device 2200 through the incision 14. In any event, referring to FIG. 28C and FIG. 9A, the tip 2220 may ultimately be passed through incision 14 such that the tip 2220 is located within body cavity 20.

After inserting the tip 2220 into body cavity 20, the handle 2280 may be advanced in a distal direction to a distal position, such as that shown in FIG. 28D. As discussed above, moving the handle 2280 as such may cause the tip 2220 to also move to a distal position. However, because the port assembly 2310 may be connected to the foundation 2210, the pliable ring 2323 may not move as far as the tip 2220. Accordingly, the pliable ring 2323 may be thereby released from the tip 2220 through opening 2223, thereby causing the ring 2323 and the distal portion 2322 of flexible conduit 2320 to flare outward, away from tip 2220 and/or shaft 2270. The transorifice device 2300 may now be in a similar configuration to that shown in FIG. 10 with respect to transorifice device 2300, forming a sealed conduit from outside the patient's body to body cavity 20 through the patient's vagina, for example.

Next, the surgical delivery device 2200 may be removed from the patient. First, the foundation 2210 may be detached from the port assembly 2310. Then, the delivery device 2200 may be pulled in a proximal direction such that the tip 2220 is pulled through the flexible conduit 2320 and out port assembly 2310. In such embodiments, the outer diameter of the tip 2220 may thereby be smaller than the inner diameter of the flexible conduit 2320 and/or a port defined within port assembly 2310.

After removing the surgical delivery device 2200 from the transorifice device 2300, a surgical procedure may be performed through the transorifice device, as described above with respect to transorifice device 300 and FIG. 11, for example.

Figure 29A:
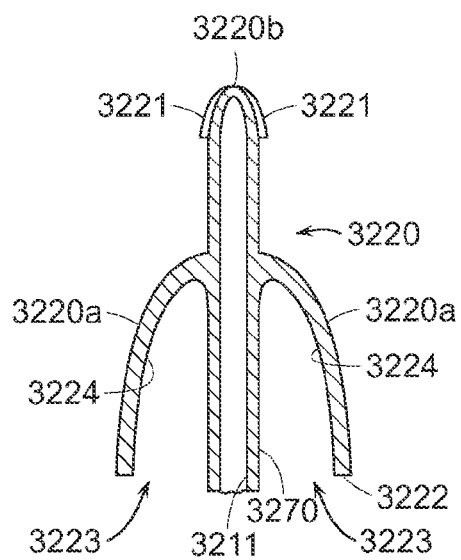
FIG. 29A is a side cross-sectional view of a tip located at a distal portion of a shaft of a surgical delivery device according to a non-limiting embodiment.

As noted above, the transorifice device's tip 2220 may be blunt. Alternatively, in various embodiments, the tip 2220 may be at least partially sharp and/or otherwise configured to make an incision in a patient's tissue, such as at otomy site 13, see FIG. 6B. In such embodiments, the tip 2220 may be similar to that described above with respect to tip 220 of delivery device 200. Further, another example of a tip configured to incise tissue, tip 3220, is shown in FIG. 29A. FIG. 29A illustrates a side cross-sectional view of tip 3220 located at a distal portion of shaft 3270. Tip 3220 and/or shaft 3270 may be substituted for tip 2220 on transorifice device 2200 shown in FIG. 28B, for example. Tip 3220 may include an incising portion 3220b extending distally from a curved portion 3220a. The incising portion 3220b may include incising wings 3221. The incising portion 3220b and/or wings 3221 may incise tissue similar as described above with respect to surgical delivery device 1200. The curved portion 3220a may function similar to that described above with respect to tip 2220 in that curved portion 3220a may include a proximal side 3222 that defines an opening 3223 sized and configured to receive at least a portion of a surgical tool. For example, in at least one embodiment, the opening 3223 may be sized and configured to receive a pliable ring of a transorifice device, such as pliable ring 2323 of transorifice device 2300, see FIG. 28A. Further, referring to FIGS. 28A and 29A, the pliable ring 2323 may be folded or otherwise compacted to fit within the tip's opening 3223 such that the pliable ring 3323 may be held or biased against an inner wall 3224 of curved portion 3220a. Accordingly, the tip 3200 may both incise tissue at an otomy site and deliver a portion of a transorifice device to a body cavity, as discussed above.

Additionally, the shaft 3270 may be similar to shaft 2270 described above. However, shaft 3270 may extend through the tip's curved portion 3220a to the incising portion 3220b. A lumen or tool receiving passageway 3211 may be defined by the inner surfaces of shaft 3270. The shaft 3270 and/or passageway 3211 may extend proximally past a foundation (not shown), similar to foundation 2210 shown in FIG. 28B and discussed above. In such embodiments, the incising portion 3220b may be at least partially transparent such that a portion of an endoscope (not shown) may be inserted into passageway 3211 until a distal end of the endoscope reaches the incising portion 3220b. In such embodiments, the endoscope may provide visual feedback or signals to a user operating a surgical delivery device including tip 3220 and/or shaft 3270 such that the user may view tissue near the incising portion 3220b during a surgical procedure.

Figure 29B:
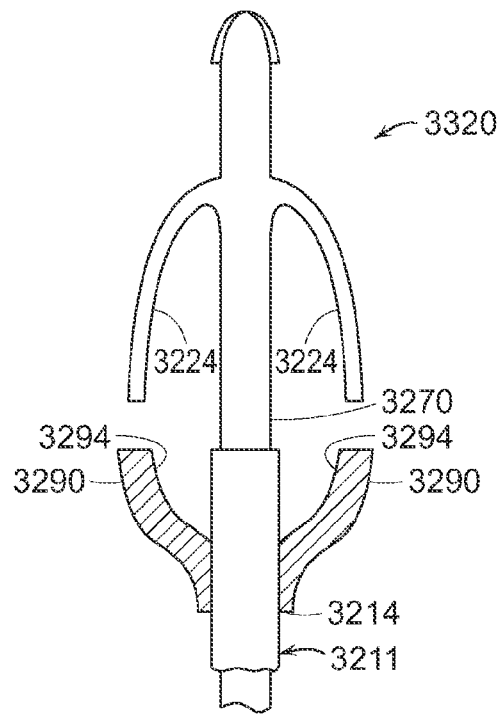
FIG. 29B is a side view of the tip and shaft of FIG. 26A extending distally from a body of the surgical delivery device with a reverse taper located at a distal end of the body, according to a non-limiting embodiment.

The tip 3220 may function as a part of a surgical delivery device to deliver a surgical device to a body cavity, as described above with respect to delivery device 2200. Additionally, tip 3220 may cooperate with other features in a surgical delivery device to assist with delivering a surgical tool (e.g., as transorifice device 2300, see FIG. 28A) to a surgical site. For example, in at least one embodiment, referring to FIG. 29B, a surgical delivery device may further include body 3211, similar to body 2211, described above. Further, the shaft 3270 may be slidably received through the body 3211. However, a reverse taper 3290 may extend from the body's distal end 3214. The taper 3290 may form a curved or parabolic shape, similar to curved portion 3220b (see FIG. 29A). The taper 3290 may serve several functions. First, when the tip 3220 is drawn into a proximal position as shown in FIG. 29B, a pliable ring, such as pliable ring 2323 (see FIG. 28A), may be folded and held between the tip's inner wall 3224 and an inner wall or walls 3294 of taper 3290. Accordingly, the walls 3224, 3294 may define a cavity to hold a pliable ring 2323, for example. In such embodiments, less of the ring 2323 may need to be inserted into tip 3220 than may be required for tip 2220, described above. Thus, because less of the ring 2323 may need to be exposed to release the ring 2323 from the tip 3220, the tip 3220 may not require as long of a distance between a proximal position and a distal position to release the pliable ring 2323. Second, the taper 3290 may allow a surgical delivery device, with which taper 3290 is a part, to center itself during removal through a flexible conduit and/or an incision. Third, owing to the shape of taper 3290, the taper 3290 may dilate or expand tissue during removal of a surgical delivery device through the incision. In this way, the tip 3220 may not snag or otherwise be restricted from moving back through the incision, after delivery of a transorifice device to a body cavity, for example.

In various embodiments, the devices may be made from various materials. By way of example, a surgical delivery device may be made from medical grade plastics and/or stainless steel. Further, a surgical delivery device may be disposable or reusable. Additionally, referring to a transorifice device, the flexible conduit and/or the extendable sleeves may be made from any biocompatible material or combination of materials such as, but not limited to, silicone, a polymer such as polyurethane, thermal plastic rubber (TPR), and/or a biocompatible metal such as stainless steel. Also, any other component of the devices described herein may also be made from one or more of the above materials. Further, surface treatments of the various device surfaces are possible. Such surface treatments may include altering the surface texture or adding a biocompatible coating such as silicone and/or a water-soluble personal lubricant, such as K-Y® jelly, to increase lubricity for easy passage of instruments, for example.

Further, while various embodiments disclosed herein contemplate using various components together as part of a surgical system, kit, and/or method, the individual components may be used independently as well. For example, a speculum, transorifice device, and/or surgical delivery device, according to any of the various embodiments, may be used independent of the other devices disclosed herein. Also, any or all of the instruments may be used in a non-NOTES procedure. For example, the various devices may be used through an incision made in the abdominal wall.

While the embodiments have been described, it should be apparent, however, that various modifications, alterations and adaptations to the embodiments may occur to persons skilled in the art with the attainment of some or all of the advantages of the various embodiments. For example, according to various embodiments, a single component may be replaced by multiple components, and multiple components may be replaced by a single component, to perform a given function or functions. This application is therefore intended to cover all such modifications, alterations and adaptations without departing from the scope and spirit of the appended claims.

The devices disclosed herein can be designed to be disposed of after a single use, or they can be designed to be used multiple times. In either case, however, the device can be reconditioned for reuse after at least one use. Reconditioning can include a combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

The devices described herein may be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. Alternatively a sterilizing gas or other sterilizing procedure may be used. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A speculum, comprising:
    a base defining an opening therethrough, the base comprising a first base portion and a second base portion pivotably coupled about a hinge to increase or decrease a size of the opening defined by the base;
    a first blade attached to the first base portion, the first blade extending transverse to the first base portion and comprising a first distal end;
    a second blade attached to the second base portion, the second blade extending transverse to the second base portion and comprising a second distal end, wherein the first blade and the second blade are movable with respect to each other about the hinge; and
    at least one locking assembly configured to releasably hold the first blade and the second blade relative to each other in at least one locked position, wherein, when the first blade and the second blade are in the at least one locked position, a shortest distance between the first distal end and a plane defined by the proximal surface is substantially equal to another shortest distance between the second distal end and the plane defined by the proximal surface, and wherein, when the first blade and the second blade are in the at least one locked position, the at least one locking assembly is structured to prevent the first blade from moving toward the second blade.

2. The speculum of claim 1, wherein the first blade and the second blade are movable with respect to each other without a handle.

3. The speculum of claim 1, wherein when the first blade and the second blade are in the at least one locked position, the first blade and the second blade are substantially parallel with respect to each other.

4. The speculum of claim 1, wherein the first blade and the second blade are movable with respect to each other such that the first distal end and the second distal end substantially move in the same plane.

5. The speculum of claim 1, further comprising a third blade attached to one of the first base portion and the second base portion, wherein the at least one locking assembly comprises a latch assembly that, when locked via a latch operatively coupled to at least one of the first base portion and the second base portion, prevents pivotable movement about the hinge, and wherein the at least one locking assembly further comprises a ratchet assembly to releasably hold the third blade with respect to the base.

6. The speculum of claim 1, wherein the at least one locking assembly comprises at least one ratchet assembly or at least one linkage assembly.

7. The speculum of claim 1, wherein when the first blade and the second blade are in the at least one locked position, the first blade and the second blade are held at a substantially fixed angle with respect to the base, and wherein the at least one locking assembly comprises at least one latch operatively coupled to at least one of the first base portion and the second base portion.

8. A transorifice device, comprising:
    a port assembly defining at least one port therein, the port assembly including a proximal side and a distal side;
    a flexible conduit extending distally from the distal side of the port assembly, the flexible conduit including a proximal portion adjacent to the port assembly and a distal portion flexibly positionable relative to the proximal portion between a first distal position and a second distal position, the first distal position more proximate to the proximal portion, wherein the flexible conduit further comprises a pliable ring located at the distal portion, wherein the pliable ring is positioned about a perimeter of the distal portion and is configured to bias the perimeter toward an open configuration, and wherein the flexible conduit is structured to extend within a body opening; and
    at least one support member structured to raise the port assembly with respect to the body opening such that a distance between the distal side of the port assembly and the body opening increases when the port assembly is raised, wherein, when the distal portion of the flexible conduit is located at the first distal position and the at least one support member raises the port assembly with respect to the body opening, the proximal portion of the flexible conduit is movable proximally with respect to the distal portion of the flexible conduit to locate the distal portion at the second distal position.

9. The transorifice device of claim 8, further comprising an extendable sleeve extending from the at least one port and located at least partially within the flexible conduit.

10. The transorifice device of claim 8, wherein the flexible conduit further comprises a suture connected to one of the pliable ring and the distal portion.

11. The transorifice device of claim 8, wherein the at least one support member is movably associated with the distal portion of the flexible conduit and extendable to the distal side of the port assembly.

12. The transorifice device of claim 8, wherein the flexible conduit extends through the at least one support member, and wherein the at least one support member comprises an expandable bladder.

13. A surgical delivery device, comprising:
    a body including a proximal end and a distal end, the body defining a tool receiving passageway therein including a proximal opening located at the proximal end and a distal opening located at the distal end;

a tip movably mounted to the distal end of the body such that the tip can move between an opened position and a closed position, wherein the tip is configured to incise tissue; and an expandable member surrounding at least part of the body and located adjacent the distal end of the body and proximal to the tip, wherein the expandable member comprises an expandable dimension, and wherein the expandable member is proximal to the distal opening when the tip is in the open position.

14. The surgical delivery device of claim 13, further comprising a suture holder located near the distal end of the body, wherein the suture holder is configured to releasably hold a suture.

15. The surgical delivery device of claim 13, wherein the tip comprises a material that is at least partially transparent.

* * * * *